US012805907B2

(12) United States Patent
Hultquist

(10) Patent No.: US 12,805,907 B2
(45) **Date of Patent: *Nov. 24, 2026**

(54) SKIN CARE METHODS, SYSTEMS, AND DEVICES

(71) Applicant: Warren R. Hultquist, Boulder, CO (US)

(72) Inventor: Warren R. Hultquist, Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/811,045

(22) Filed: Aug. 21, 2024

(65) Prior Publication Data

US 2025/0049473 A1 Feb. 13, 2025

Related U.S. Application Data

(62) Division of application No. 17/687,771, filed on Mar. 7, 2022, now Pat. No. 12,089,876, which is a division (Continued)

(51) Int. Cl.

*A61B 17/50* (2006.01)
*A61B 17/00* (2006.01)

(Continued)

(52) U.S. Cl.

CPC .............. *A61B 17/50* (2013.01); *A61B 17/30* (2013.01); *A61B 17/54* (2013.01); *A61B 90/20* (2016.02);

(Continued)

(58) Field of Classification Search

CPC ......... A61B 17/30; A61B 17/50; A61B 17/54; A61B 2017/00221; A61B 2017/00747;

(Continued)

(56) References Cited

U.S. PATENT DOCUMENTS

| | | | |
|---|---|---|---|
| 1,842,403 A * | 1/1932 | Hunsaker | A45D 26/0066 359/810 |
| 5,263,754 A | 11/1993 | Coleman | |

(Continued)

FOREIGN PATENT DOCUMENTS

| | | |
|---|---|---|
| CN | 103340594 | 9/2013 |
| CN | 103340594 A * | 10/2013 |

(Continued)

OTHER PUBLICATIONS

International Search Report and Written Opinion for PCT/US2015/016980, Oct. 13, 2015, ISA—USPTO.

(Continued)

*Primary Examiner* — Md N Haque
(74) *Attorney, Agent, or Firm* — Wilson Patent Law, LLC

(57) ABSTRACT

Methods, systems, and devices for skin care are provided. Some embodiments may include a device or system for skin care that may include a skin tool head portion, a skin tool head support that may be coupled with the skin tool head portion, and/or a portable microscope connector that may be configured to couple a portable microscope with the skin tool head support. Some embodiments include a device for skin care that may include a spacer configured to couple with a portable microscope. The spacer includes at least one aperture configured to facilitate the use of a skin tool. Some embodiments include a spacer coupled with a compressible structure configured to preclude a skin tool from contacting a portion of skin when in an uncompressed state and to allow the skin tool to contact the portion of skin when in a compressed state.

15 Claims, 37 Drawing Sheets

Related U.S. Application Data of application No. 16/589,312, filed on Oct. 1, 2019, now Pat. No. 11,266,443, which is a division of application No. 14/628,130, filed on Feb. 20, 2015, now Pat. No. 10,492,831.

(60) Provisional application No. 61/942,670, filed on Feb. 21, 2014.

(51) Int. Cl.

| | |
|---|---|
| ***A61B 17/30*** | (2006.01) |
| ***A61B 17/54*** | (2006.01) |
| ***A61B 90/00*** | (2016.01) |
| ***A61B 90/20*** | (2016.01) |
| ***A61B 90/25*** | (2016.01) |
| ***A61B 90/30*** | (2016.01) |

(52) U.S. Cl.
CPC .............. *A61B 90/25* (2016.02); *A61B 90/30* (2016.02); *A61B 2017/00221* (2013.01); *A61B 2017/00747* (2013.01); *A61B 2017/305* (2013.01); *A61B 2090/372* (2016.02)

(58) Field of Classification Search
CPC ........ A61B 2017/305; A61B 2090/372; A61B 90/20; A61B 90/25; A61B 90/30
See application file for complete search history.

(56) References Cited

U.S. PATENT DOCUMENTS

| | | | | |
|---|---|---|---|---|
| 5,343,536 | A | 8/1994 | Groh | |
| 5,370,648 | A * | 12/1994 | Cracraft | A61B 17/28 606/1 |
| 5,910,147 | A * | 6/1999 | Rosenberg | A61B 17/54 606/181 |
| 6,502,587 | B1 | 1/2003 | Kellum | |
| 6,572,625 | B1 * | 6/2003 | Rassman | A61B 17/32053 606/133 |
| 6,587,711 | B1 | 7/2003 | Alfano | |
| 7,073,832 | B1 | 7/2006 | LaVaque | |
| 7,785,339 | B2 | 8/2010 | Cohen | |
| 10,363,067 | B2 | 7/2019 | Hultquist | |
| 10,492,831 | B2 | 12/2019 | Hultquist | |
| 11,266,443 | B2 | 3/2022 | Hultquist | |
| 12,089,876 | B2 | 9/2024 | Hultquist | |
| 2006/0051339 | A1 | 3/2006 | Sivak | |
| 2007/0106306 | A1 | 5/2007 | Bodduluri | |
| 2009/0306498 | A1 * | 12/2009 | Bodduluri | A61B 5/0066 606/9 |
| 2010/0204686 | A1 | 8/2010 | Yaroslavsky | |
| 2011/0058030 | A1 | 3/2011 | Oglesby | |
| 2011/0134234 | A1 | 6/2011 | Kim | |
| 2011/0207806 | A1 | 8/2011 | Jia | |
| 2012/0022461 | A1 | 1/2012 | Schubert | |
| 2012/0172685 | A1 * | 7/2012 | Gilbert | A61B 5/0077 600/306 |
| 2013/0226214 | A1 | 8/2013 | Okuda | |
| 2013/0287873 | A1 | 10/2013 | Tsai | |
| 2013/0317314 | A1 | 11/2013 | Lampson | |
| 2013/0338627 | A1 | 12/2013 | Rylander | |
| 2014/0271953 | A1 | 9/2014 | Hwang | |
| 2015/0238274 | A1 | 8/2015 | Hultquist | |
| 2016/0249951 | A1 | 9/2016 | Hultquist | |
| 2020/0237405 | A1 | 7/2020 | Hultquist | |
| 2022/0296274 | A1 | 9/2022 | Hultquist | |

FOREIGN PATENT DOCUMENTS

| | | | |
|---|---|---|---|
| WO | WO 01/67956 | A2 * | 9/2001 |
| WO | WO0167956 | | 9/2001 |
| WO | WO2015127322 | | 8/2015 |

OTHER PUBLICATIONS

Restriction Requirement, U.S. Appl. No. 14/628,130, Aug. 25, 2017, USPTO.
Restriction Requirement, U.S. Appl. No. 14/628,130, Apr. 13, 2018, USPTO.
Non-Final Office Action, U.S. Appl. No. 14/628,130, Oct. 2, 2018, USPTO.
Final Office Action, U.S. Appl. No. 14/628,130, May 24, 2019, USPTO.
Notice of Allowance, U.S. Appl. No. 14/628,130, Aug. 19, 2019, USPTO.
Restriction Requirement, U.S. Appl. No. 15/149,114, Apr. 13, 2018, USPTO.
Non-Final Office Action, U.S. Appl. No. 15/149,114, Jul. 18, 2018, USPTO.
Final Office Action, U.S. Appl. No. 15/149,114, Jan. 18, 2019, USPTO.
Advisory Action, U.S. Appl. No. 15/149,114, Mar. 27, 2019, USPTO.
Notice of Allowance, U.S. Appl. No. 15/149,114, May 30, 2019, USPTO.
Non-Final Office Action, U.S. Appl. No. 16/589,312, filed Jul. 31, 2020, USPTO.
Final Office Action, U.S. Appl. No. 16/589,312, Apr. 16, 2021, USPTO.
Notice of Allowance, U.S. Appl. No. 16/589,312, Oct. 27, 2021, USPTO.
Notice of Allowance, U.S. Appl. No. 16/589,312, Nov. 18, 2021, USPTO.
Non-Final Office Action, U.S. Appl. No. 17/687,771, Jan. 27, 2023, USPTO.
Final Office Action, U.S. Appl. No. 17/687,771, Jul. 17, 2023, USPTO.
Notice of Allowance, U.S. Appl. No. 17/687,771, May 21, 2024, USPTO.
Notice of Allowance, U.S. Appl. No. 17/687,771, Jun. 3, 2024, USPTO.
Suvorna Skinpal s66. Advertisement [online]. Suvorna.com [retrieved on Jun. 21, 2023]. Retrieved from <https://www.suvorna.com/products/skinpal-s66?variant=8875216067>.

* cited by examiner

SKIN CARE METHODS, SYSTEMS, AND DEVICES

CROSS-REFERENCES TO RELATED APPLICATIONS

This application is a non-provisional patent application claiming priority benefit of U.S. Provisional Patent Application Ser. No. 61/942,670, filed on Feb. 21, 2014, and entitled "METHODS, SYSTEMS, AND DEVICES FOR SKIN CARE," the entire disclosure of which is herein incorporated by reference for all purposes.

BACKGROUND

Different tools and techniques may be utilized for skin care. For example, fingers, comedone extractors, and/or lancets may be utilized for opening and/or extruding clogged pores. However, there may be different issues that arise in utilizing these tools and techniques, such as applying an appropriate amount of pressure, avoiding skin damage, adequately viewing the treatment site, etc. There may thus be a need for tools and techniques that may provide for skin care that may address these different issues.

SUMMARY

The described features generally relate to one or more systems, methods, and/or devices for skin care. For example, some embodiments include a system that may include a portable, digital microscope and/or a comedone extractor coupled with the portable, digital microscope. At least a portion of the comedone extractor may be positioned at least within a field of view of the portable, digital microscope. Some embodiments include a device for comedone extraction that may include: a comedone extractor; a comedone extractor support configured to couple with the comedone extractor; and/or a portable microscope coupler configured to couple a portable microscope with the comedone extractor support. Some embodiments may include a device or system for skin care that may include multiple aspects such as a skin tool head portion, a skin tool head support that may be coupled with the skin tool head portion, and/or a portable microscope connector that may be configured to couple a portable microscope with the skin tool head support. The portable microscope may be configured to transmit information to a monitor, which may include a computer monitor, projector, tablet, smart device, optical-head mounted display, or other device that includes a visual screen, merely by way of example. This information may include visual information that may be transmitted wirelessly or over physical transmission media.

Some embodiments include a system for comedone extraction that may include: a portable, digital microscope; and/or a comedone extractor coupled with the portable, digital microscope, wherein at least a portion of the comedone extractor is positioned at least within a field of view of the portable, digital microscope.

Some embodiments include a device for comedone extraction that may include: a comedone extractor; a comedone extractor support configured to couple with the comedone extractor; and/or a portable microscope coupler configured to couple a portable microscope with the comedone extractor support.

Some embodiments include a device to facilitate skin care. The device may include: a skin tool head portion; a skin tool head support coupled with the skin tool head portion; and/or a portable microscope connector configured to couple a portable microscope with the skin tool head support.

In some embodiments of the device to facilitate skin care, the skin tool head support may be configured such that at least a portion of the skin tool head portion is positioned within a field of view of the portable microscope when the portable microscope connector is coupled with the portable microscope. In some cases, the field of view of the portable microscope includes at least within a focal plane or at a focal point of the portable microscope. In some embodiments, the skin tool head portion may include at least a comedone extractor, a lancet, a needle, or tweezers. Some embodiments may include a polarizer configured to polarize light from the portable microscope.

Some embodiments of the device to facilitate skin care may further include the portable microscope configured with at least a light element configured to fluoresce at least sebum or acne bacterium.

In some cases, the skin tool head support may include a first support portion and a second support portion, wherein the first support portion and the second support portion are configured to form an angle between the first support portion and the second head portion. In some cases, the angle may be at least a 45 degree angle. The angle may be adjustable to other angles in some cases.

In some embodiments, the portable microscope comprises a digital microscope. In some embodiments, the skin tool head support may be configured to couple with a variety of different skin tool head portions. The skin tool head support may be configured to facilitate displacing the skin tool head portion from a first position to a second position.

Some embodiments of the device to facilitate skin care may include a spacer configured to couple with the portable microscope. The spacer may include a working aperture configured to facilitate the use of at least the skin tool head portion or another skin tool. In some embodiments, the spacer may include a lens protector for the portable microscope. In some cases, at least the skin tool head portion or the skin tool support may be integrated with the spacer.

In some embodiments, the spacer is coupled with a compressible structure positioned between the spacer and the portable microscope. The compressible structure may be configured to preclude the skin tool head portion from contacting a portion of skin when the compressible structure is in an uncompressed state and to allow the skin tool head portion to contact the portion of skin when the compressible structure is in a compressed state.

Some embodiments include a device to facilitate skin care that may include a spacer configured to couple with a portable microscope, wherein the spacer comprises at least one aperture configured to facilitate the use of a skin tool.

In some embodiments, the spacer may be configured to telescope with respect to a body of the portable microscope. The spacer may be spring loaded in some cases. In some cases, the aperture may include a cutaway of the spacer. The aperture may include a channel extending from a first portion of the spacer to a second portion of the spacer in some cases. The aperture may extend through a body portion of the spacer between a first edge of the spacer and a second edge of the spacer in some cases. The aperture may extend from a first edge of the spacer distal with respect to the portable microscope in some cases. The aperture may extend from a second edge of the spacer proximal with respect to the portable microscope in some cases. The spacer may include a lens protector for the portable microscope in some cases. The spacer may be made of a flexible material in some cases.

Some embodiments include a compressible structure coupled with the spacer, where the compressible structure may be configured to be positioned between the spacer and the portable microscope. The compressible structure may include a spring-loaded platform. The compressible structure coupled with the spacer may be configured to preclude the skin tool from contacting a portion of skin when the compressible structure is in an uncompressed state and to allow the skin tool to contact the portion of skin when the compressible structure is in a compressed state.

Some embodiments include a method of skin care that may include: imaging at least a portion of skin or a portion of a skin tool head portion with respect to the portion of skin utilizing a portable microscope; and/or utilizing the skin tool head portion with respect to the portion of skin, wherein the skin tool head portion is coupled with the portable microscope.

In some embodiments, the method of skin care may utilize the skin tool head portion with respect to the portion of skin comprising applying pressure to the portion of skin with the skin tool head portion. Applying the pressure may include modulating the pressure.

Some embodiments of the method of skin care may include illuminating at least the portion of skin utilizing at least polarized light or ultraviolet light. Illuminating at least the portion of the skin further may include illuminating at least a hair shaft or comedone. Some embodiments of the method of skin care may include utilizing another skin tool head portion with respect to the portion of skin through an aperture of a spacer of the portable microscope. Some embodiments may not include a spacer.

Some embodiments of the method may include utilizing a spacer coupled with the portable microscope to anchor the portable microscope with respect to a portion of skin. In some cases, the spacer may be utilized to spread the portion of skin. The method may include moving the portable microscope towards the portion of skin, wherein moving the portable microscope exposes the skin tool head portion with respect to the spacer to allow the skin tool head portion to contact the portion of skin.

Some embodiments include a method of skin care that may include: imaging at least a portion of skin or a portion of a skin tool head portion with respect to the portion of skin utilizing a portable microscope; and/or utilizing the skin tool head portion with respect to the portion of skin, wherein the skin tool head portion is moved through an aperture of the portable microscope. In some embodiments, the skin tool head portion may include least a comedone extractor, a lancet, a needle, or tweezers. Other tools for skin care may also be utilized. Some embodiments may further include illuminating at least the portion of skin utilizing at least polarized light or ultraviolet light.

Some embodiments include a method of skin care that include imaging at least a portion of skin or a portion of a skin tool head portion with respect to the portion of skin utilizing a portable microscope. The skin tool head portion may be moved with respect to an aperture of a spacer coupled with the portable microscope. The skin tool head portion may be utilized with respect to the portion of skin. In some embodiments, the skin tool head portion includes least a comedone extractor, a lancet, a needle, or tweezers.

Some embodiments of the method may include moving the spacer with respect to the portion of skin. Some embodiments include utilizing the spacer to anchor the portable microscope with respect to the portion of skin. In some cases, the spacer may be utilized to spread the portion of skin. In some embodiments, the skin tool head portion is independent from the portable microscope.

In some embodiments, the skin tool head portion is coupled with the portable microscope. Some embodiments include moving the portable microscope towards to the portion of skin, where moving the portable microscope exposes the skin tool head portion with respect to the spacer to allow the skin tool head portion to contact the portion of skin. In some embodiments, a compressible structure positioned between the portable microscope and the spacer facilitates exposing the skin tool head portion with respect to the spacer. In some embodiments, at least a portion of the spacer comprises a flexible material to facilitate exposing the skin tool head portion with respect to the spacer.

In some embodiments, moving the skin tool head portion with respect to the aperture of the spacer includes moving the skin tool head portion through the aperture of the spacer.

Some embodiments may include systems, methods, and/or devices as described in the specification and/or shown in the figures.

Further scope of the applicability of the described methods, systems, and/or methods will become apparent from the following detailed description, claims, and drawings. The detailed description and specific examples are given by way of illustration only, since various changes and modifications within the spirit and scope of the description will become apparent to those skilled in the art.

BRIEF DESCRIPTION OF THE DRAWINGS

A further understanding of the nature and advantages of the different embodiments may be realized by reference to the following drawings. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DESCRIPTION

Figure 1A:
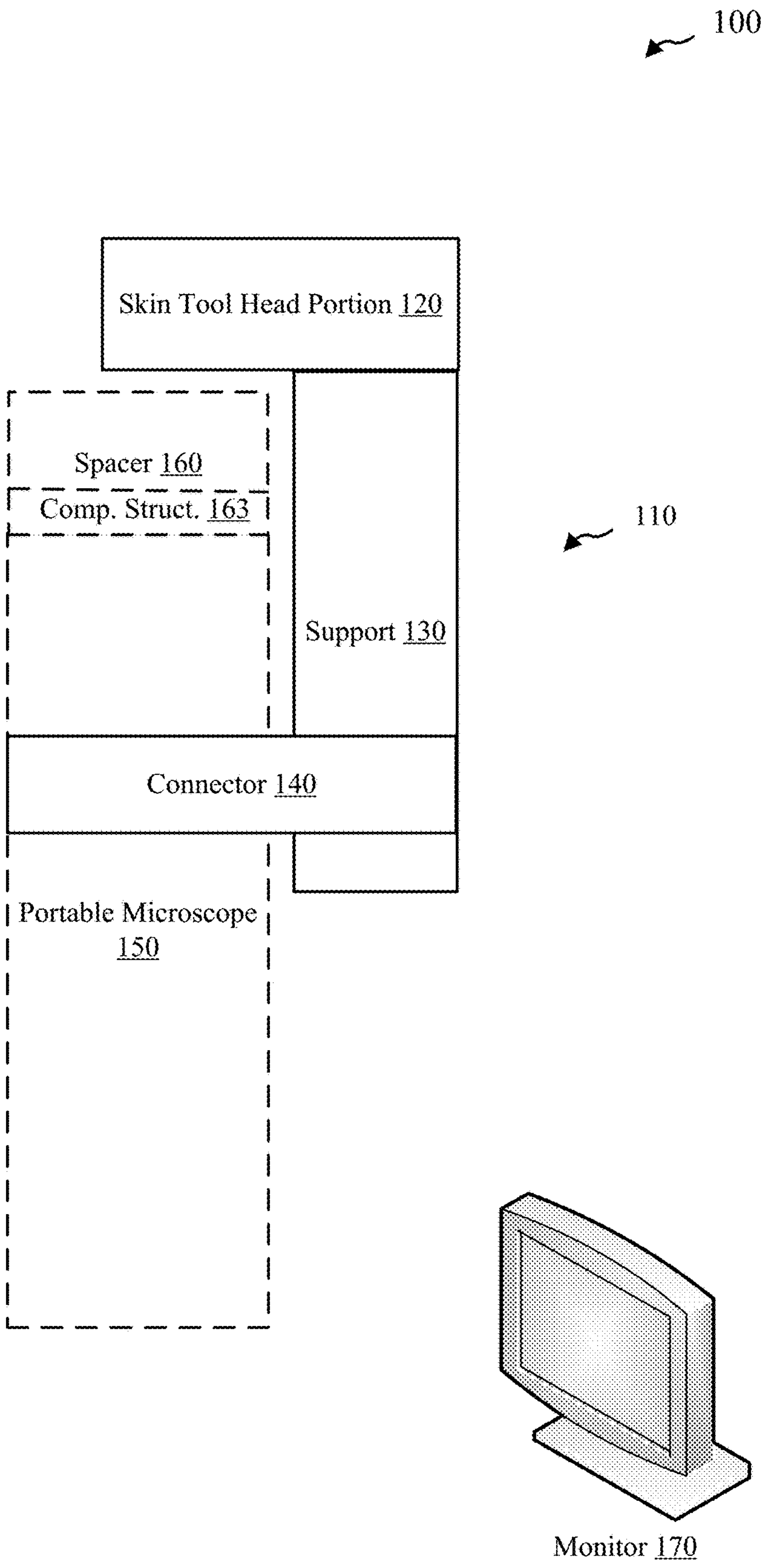
FIGS. 1A, 1B, 1C, 1D, 1E, IF, 1G, and 1H show systems to facilitate skin care in accordance with various embodiments.

The following description provides examples, and is not limiting of the scope, applicability, or configuration set forth in the claims. Changes may be made in the function and arrangement of elements discussed without departing from the spirit and scope of the disclosure. Various embodiments may omit, substitute, or add various procedures or components as appropriate. For instance, the methods described may be performed in an order different from that described, and various steps may be added, omitted, or combined. Also, features described with respect to certain embodiments may be combined in other embodiments.

Some embodiments may include skin care devices that may combine a digital, high resolution, manual or autofocus real-time video camera microscope, LED or other lighting source, and/or a selectable or interchangeable array of comedone extractors, tweezers, lances, probes, light filters, LED wavelength options, and lens spacers, skin spreaders, or skin anchors for highly effective, rapid identification and treatment of common skin conditions. Digital microscopes with a USB, Wi-Fi, or other video signal output may be utilized for magnification and illumination of objects. Some embodiments may include having different tool fixtures that enable the camera body to be the tool itself, and may be equipped or optimized for used as a skin care device. For example, the camera body may include a grip and/or tool handle in some cases.

Comedone extractors may be commonly available tools for clearing clogged pores, such as blackheads, whiteheads, or ingrown hairs. In some cases, a comedone extractor may include a rigid wire loop available in various wire gauges, sizes, and shapes optimized for surrounding a clogged pore and applying focused pressure via the tool-body to cause the sebum and/or pus of a pimple, pore, or hair follicle to extrude out of the skin and/or pores.

The term comedones may generally refer to different signs of acne, which may include, but is not limited to, a dilated (i.e., widened) hair follicle or pore filled with keratin squamae (i.e., skin debris), bacteria, and/or sebum (i.e., oil). Comedones may be closed or open. The term comedones may be the plural of comedo. A closed comedo may generally include an obstructed opening to the skin and may rupture in some cases to cause a low-grade skin inflammatory reaction in the area. A closed comedo may generally be referred to as a whitehead. An open comedo may generally have wide opening to the skin and may be capped with a blackened mass of skin debris. An open comedo may commonly be known as a blackhead. For the purposes of this document, the term comedone is generally singular and may be interchangeable with the term comedo. Comedones may generally be utilized as the plural form. A comedone extractor, which may also be referred to as a blackhead remover or acne remover, may include a variety of different tools designed for use to unblock and/or clear clogged pores. In some cases, a comedone extractor may include metal handle with a rigid metal wire loop or at one or both ends, though other materials and configurations may be utilized.

Some embodiments may address the different problems with self-treatment of common skin conditions and/or irritations. For example, using your fingers and/or fingernails in an attempt to pinch, pop, or pick at whiteheads, blackheads (open or closed comedones) may break the surface of the skin, break capillaries, and cause cysts or pustules to rupture above or beneath the skin, spreading infection and increasing inflammation. Trying to remove a splinter using fingers and fingernails may be equally damaging and ineffective. Fingers and fingernails in particular may be unsanitary, thus prone to spread infection when used for addressing spots or splinters in the skin. Different embodiments may address these issues in a variety of ways.

The use of comedone extractors and lancets for opening and extruding clogged pores or pimples may reduce the risk of infection and skin damage. However, using the correct amount of pressure—to avoid damaging the skin via breaking the surface or breaking capillaries—may be difficult. It may also be difficult to place a comedone extractor in the optimal location with the tool at the correct angle and orientation to be sure the problem-pore or follicle is perfectly surrounded for a clean and effective extrusion. Without magnification and/or illumination, performing self-extraction via a comedone tool may lead the user to press too hard, too fast, and in the wrong location or direction, which may cause unnecessary skin damage and ineffective or incomplete extraction of unwanted material from the skin. Different embodiments may address one or more of these issues.

The use of lancets for piercing pimples may be risky and may require proper technique and control and may be performed optimally by a doctor, dermatologist, or esthetician. Even under optimal conditions, with proper magnification and/or illumination and access to the spot for example, proper technique may be involved. Improper lancing (for example, on the top of a pustule-rather than from the side) may lead to worse infection and inflammation. Self-lancing may be dangerous-particularly if one lances the wrong location or goes too deep. Different embodiments may address one or more of these issues.

The use of tweezers or pins for removing splinters, slivers, ingrown hairs, or other things is common. Both tools may present risk of infection if not properly sterilized.

Infection can be spread by penetrating and damaging the skin with these devices. Different embodiments may address one or more of these issues.

Some spots or splinters may be located such that self-extraction via a comedone tool, tweezers, or use of fingers may be difficult (for example, a spot in the middle of your back, out of view via direct eyesight or even out of view or reach with assistance of a mirror). In these cases, help from another person may be involved. This may entail the inconvenience and cost of a visit to a professional, or imposing on someone else to help with an awkward task of maintaining personal hygiene. Different embodiments may address one or more of these issues.

While professionals, like dermatologists and estheticians, may have magnifying lamps or goggles, consumers may be left with the mirror and lighting in their bathroom. It may be difficult to see exactly what's going on with a given spot if the lighting is poor or the distance between the spot, the mirror, and the eyes may be too long to allow details to be visible and sharp. Different embodiments may address one or more of these issues.

People with poor or diminished eyesight may have trouble seeing details with spots on the skin in general, whether directly, via a mirror, or even when assisted with a professional magnifying task lens and/or mirror. As we age, our ability to focus may make viewing close-up details more difficult. Different embodiments may address one or more of these issues.

Ingrown hairs may be difficult to identify because the hair shaft is hidden, and may be masked in an area with many other follicles. If the hair shaft itself is transparent, it may be hard to see that a hair is involved at all. People may mistake an ingrown hair for a pimple or mole, for example. Different embodiments may address one or more of these issues.

While high magnification may provide the ability to accurately audit the skin and address each pore and hair, it may also make a thorough exam tedious and time consuming. Different embodiments may address one or more of these issues.

Some embodiments may address one or more of these issues by combining a digital/optical microscope and LED or other lighting with a modified comedone extractor loop attached to the body of the device, which may be at a fixed focal length from the lens, a highly magnified real-time video signal may be sent to a display device, which may reduce and/or eliminate one or more of the problems above.

In some embodiments, the body of the tool may be as an extended handle for manipulating the attached/integrated extractor loop, or other interchangeable/selectable tools for treating common skin conditions. The combination of lighting, magnification, and fixing of the extraction loop to the body of the scope may allow use of the device with a single hand to: rapidly scout for spots in general, and catch spots missed with the naked eye or even those too small to see with a common magnifying mirror or task light; optimally position and orient the tool perpendicular to the skin; use the magnified, real-time video image display to properly center the loop around the spot; and/or apply the proper amount of modulated pressure to the tool body in order to observe the speed, direction, and degree of completion for the extraction.

In some embodiments, this real-time, magnified visual feedback and control eliminates or reduces the impact of the tool on the skin and keeps the tool and skin in focus for consistently effective extractions. Since the device may be used to view anywhere on the exterior of the body, spots that are otherwise inaccessible or difficult to reach may be self-treated or better treated with assistance. People with only one working hand can use different embodiments to perform pore extractions that would otherwise require two hands, or assistance from another person.

Since the tool itself may include a camera as well as a microscope, proper technique may be directly captured to a digital image or video, then saved and shared. A library of highly magnified skin issues may be catalogued and accessed to help the user learn about skin conditions and what to look for, and determine which can or can't be addressed using the tool. Some embodiments may include automated image identification.

In some embodiments, videos or still images may be taken for diagnostic purposes & measurements, providing highly accurate visual information for documenting and analyzing skin issues. The magnification may allow the user to learn which skin anomalies may be of concern, which can be self-treated. The camera may allow capturing and/or sharing of images or videos which can be professionally assessed.

After shaving, whiskers or hairs may begin to grow beneath the outer layer of skin, which may cause itching, irritation, and possibly infection as the body tries to reject the hair. This is commonly known as an ingrown hair. Even under high magnification and conventional lighting, some hairs may be difficult to see because they are transparent. An optical property known as birefringence can be used in different embodiments by placing a filter in front of the light source to polarize the light and cause the hair to illuminate in contrast to the surrounding skin. This may help locate hairs that might otherwise be overlooked due to transparency.

LED lights emitting a wavelength at approximately 410 microns, and other wavelengths, may be used to cause acne bacterium and sebum (both present in clogged and/or infected pores or follicles) to fluoresce red or orange (though other colors may also be utilized), further enhancing the ability to distinguish healthy, normal pores and hair follicles from infected and/or clogged pores and follicles. By including one or more of these specific LEDs in some embodiments, the task of scanning the skin may be performed quickly because the clogged and/or infected pores and follicles are highlighted, and the normal pores and follicles are not.

Thus, in some embodiments, a system for comedone extraction may include: a portable, digital microscope; and/or a comedone extractor coupled with the portable, digital microscope, wherein at least a portion of the comedone extractor is positioned at least within a field of view of the portable, digital microscope.

Some embodiments include a device for comedone extraction that may include: a comedone extractor; a comedone extractor support configured to couple with the comedone extractor; and/or a portable microscope coupler configured to couple a portable microscope with the comedone extractor support.

Turning now to FIG. 1A, a system 100 to facilitate skin care is provided in accordance with various embodiments. System 100 may include a device 110, in particular, to facilitate skin care. The device 110 may include multiple aspects such as a skin tool head portion 120, a skin tool head support 130 that may be coupled with the skin tool head portion 120, and/or a portable microscope connector 140 that may be configured to couple a portable microscope 150 with the skin tool head support 140. Portable microscope 150 may be configured to transmit information to a monitor 170, which may include a computer monitor, projector, tablet, smart device, optical-head mounted display, or other device that includes a visual screen, merely by way of example. This information may include visual information that may be transmitted wirelessly or over physical transmission media. The visual information may include imaging. The imaging may include static imagining, such as a photograph imaging, or live imaging, such as video imaging.

In some cases, the skin tool head support 130 is configured such that at least a portion of the skin tool head portion 120 is positioned within a field of view of the portable microscope 150 when the portable microscope connector 140 is coupled with the portable microscope 150. The field of view of the portable microscope 150 may include at least within a focal plane or at a focal point of the portable microscope 150. The skin tool head portion 120 may include a variety of different skin tools including, but not limited to, at least a comedone extractor, a lancet, a needle, or tweezers. The portable microscope connector 140 may couple with the portable microscope 150 in a variety of different ways, including, but not limited to, permanently or removably connecting with the portable microscope 150. Merely by way of example, the portable microscope connector 140 may involve the use of adhesives, physical connectors such as rivets, screws, and/or bolts, Velcro straps, clamps, and or other physical means for coupling the skin tool head support 130 with the portable microscope 150 through the portable microscope connector 140. In some cases, the portable microscope connector 140 may involve integrating the skin tool head support 130 with the portable microscope 150 through a body of the portable microscope 150 or other aspects of the portable microscope 150.

Some embodiments of device 110 and/or system 100 may include a polarizer configured to polarize light from the portable microscope 150. The portable microscope 150 may be configured with at least a light element configured to fluoresce at least sebum or acne bacterium.

In some embodiments, the skin tool head support 130 includes a first support portion and a second support portion. The first support portion and the second support portion may be configured to form an angle between the first support portion and the second head portion. Several examples of this configuration are shown in the subsequent figures. In some cases, the angle may be at least a 45 degree angle, though other angles and/or arcs may be utilized. In some cases, the angle or arc may be adjustable.

In some embodiments, the portable microscope 150 includes a digital microscope. In some embodiments, the skin tool head support 130 is configured to couple with a variety of different skin tool head portions. The skin tool head support 130 may be configured to facilitate displacing the skin tool head portion 120 from a first position to a second position.

Some embodiments include a spacer 160 configured to couple with the portable microscope 150. The spacer 160 may include a working aperture configured to facilitate the use of at least the skin tool head portion 120 or another skin tool. The spacer 160 may include a lens protector for the portable microscope 150. In some embodiments, at least the skin tool head portion 120 or the skin tool support 130 is integrated with the spacer 160. In some embodiments, the spacer 160 is coupled with or includes a compressible structure or portion 163 positioned between the spacer and the portable microscope. The compressible structure 163 may be configured to preclude the skin tool head portion 120 from contacting a portion of skin when the compressible structure is in an uncompressed state and to allow the skin tool head portion 120 to contact the portion of skin when the compressible structure 163 is in a compressed state. The compressible structure 163 may include a spring-loaded platform in some cases. The compressible structure 163 may be configured out of other compressible materials such as flexible plastic and/or rubber. Some embodiments, for example, may include a compressible cuff.

Figure 1B:
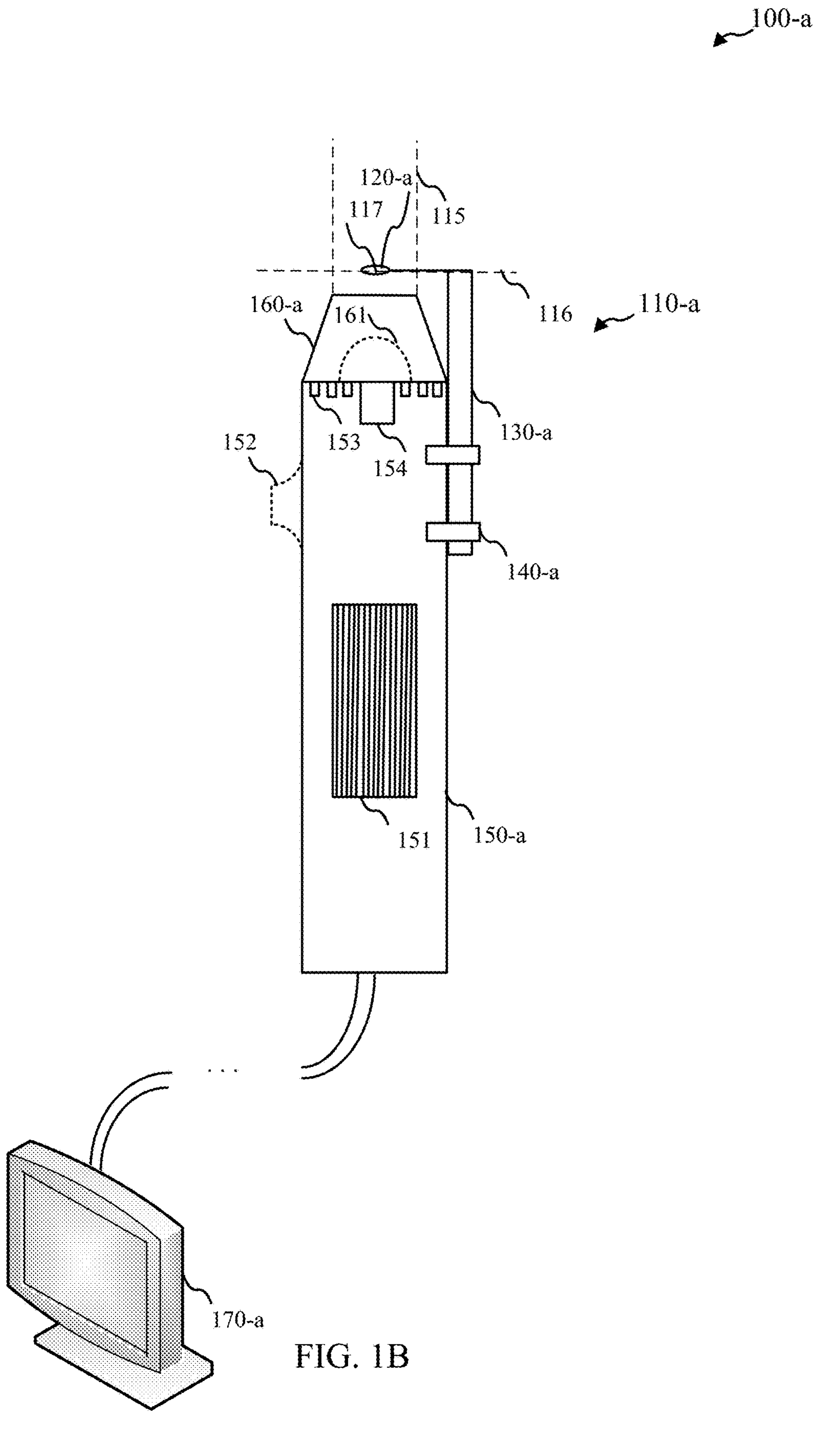

FIG. 1B shows a specific example of a system 100-*a* to facilitate skin care in accordance with various embodiments. System 100-*a* may be an example of system 100 of FIG. 1A. System 100-*a* may include a device 110-*a*, in particular, to facilitate skin care. Device 110-*a* may be an example of device 110 of FIG. 1A. The device 110-*a* may include multiple aspects such as a skin tool head portion 120-*a*, a skin tool head support 130-*a* that may be coupled with the skin tool head portion 120-*a*, and/or a portable microscope connector 140-*a* that may be configured to couple a portable microscope 150-*a* with the skin tool head support 130-*a*. In this example, device 110-*a* may be configured to transmit information to a monitor 170-*a* over physical transmission media, though system 100-*a* may be configured for wireless communication in some embodiments.

In some cases, the skin tool head support 130-*a* is configured such that at least a portion of the skin tool head portion 120-*a* is positioned within a field of view 115 of the portable microscope 150-*a* when the portable microscope connector 140-*a* is coupled with the portable microscope 150-*a*. The field of view 115 of the portable microscope 150-*a* may include at least within a focal plane 116 or at a focal point 117 of the portable microscope 150-*a*. The skin tool head portion 120-*a* may include a variety of different skin tools; in this example, the skin tool head portion 120-*a* is shown as a comedone extractor, though other skin tools may be utilized.

In this example, portable microscope 150-*a* may be shown with a focusing element 151, which may be utilized to focus a camera and/or lens configuration 154. Portable microscope 150-*a* may also include an ergonomic feature, such as a finger rest 152, which may either be in one or more portions or fully circumferential around the portable microscope 150-*a*. Portable microscope 150-*a* may include one or more light elements 153, which may include, but are not limited to, light emitting diodes (LEDs). Some embodiments may include a polarizer configured to polarize light from the portable microscope 150-*a*. The portable microscope 150 may be configured with at least a light element configured to fluoresce at least sebum or acne bacterium. While this embodiment and others may involve manual focusing elements, such as focusing element 151, some embodiments may also be configured for autofocusing by the portable microscope 150-*a*.

In system 100-*a*, a spacer 160-*a* is shown that may be configured to couple with the portable microscope 150-*a*. The spacer 160-*a* may include a working aperture 161 configured to facilitate the use of another skin tool (not shown). The spacer 160-*a* may include a lens protector for the portable microscope 150-*a*.

Figure 1C:
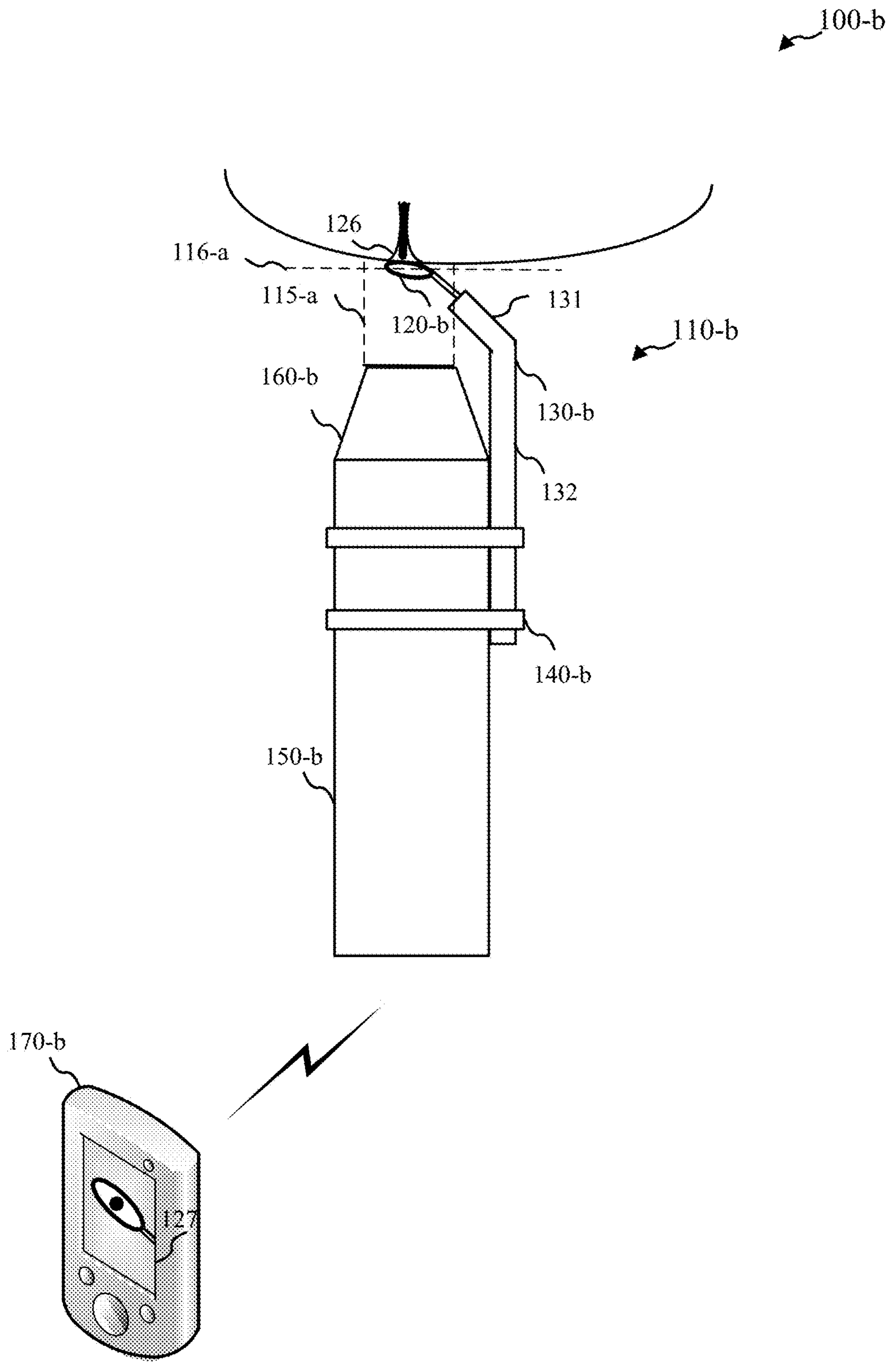

Turning now to FIG. 1C, a system 100-*b* to facilitate skin care is provided in accordance with various embodiments. System 100-*b* may be an example of system 100 of FIG. 1A. System 100-*b* may include a device 110-*b*, in particular, to facilitate skin care. Device 110-*b* may be an example of device 110 of FIG. 1A. The device 110-*b* may include multiple aspects such as a skin tool head portion 120-*b*, a skin tool head support 130-*b* that may be coupled with the skin tool head portion 120-*b*, and/or a portable microscope connector 140-*b* that may be configured to couple a portable microscope 150-*b* with the skin tool head support 130-*b*. Device 110-*b* may be configured to transmit information to a monitor 170-*b*, which in this example is shown as a tablet or smart device, though other devices that include a visual screen may be utilized merely by way of example. In some embodiments, the system 100-*b* is configured as a wireless system, though may be configured also as a physical transmission medium also. System 100-*b* is also shown with a spacer 160-*b* that may be coupled with portable microscope 150-*b*.

In some cases, the skin tool head support 130-*b* is configured such that at least a portion of the skin tool head portion 120-*b* is positioned within a field of view 115-*a* of the portable microscope 150-*b* when the portable microscope connector 140-*b* is coupled with the portable microscope 150-*b*. The field of view of the portable microscope 150-*b* may include at least within a focal plane 116-*a*, a range or depth of focus, and/or at a focal point of the portable microscope 150-*b*. The skin tool head portion 120-*b* may include a variety of different skin tools including, but not limited to, at least a comedone extractor, a lancet, a needle, or tweezers; in this example, the skin tool head portion 120-*b* is shown as a comedone extractor. FIG. 1C also shows a skin site 126, which may include a portion of skin, a comedone, a hair, etc. In this example, the image 127 of the skin site 126 and/or skin tool head portion 120-*b* may be shown of the screen of the monitor 170-*b*. The image may include a static image, such as a photograph, or a live image, such as video.

In some embodiments, the skin tool head support 130-*b* includes a first support portion 131 and a second support portion 132. The first support portion 131 and the second support portion 131 may be configured to form an angle between the first support portion 131 and the second head portion 132. In some cases, the angle may be at least a 45 degree angle, as shown in FIG. 1C, though other angles and/or arcs may be utilized.

Figure 1D:
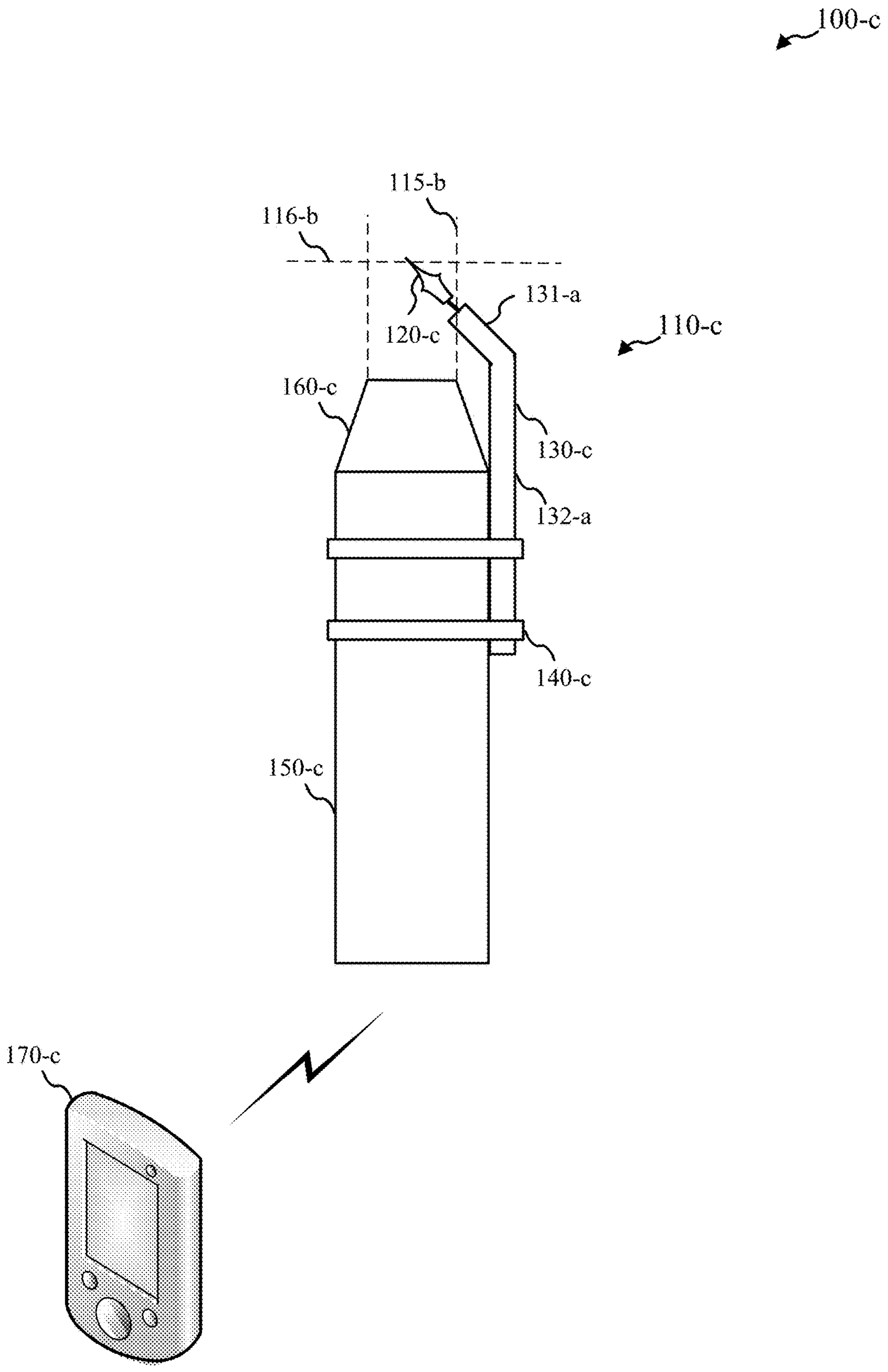

Turning now to FIG. 1D, a system 100-*c* to facilitate skin care is provided in accordance with various embodiments. System 100-*c* may be an example of system 100 of FIG. 1A. System 100-*c* may include a device 110-*c*, in particular, to facilitate skin care. Device 110-*c* may be an example of device 110 of FIG. 1A. The device 110-*c* may include multiple aspects such as a skin tool head portion 120-*c*, a skin tool head support 130-*c* that may be coupled with the skin tool head portion 120-*c*, and/or a portable microscope connector 140-*c* that may be configured to couple a portable microscope 150-*c* with the skin tool head support 130-*c*. Device 110-*c* may be configured to transmit information to a monitor 170-*c*, which in this example is shown as a tablet or smart device, though other devices that includes a visual screen may be utilized merely by way of example. System 100-*c* may be configured as a wireless system, though may be configured also as a physical transmission medium. System 100-*c* is also shown with a spacer 160-*c* that may be coupled with portable microscope 150-*c*.

In some cases, the skin tool head support 130-*c* is configured such that at least a portion of the skin tool head portion 120-*c* is positioned within a field of view 115-*b* of the portable microscope 150-*c* when the portable microscope connector 140-*c* is coupled with the portable microscope 150-*c*. The field of view of the portable microscope 150-*c* may include at least within a focal plane 116-*b* or at a focal point of the portable microscope 150-*c*. The skin tool head portion 120-*c* may include a variety of different skin tools including, but not limited to, at least a comedone extractor, a lancet, a needle, or tweezers; in this example, the skin tool head portion 120-*c* is shown as a lancet.

In some embodiments, the skin tool head support 130-*c* includes a first support portion 131-*a* and a second support portion 132-*a*. The first support portion 131-*a* and the second support portion 131-*a* may be configured to form an angle between the first support portion 131-*a* and the second head portion 132-*a*. In some cases, the angle may be least a 45 degree angle, as shown in FIG. 1B, though other angles and/or arcs may be utilized, such as a 90 degree angle, merely by way of example.

Figure 1E:
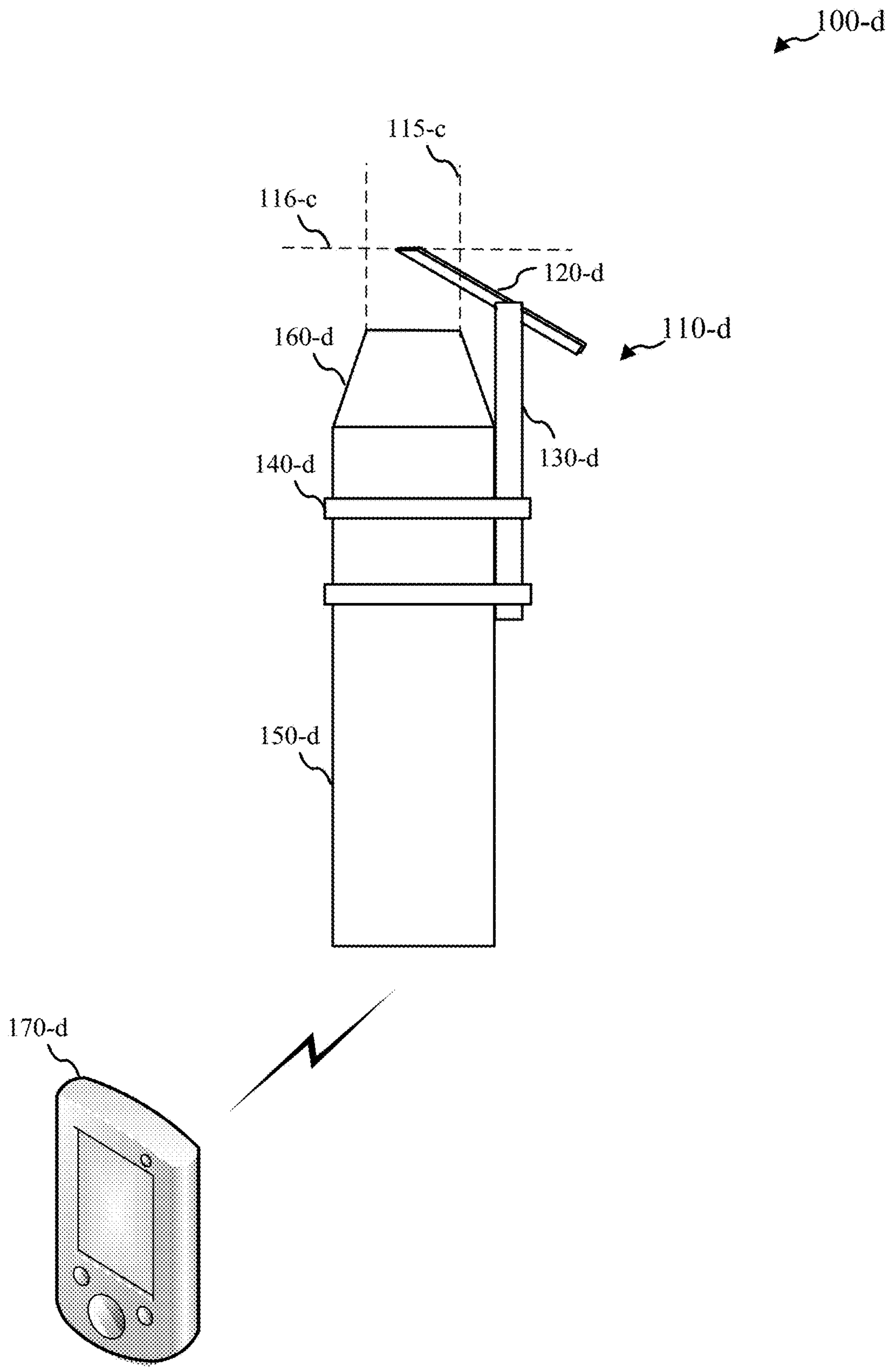

Turning now to FIG. 1E, a system 100-*d* to facilitate skin care is provided in accordance with various embodiments. System 100-*d* may be an example of system 100 of FIG. 1A. System 100-*d* may include a device 110-*d*, in particular, to facilitate skin care. Device 110-*d* may be an example of device 110 of FIG. 1A. The device 110-*d* may include multiple aspects such as a skin tool head portion 120-*d*, a skin tool head support 130-*d* that may be coupled with the skin tool head portion 120-*d*, and/or a portable microscope connector 140-*d* that may be configured to couple a portable microscope 150-*d* with the skin tool head support 130-*d*. Device 110-*d* may be configured to transmit information to a monitor 170-*d*, which in this example is shown as a tablet or smart device, though other devices that include a visual screen may be utilized merely by way of example. System 100-*d* may be configured as a wireless system, though may be configured also as a physical transmission medium also. System 100-*d* is also shown with a spacer 160-*d* that may be coupled with portable microscope 150-*d*.

In some cases, the skin tool head support 130-*d* is configured such that at least a portion of the skin tool head portion 120-*d* is positioned within a field of view 115-*c* of the portable microscope 150-*d* when the portable microscope connector 140-*d* is coupled with the portable microscope 150-*d*. The field of view 115-*c* of the portable microscope 150-*d* may include at least within a focal plane 116-*c*, a range or depth of focus, and/or at a focal point of the portable microscope 150-*d*. The skin tool head portion 120-*d* may include a variety of different skin tools including, but not limited to, at least a comedone extractor, a lancet, a needle, or tweezers; in this example, the skin tool head portion 120-*d* is shown as tweezers. In some embodiments, the skin tool head portion 120-*d*, such as the shown tweezers, may be manually and/or automatically actuated.

Figure 1F:
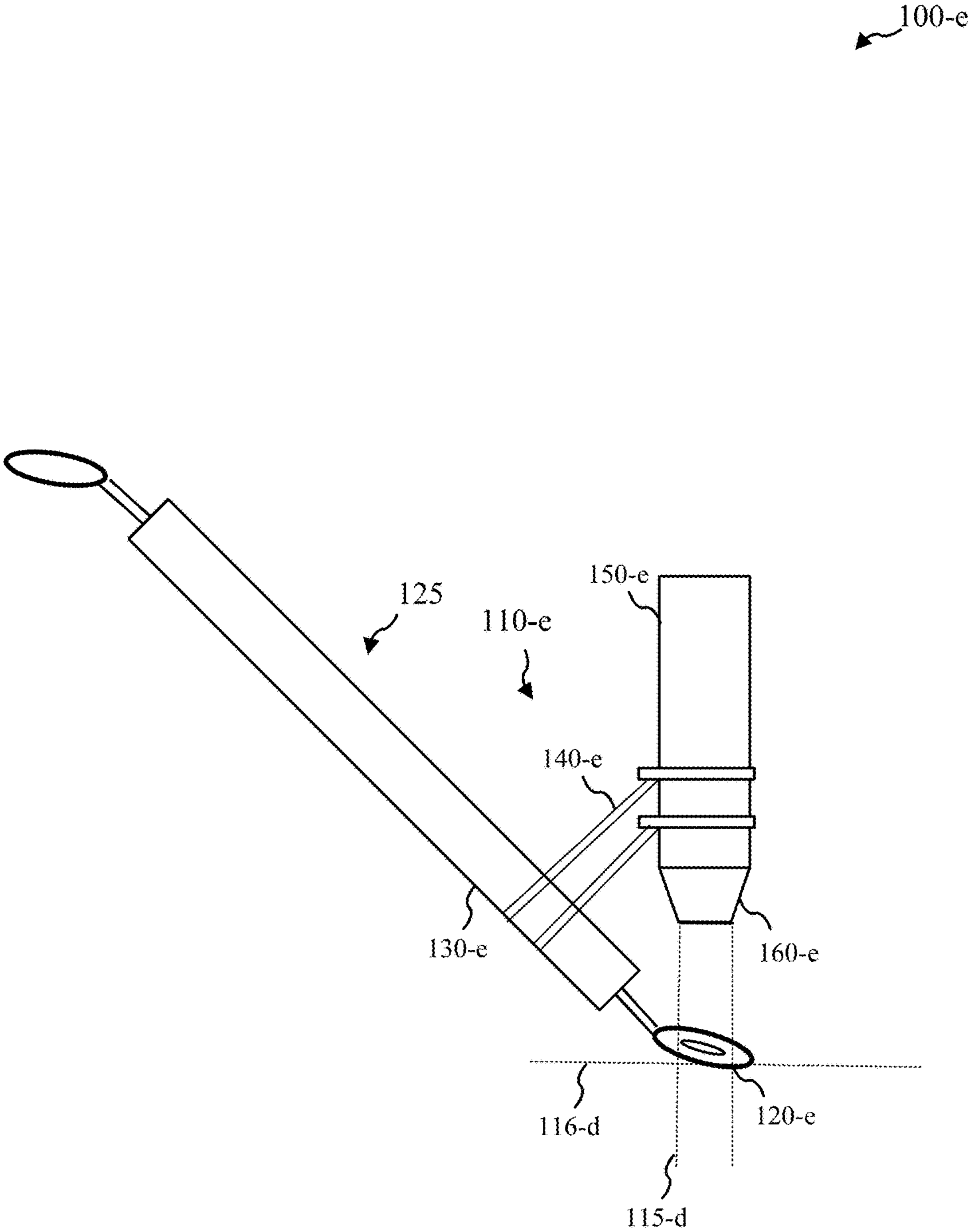

Turning now to FIG. 1F, a system 100-*e* to facilitate skin care is provided in accordance with various embodiments. System 100-*e* may be an example of system 100 of FIG. 1A. System 100-*e* may include a device 110-*e*, in particular, to facilitate skin care. Device 110-*e* may be an example of device 110 of FIG. 1A. The device 110-*e* may include multiple aspects such as a skin tool head portion 120-*e*, a skin tool head support 130-*e* that may be coupled with the skin tool head portion 120-*e*, and/or a portable microscope connector 140-*e* that may be configured to couple a portable microscope 150-*e* with the skin tool head support 140-*e*. Device 110-*e* may be configured to transmit information to a monitor (not shown), but described above in different embodiments. In some embodiments system 100-*e* also includes with a spacer 160-*e* that may be coupled with portable microscope 150-*e*.

System 100-*e* is configured to utilize a skin care tool 125, such as a comedone extractor, that includes skin tool head portion 120-*e* and skin tool head support 130-*e*. In this example, the portable microscope 150-*e* is coupled with the skin care tool 125 utilizing the portable microscope connector 140-*e*.

In some cases, the skin tool head support 130-*e* is configured such that at least a portion of the skin tool head portion 120-*e* is positioned within a field of view 115-*d* of the portable microscope 150-*e* when the portable microscope connector 140-*e* is coupled with the portable microscope 150-*e*. The field of view 115-*d* of the portable microscope 150-*e* may include at least within a focal plane 116-*d*, a range or depth of focus, and/or at a focal point of the portable microscope 150-*e*.

Figure 1G:
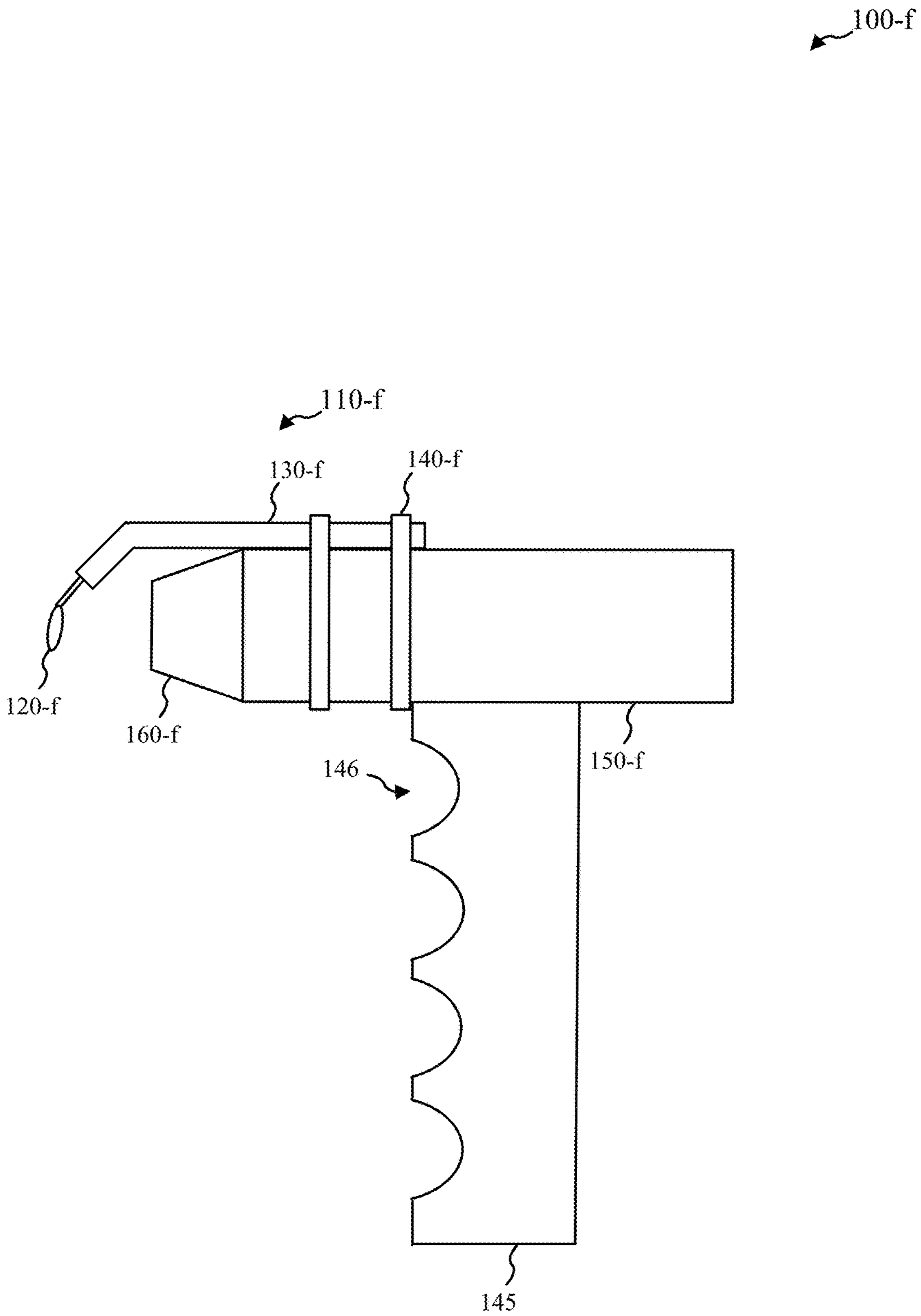

Turning now to FIG. 1G, a system 100-*f* to facilitate skin care is provided in accordance with various embodiments. System 100-*f* may be an example of system 100 of FIG. 1A. System 100-*f* may include a device 110-*f*, in particular, to facilitate skin care. Device 110-*f* may be an example of device 110 of FIG. 1A. The device 110-*f* may include multiple aspects such as a skin tool head portion 120-*f*, a skin tool head support 130-*f* that may be coupled with the skin tool head portion 120-*f*, and/or a portable microscope connector 140-*f* that may be configured to couple a portable microscope 150-*f* with the skin tool head support 130-*f*. Device 110-*f* may be configured to transmit information to a monitor (not shown), but described above in different embodiments. System 100-*f* may include a spacer 160-*f* that may be coupled with portable microscope 150-*f*. The device 110-*f* may be positioned a various adjustable angles with respect to the handle 145 in some embodiments.

In this example, a handle 145 may be coupled with the portable microscope 150-*f* to facilitating positioning the device 110-*f*. In some cases, the handle 145 may be configured with finger indents 146 to facilitate gripping of the handle. Handle 145 may be coupled with the portable microscope connector 140-*f* in some embodiments. The device 110-*f* may be positioned at various angles with respect to the handle 145 in some embodiments. The various angles may be adjustable or fixed in some embodiments. These variations may provide for different ergonomic uses.

Figure 1H:
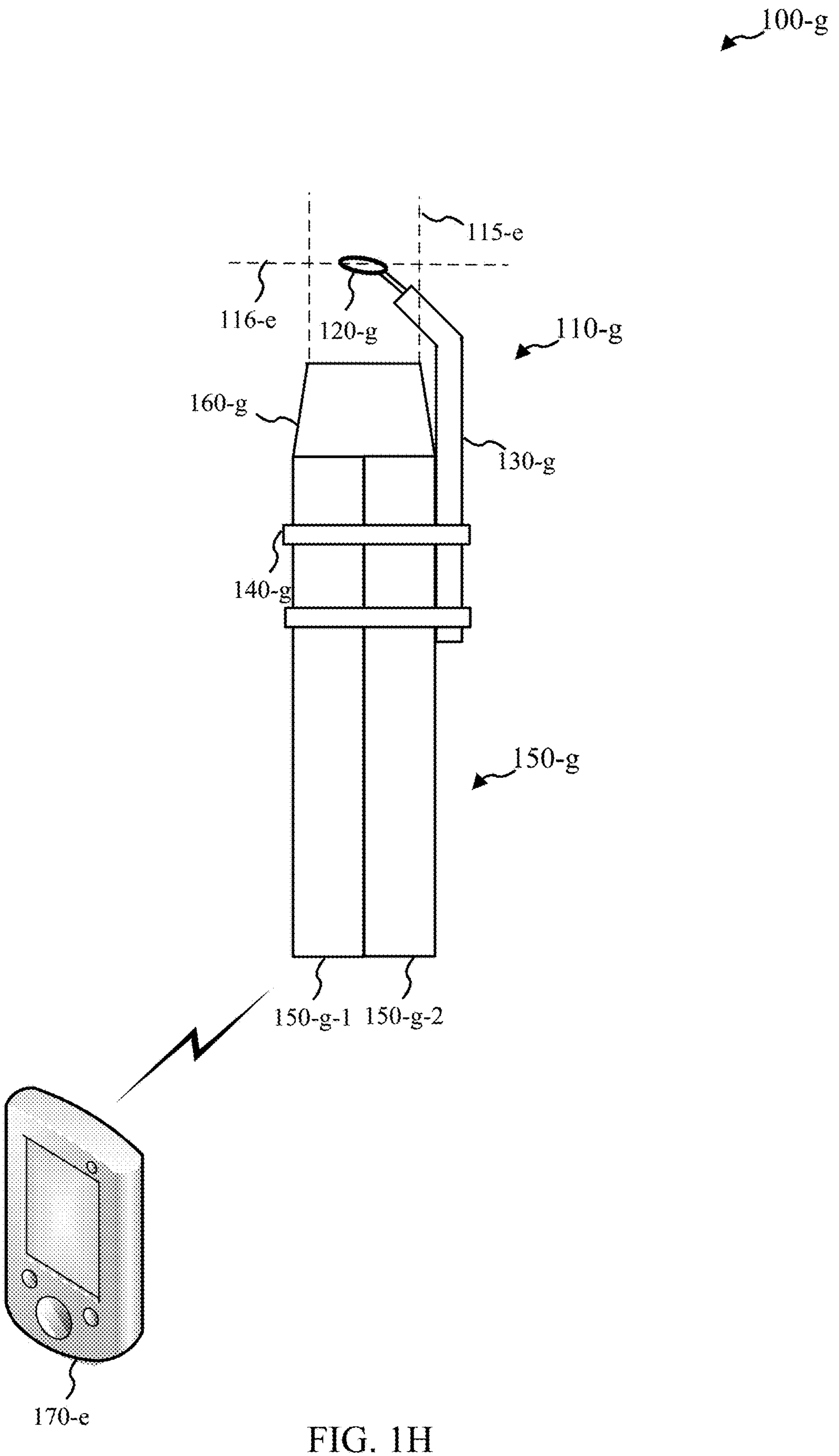

Turning now to FIG. 1H, a system 100-*g* to facilitate skin care is provided in accordance with various embodiments. System 100-*g* may be an example of system 100 of FIG. 1A. System 100-*g* may include a device 110-*g*, in particular, to facilitate skin care. Device 110-*g* may be an example of device 110 of FIG. 1A. The device 110-*g* may include multiple aspects such as a skin tool head portion 120-*g*, a skin tool head support 130-*g* that may be coupled with the skin tool head portion 120-*g*, and/or a portable microscope connector 140-*g* that may be configured to couple a portable microscope 150-*g* with the skin tool head support 130-*g*. Device 110-*g* may be configured to transmit information to a monitor 170-*e*. System 100-*g* may include a spacer 160-*g* that may be coupled with portable microscope 150-*g*.

In this example, portable microscope 150-*g* is configured as two microscopes 150-*g*-1/150-*g*-2 or two cameras in order to create a stereoscopic view of a skin site. The skin tool head support 130-*g* is configured such that at least a portion of the skin tool head portion 120-*g* is positioned within a field of view 115-*e* of the stereoscopic portable microscope 150-*g* when the portable microscope connector 140-*g* is coupled with the stereoscopic portable microscope 150-*g*. The field of view 115-*e* of the portable microscope 150-*g* may include at least within a focal plane 116-*e*, a range or depth of focus, and/or at a focal point of the stereoscopic portable microscope 150-*g*.

Figure 2A:
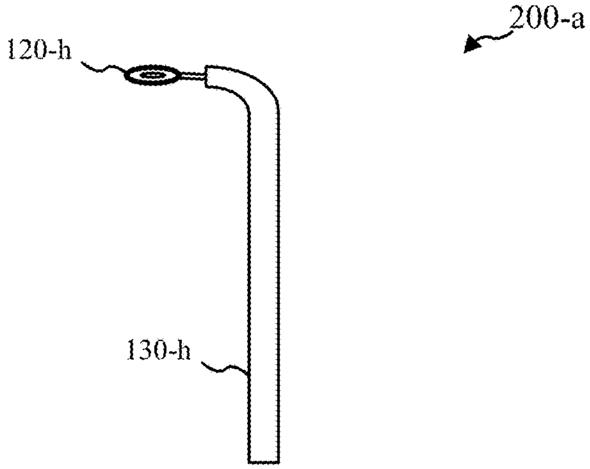
FIGS. 2A, 2B, and 2C show configurations to facilitate skin care in accordance with various embodiments.
Figure 2B:
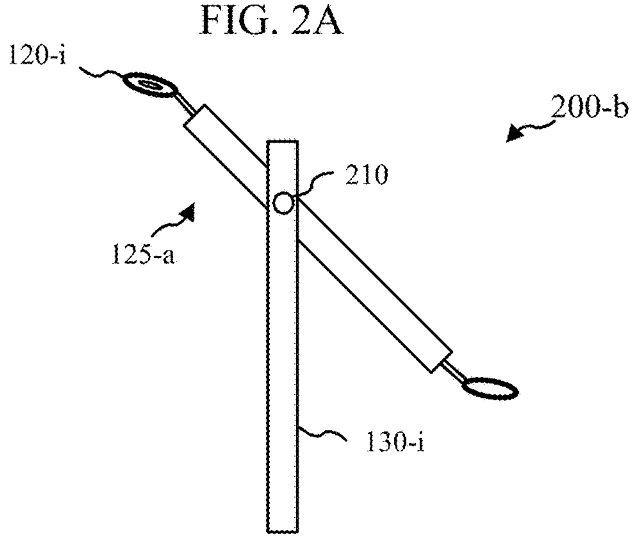
Figure 2C:
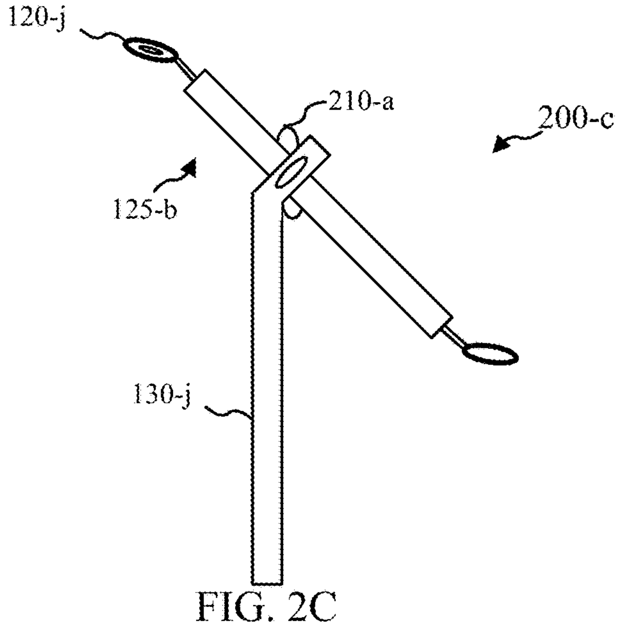

Turning now to FIGS. 2A, 2B, and 2C, these figures show different aspects of a device such as device 100 of FIG. 1A, in particular, showing the aspects of a skin tool head portion 120 and a skin tool head support 130. FIG. 2A shows a configuration 200-*a* that includes a skin tool head portion 120-*h* and a skin tool head support 130-*h* in accordance with various embodiments. In this example, the skin tool head portion 130-*h* is curved to provide a rounded support for the skin tool head portion 130-*h*. FIG. 2B shows a configuration 200-*b* that includes a skin tool head portion 120-*i* that may be configured as part of a skin tool 125-*a*, such as a standard comedone extractor in accordance with various embodiments. In this case, the skin tool head support 130-*i* may be configured to support the skin tool 125-*a*. This may include the use of coupler 210 such as a bolt or other mechanism for connecting the skin tool 125-*a* to the skin tool head support 130-*i*. FIG. 2C shows a configuration 200-*c* that includes a skin tool head portion 120-*j* that may be configured as part of a skin tool 125-*b*, such as a standard comedone extractor in accordance with various embodiments. In this case, the skin tool head support 130-*j* may be configured to support the skin tool 125-*b*. This may include the use of coupler 210-*a* such as a wing nut and bolt other mechanism for connecting the skin tool 125-*b* to the skin tool head support 130-*j*. In this example, the skin tool head support 130-*j* includes an angled portion with respect to the main portion of the skin tool head support 130-*j*.

Figure 3A:
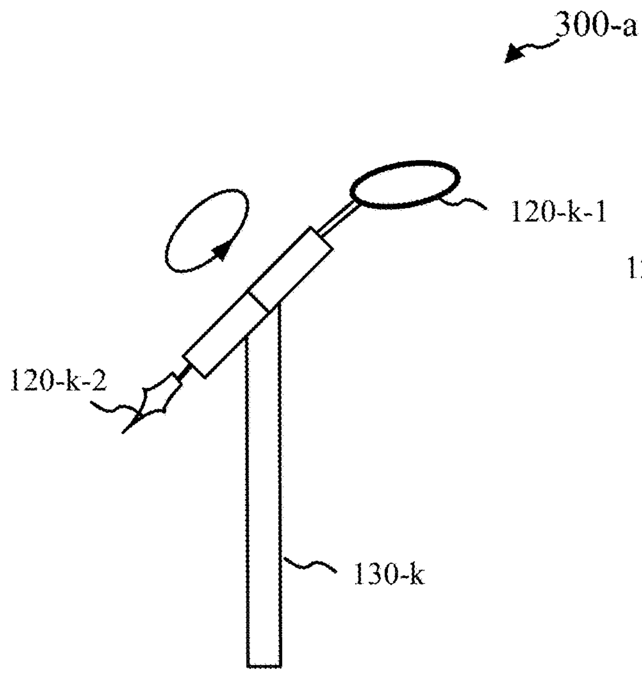
FIGS. 3A, 3B, and 3C show configurations to facilitate skin care in accordance with various embodiments.
Figure 3B:
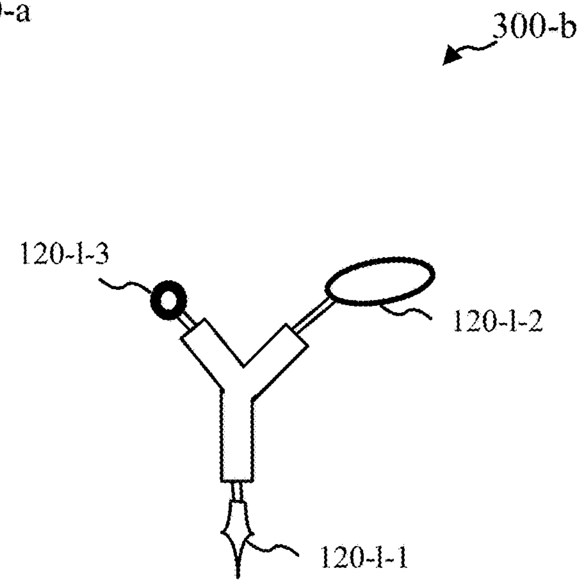
Figure 3C:
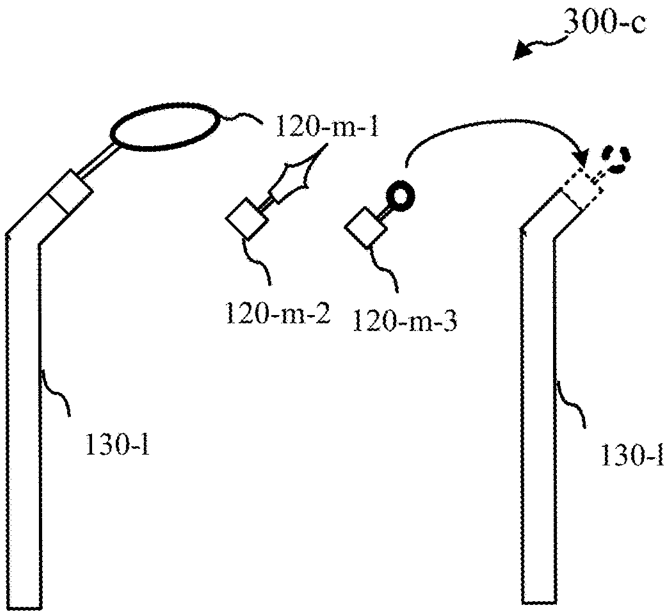

FIGS. 3A, 3B, and 3C show several different configurations that may allow for a skin tool head support to be configured to couple with a variety of different skin tool head portions. For example, FIG. 3A shows a configuration 300-*a* where skin tool head support 130-*k* may be coupled with multiple skin tool head portions 120-*k*-1 and 120-*k*-2 in accordance with various embodiments. In this example, the skin tool head portions 120-*k*-1 and 120-*k*-2 are coupled with each other and the skin tool head support 130-*k* such that the skin tool head portions 120-*k*-1 and 120-*k*-2 may be rotated with respect to the skin tool head support 130-*k*. FIG. 3B then shows a configuration 300-*b* that includes multiple skin tool head portions 120-1-1, 120-1-2, and 120-1-3 in accordance with various embodiments. This multiple skin tool head portion may be coupled with a kin tool head support. The configurations 300-*a* and/or 300-*b* may facilitate displacing skin tool head portion 120 from a first position to a second position. FIG. 3C shows a configuration 300-*c* skin tool head support 130-1 is configured to couple with a variety of different skin tool head portions 120-*m*-1, 120-*m*-2, 120-*m*-3 in accordance with various embodiments. These skin tool head portions 120-*m* may be coupled with the skin tool head support 130-1 utilizing different coupling components, such as magnets, threaded portion, and/or other mechanical couplings.

Figure 4A:
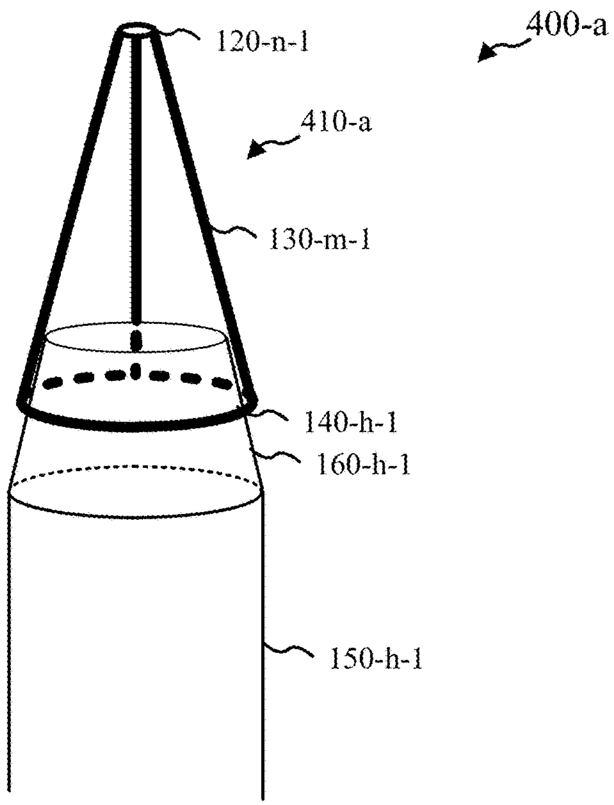
FIGS. 4A and 4B show systems to facilitate skin care in accordance with various embodiments.
Figure 4B:
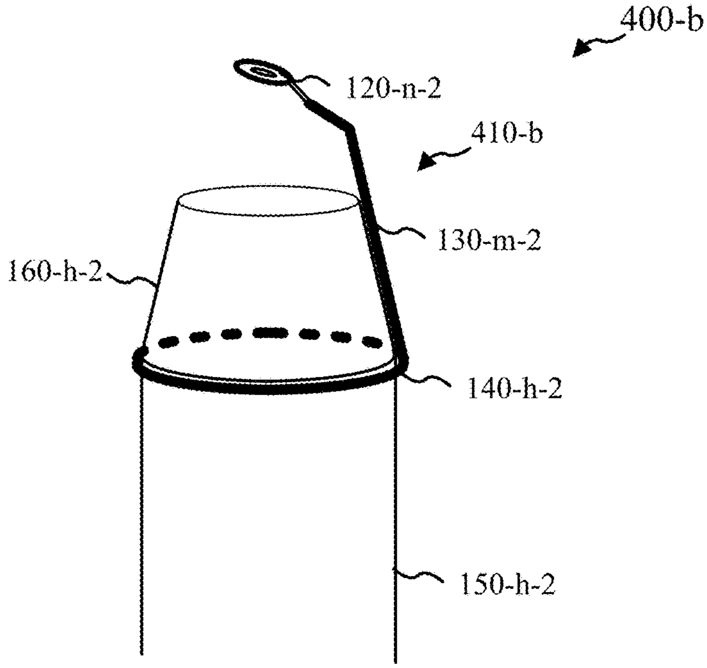

FIG. 4A and FIG. 4B show additional examples of systems 400-*a* and 400-*b*, respectively, to facilitate skin care in accordance with various embodiments. Systems 400-*a* and 400-*b* may be examples of system 100 of FIG. 1A. Systems 400-*a* and 400-*b* may include devices 410-*a* and 410-*b*, respectively, to facilitate skin care. Devices 400-*a* and 400-*b* may be examples of device 100 of FIG. 1A. The device 410-*a* may include multiple aspects such as a skin tool head portion 120-*n*-1, a skin tool head support 130-*m*-1 that may be coupled with the skin tool head portion 120-*n*-1, and/or a portable microscope connector 140-*h*-1 that may be configured to couple a portable microscope 150-*h*-1 with the skin tool head support 140-*h*-1. Systems 400-*a* is also shown with a spacer 160-*h*-1 that may be coupled with portable microscope 150-*h*-1. The skin tool head portion 120-*n*-1 may include a variety of different skin tools; in this example, the skin tool head portion 120-*n*-1 is shown as a comedone extractor, though other skin tools may be utilized. Similarly, the device 410-*b* may include multiple aspects such as a skin tool head portion 120-*n*-2, a skin tool head support 130-*m*-2 that may be coupled with the skin tool head portion 120-*n*-2, and/or a portable microscope connector 140-*h*-2 that may be configured to couple a portable microscope 150-*h*-2 with the skin tool head support 140-*h*-2. Systems 400-*b* is also shown with a spacer 160-*h*-2 that may be coupled with portable microscope 150-*h*-2. The skin tool head portion 120-*n*-2 may include a variety of different skin tools; in this example, the skin tool head portion 120-*n*-2 is shown as a comedone extractor, though other skin tools may be utilized. For devices 410-*a* and/or 410-*b*, the portable microscope connectors 140-*h*-1 and/or 140-*h*-2 may be configured to slide over the spacers 160-*h*-1 and/or 160-*h*-2 respectively and then couple with the respective microscope 150-*h*-1 and/or 150-*h*-2. Device 400-*a* may couple with portable microscope 150-*h*-1 through coupling with spacer 160-*h*-1, while device 400-*b* may couple with portable microscope 150-*h*-2 through coupling with the portable microscope 150-*h*-2 itself. Skin tool head support 130-*m*-1 may have multiple parts, such as three supports, while skin tool head support 130-*m*-2 may include a single part, or single support, though in other embodiments, these elements may include different numbers of parts.

Figure 5A:
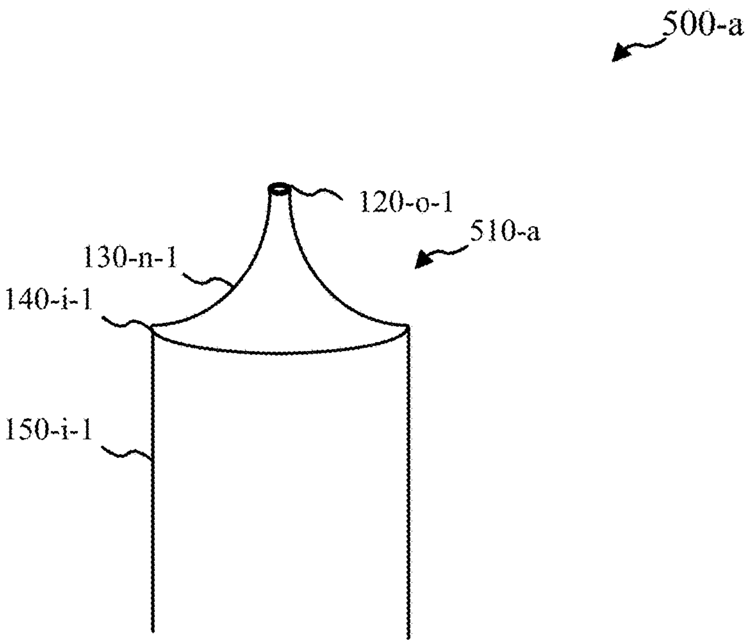
FIGS. 5A, 5B, and 5C show systems to facilitate skin care in accordance with various embodiments.
Figure 5B:
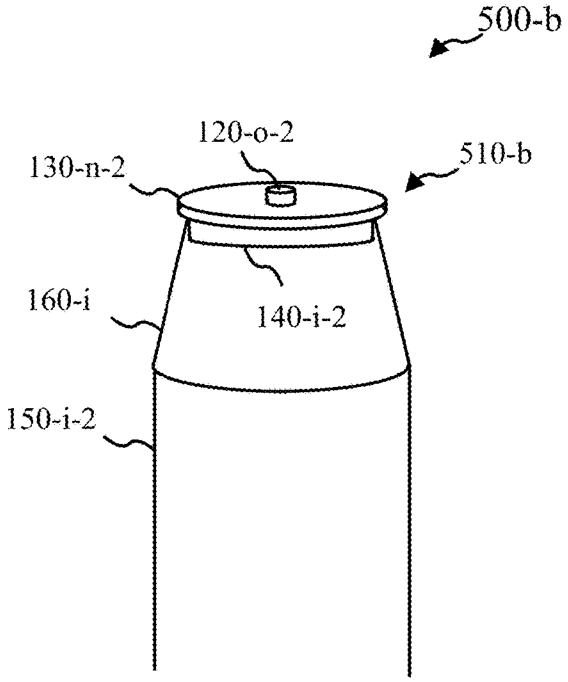
Figure 5C:
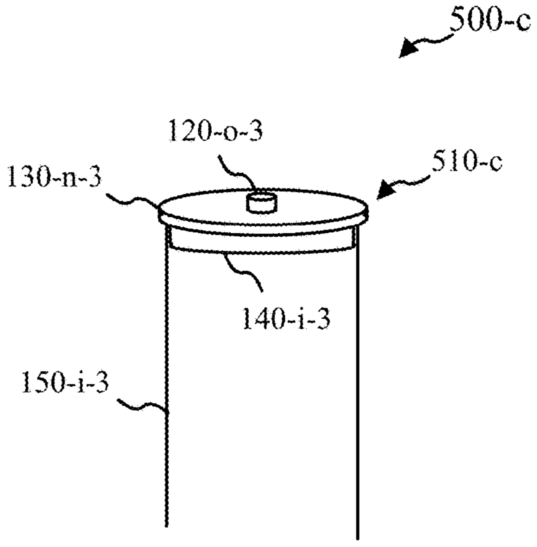

FIG. 5A, FIG. 5B, and FIG. 5C show additional examples of systems 500-*a*, 500-*b*, and 500-*c*, respectively, to facilitate skin care in accordance with various embodiments. Systems 500-*a*, 500-*b*, and 500-*c* may be examples of system 100 of FIG. 1A. Systems 500-*a*, 500-*b*, and 500-*c* may include devices 510-*a*, 510-*b*, and 510-*c*, respectively, to facilitate skin care. Devices 500-*a*, 500-*b*, and 500-*c* may be examples of device 100 of FIG. 1A.

The device 510-*a* may include multiple aspects such as a skin tool head portion 120-*o*-1, a skin tool head support 130-*n*-1 that may be coupled with the skin tool head portion 120-*o*-1, and/or a portable microscope connector 140-*i*-1 that may be configured to couple a portable microscope 150-*i*-1 with the skin tool head support 130-*n*-1. In this example, skin tool head portion 120-*o*-1 may be integrated with skin tool head support 130-*n*-1, which may be a spacer, such as spacers 160 shown herein. The skin tool head portion 120-*o*-1 may be configured as an aperture as part of the skin tool head support 130-*n*-1. The skin tool head portion 120-*o*-1 may be sized for comedone extraction or other skin care purposes, for example. The device 510-*b* may include multiple aspects such as a skin tool head portion 120-*o*-2, a skin tool head support 130-*n*-2 that may be coupled with the skin tool head portion 120-*o*-2, and/or a portable microscope connector 140-*i*-2 that may be configured to couple a portable microscope 150-*i*-2 with the skin tool head support 130-*n*-2. In this example, skin tool head portion 120-*o*-2 may be integrated with skin tool head support 140-*i*-2 and portable microscope connector 140-*i*-2 such that the portable microscope connector 140-*i*-2 and the skin tool head support 130-*n*-2 work to couple with spacer 160-*i*. The skin tool head portion 120-*o*-2 may be configured as an aperture as part of the skin tool head support 130-*n*-2. The skin tool head portion 120-*o*-2 may be sized for comedone extraction or other skin care purposes, for example. Similarly, device 510-*c* may include multiple aspects such as a skin tool head portion 120-*o*-3, a skin tool head support 130-*n*-3 that may be coupled with the skin tool head portion 120-*o*-3, and/or a portable microscope connector 140-*i*-3 that may be configured to couple a portable microscope 150-*i*-3 with the skin tool head support 130-*n*-3. In this example, skin tool head portion 120-*o*-3 may be integrated with skin tool head support 130-*i*-3 and portable microscope connector 140-*i*-3 such that the portable microscope connector 140-*i*-3 and the skin tool head support 130-*n*-3 work to couple with portable microscope 150-*i*-3. The skin tool head portion 120-*o*-3 may be configured as an aperture as part of the skin tool head support 130-*n*-3. The skin tool head portion 120-*o*-3 may be sized for comedone extraction or other skin care purposes, for example.

Figure 6A:
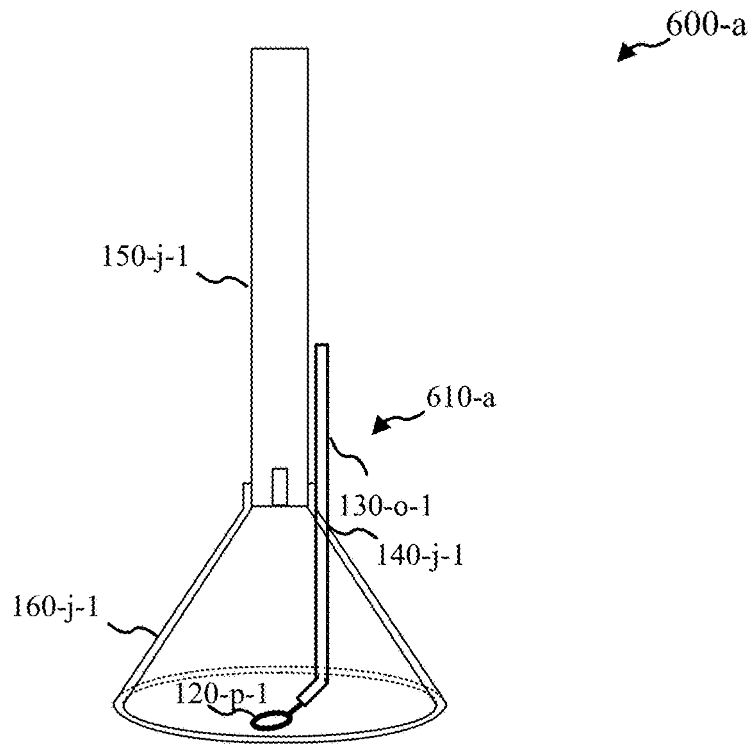
FIGS. 6A, 6B, and 6C show systems to facilitate skin care in accordance with various embodiments.
Figure 6B:
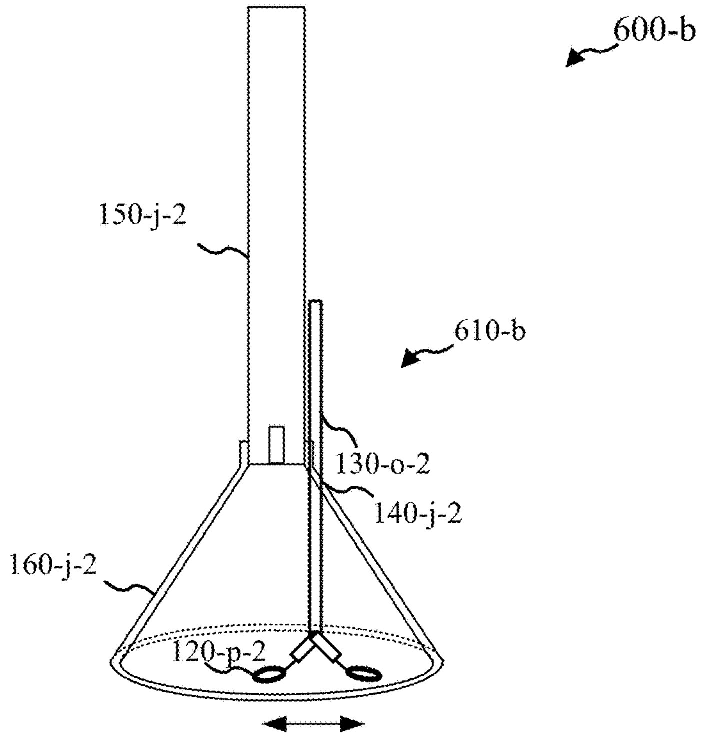
Figure 6C:
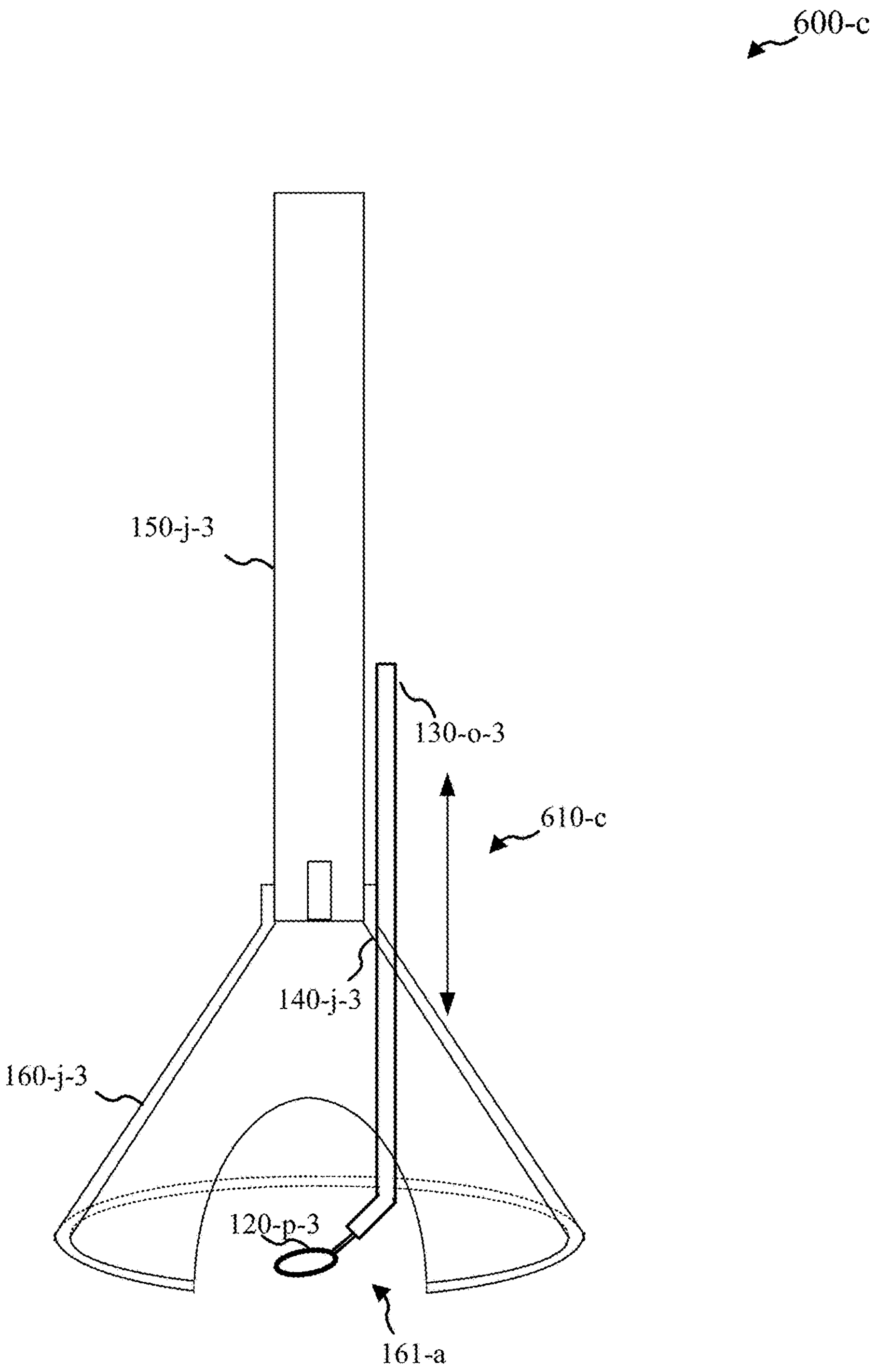

FIG. 6A, FIG. 6B, and FIG. 6C show additional examples of systems 600-*a*, 600-*b*, and 600-*c*, respectively, to facilitate skin care in accordance with various embodiments. Systems 600-*a*, 600-*b*, and 600-*c* may be an examples of system 100 of FIG. 1A. Systems 600-*a*, 600-*b*, and 600-*c* may include devices 610-*a*, 610-*b*, and 610-*c*, respectively, to facilitate skin care. Devices 600-*a*, 600-*b*, and 600-*c* may be examples of device 100 of FIG. 1A The device 610-*a* may include multiple aspects such as a skin tool head portion 120-*p*-1, a skin tool head support 130-*o*-1 that may be coupled with the skin tool head portion 120-*p*-1, and/or a portable microscope connector 140-*j*-1 that may be configured to couple a portable microscope 150-*j*-1 with the skin tool head support 130-*o*-1. System 600-*a* also includes a spacer 160-*j*-1. The skin tool head support 130-*o*-1 may be configured to facilitate displacing the skin tool head portion 120-*p*-1 from a first position to a second position. In this case, the skin tool head support 130-*o*-1 may be configured to be displaced along an axis parallel to an axis of the portable microscope 150-*j*-1. Similarly, the device 610-*b* may include multiple aspects such as a skin tool head portion 120-*p*-2, a skin tool head support 130-*o*-2 that may be coupled with the skin tool head portion 120-*p*-2, and/or a portable microscope connector 140-*j*-2 that may be configured to couple a portable microscope 150-*j*-2 with the skin tool head support 130-*o*-2. The skin tool head support 130-*o*-2 may be configured to facilitate displacing the skin tool head portion 120-*p*-2 from a first position to a second position. In this case, the skin tool head support 130-*o*-2 may be configured such that the skin tool head portion 120-*p*-2 may be displaced with respect to an axis of the skin tool head support 130-*o*-2. In some cases, this may be achieved through rotating the skin tool head support 130-*o*-2, though other techniques may be utilized. System 600-*b* also may include a spacer 160-*j*-2. The device 610-*c* may include multiple aspects such as a skin tool head portion 120-*p*-3, a skin tool head support 130-*o*-3 that may be coupled with the skin tool head portion 120-*p*-3, and/or a portable microscope connector 140-*j*-3 that may be configured to couple a portable microscope 150-*j*-3 with the skin tool head support 130-*o*-3. The skin tool head support 130-*o*-3 may be configured to facilitate displacing the skin tool head portion 120-*p*-3 from a first position to a second position. In this case, the skin tool head support 130-*o*-3 may be configured to be displaced along an axis parallel to an axis of the portable microscope 150-*j*-3. System 600-*c* also may include a spacer 160-*j*-3, in this case with an aperture 161-*a*, which may facilitate the use of another skin tool (not shown).

Figure 7A:
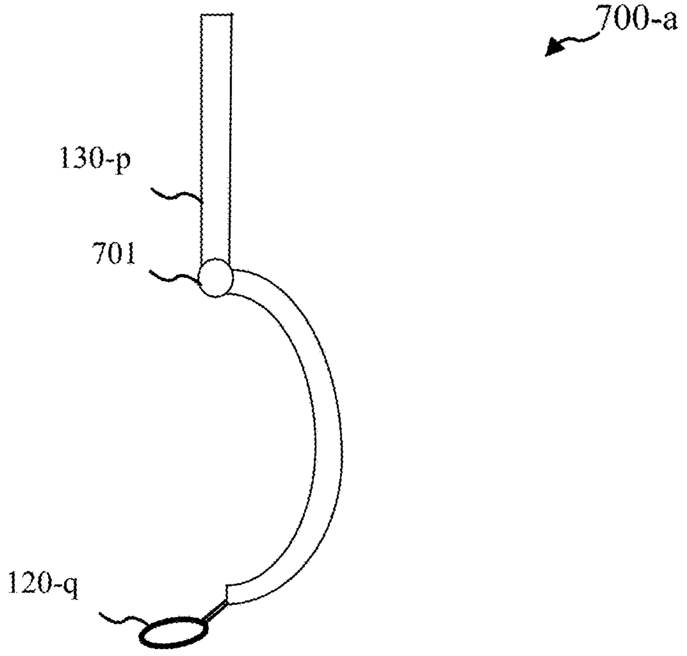
FIGS. 7A and 7B show configurations to facilitate skin care in accordance with various embodiments.
Figure 7B:
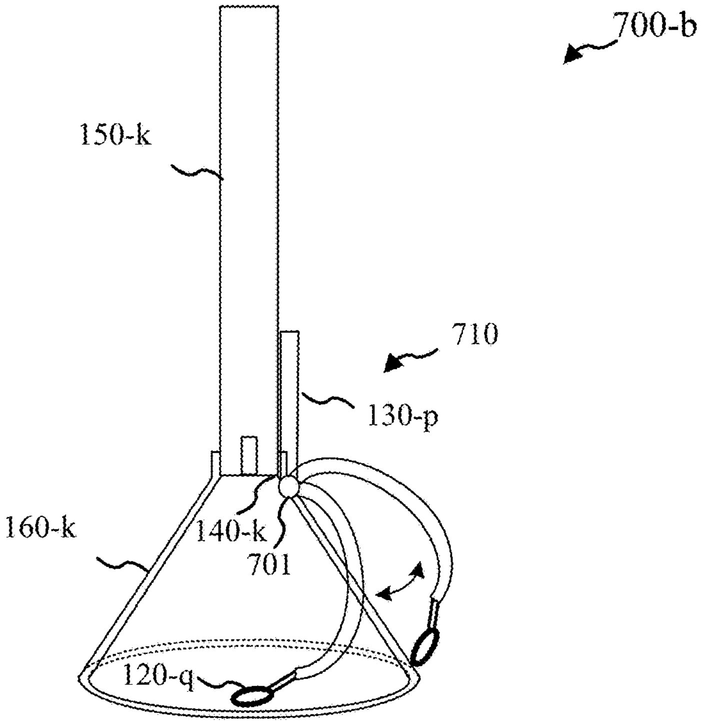

Turning now to FIGS. 7A and 7B, other examples of utilizing a skin tool head support configured to facilitate displacing a skin tool head portion are provided. FIG. 7A shows a configuration 700-*a* that includes a skin tool head portion 120-*q* and a skin tool head portion support 130-*p*, where the skin tool head portion support includes a pivot point 701 to facilitate displacing the lower portion of the skin tool head portion support 130-*p* and the skin tool head portion 120-*q* in accordance with various embodiments. FIG. 7B shows a system 700-*b* that utilizes these components as configured as a device 710 to facilitate skin care, showing the possible displacement in accordance with various embodiments. Device 710 may be an example of device 110 of FIG. 1A. System 700-*b* also shows a portable microscope 150-*k*, a portable microscope connector 140-*k*, and a spacer 160-*k*. In some cases, the spacer 160-*k* may include a channel to facilitate the displacement of the displacing the lower portion of the skin tool head portion support 130-*p* and the skin tool head portion 120-*q*.

Figure 8A:
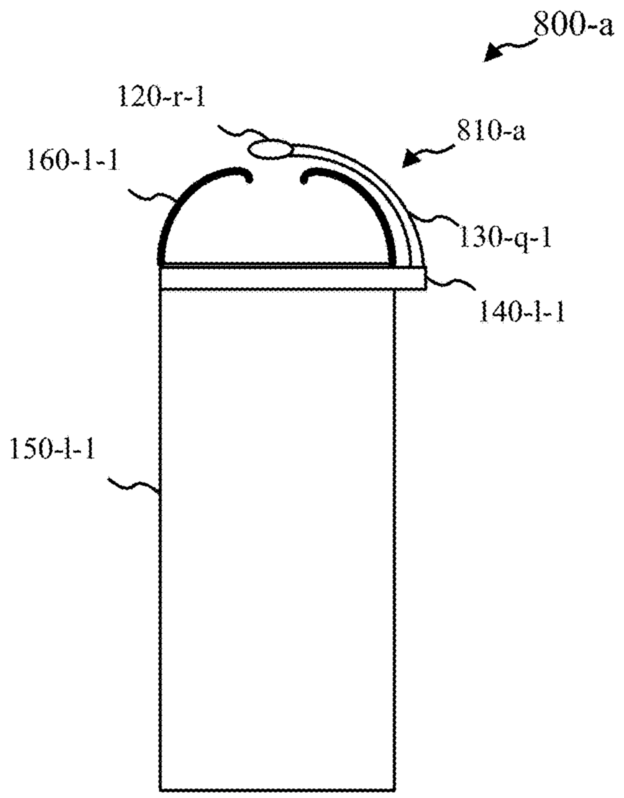
FIGS. 8A, 8B, and 8C show systems to facilitate skin care in accordance with various embodiments.
Figure 8B:
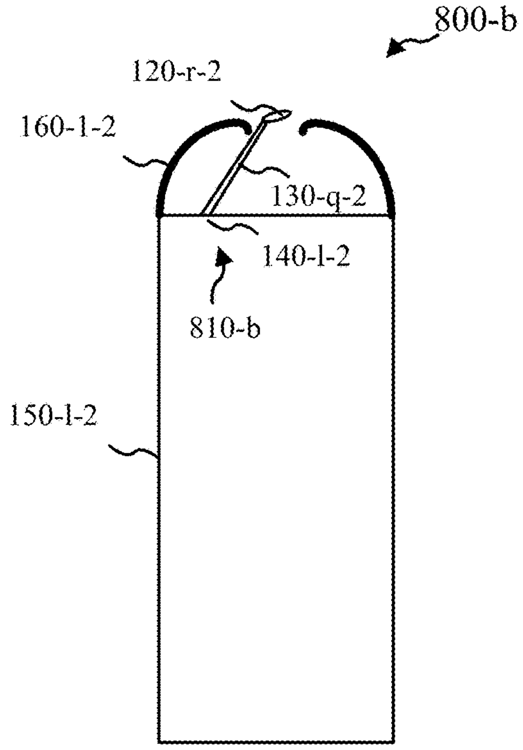
Figure 8C:
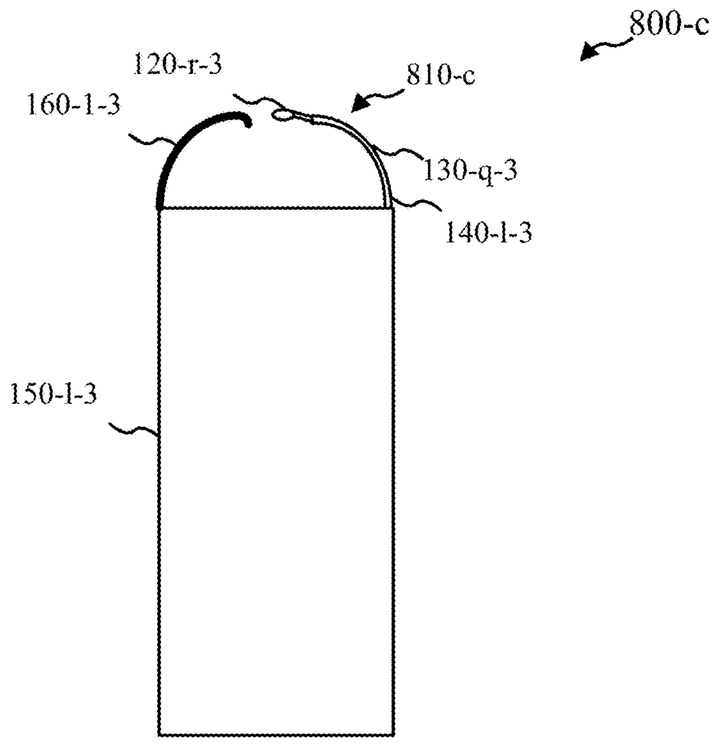

FIG. 8A, FIG. 8B, and FIG. 8C show additional examples of systems 800-*a*, 800-*b*, and 800-*c*, respectively, to facilitate skin care in accordance with various embodiments. Systems 800-*a*, 800-*b*, and 800-*c* may be an examples of system 100 of FIG. 1A. Systems 800-*a*, 800-*b*, and 800-*c* may include devices 810-*a*, 810-*b*, and 810-*c*, respectively, to facilitate skin care. Devices 800-*a*, 800-*b*, and 800-*c* may be examples of device 110 of FIG. 1A.

The device 810-*a* may include multiple aspects such as a skin tool head portion 120-*r*-1, a skin tool head support 130-*q*-1 that may be coupled with the skin tool head portion 120-*r*-1, and/or a portable microscope connector 140-1-1 that may be configured to couple a portable microscope 150-1-1 with the skin tool head support 130-*q*-1. System 800-*a* also includes a spacer 160-1-1. Spacer 160-1-1 may include a rounded edge. In this example, the skin tool head portion 120-*r*-1 and a skin tool head support 130-*q*-1 may be configured to fit outside the spacer 160-1-1. The device 810-*b* may include multiple aspects such as a skin tool head portion 120-*r*-2, a skin tool head support 130-*q*-2 that may be coupled with the skin tool head portion 120-*r*-2, and/or a portable microscope connector 140-1-2 that may be configured to couple a portable microscope 150-1-2 with the skin tool head support 130-*q*-2. System 800-*b* also includes a spacer 160-1-2. Spacer 160-1-2 may include a rounded edge. In this example, the skin tool head portion 120-*r*-2 and a skin tool head support 130-*q*-2 may be configured to fit inside the spacer 160-1-2. The device 810-*c* may include multiple aspects such as a skin tool head portion 120-*r*-3, a skin tool head support 130-*q*-3 that may be coupled with the skin tool head portion 120-*r*-3, and/or a portable microscope connector 140-1-3 that may be configured to couple a portable microscope 150-1-3 with the skin tool head support 130-*q*-3. System 800-*c* also includes a spacer 160-1-3. Spacer 160-1-3 may include a rounded edge. In this example, the skin tool head portion 120-*r*-3 and a skin tool head support 130-*q*-3 may be integrated as part of the spacer 160-1-3.

In some embodiments, the spacer 160-1-2 may be coupled with or includes a compressible structure or portion positioned between the spacer 160-*i*-2 and the portable microscope 150-1-2. The compressible structure may be configured to preclude the skin tool head portion 120-*r*-2 from contacting a portion of skin when the compressible structure is in an uncompressed state and to allow the skin tool head portion 120-*r*-2 to contact the portion of skin when the compressible structure is in a compressed state. The compressible structure may include a spring-loaded platform in some cases. The compressible structure may be configured out of other compressible materials such as flexible plastic and/or rubber. Some embodiments, for example, may include a compressible cuff.

Figure 9:
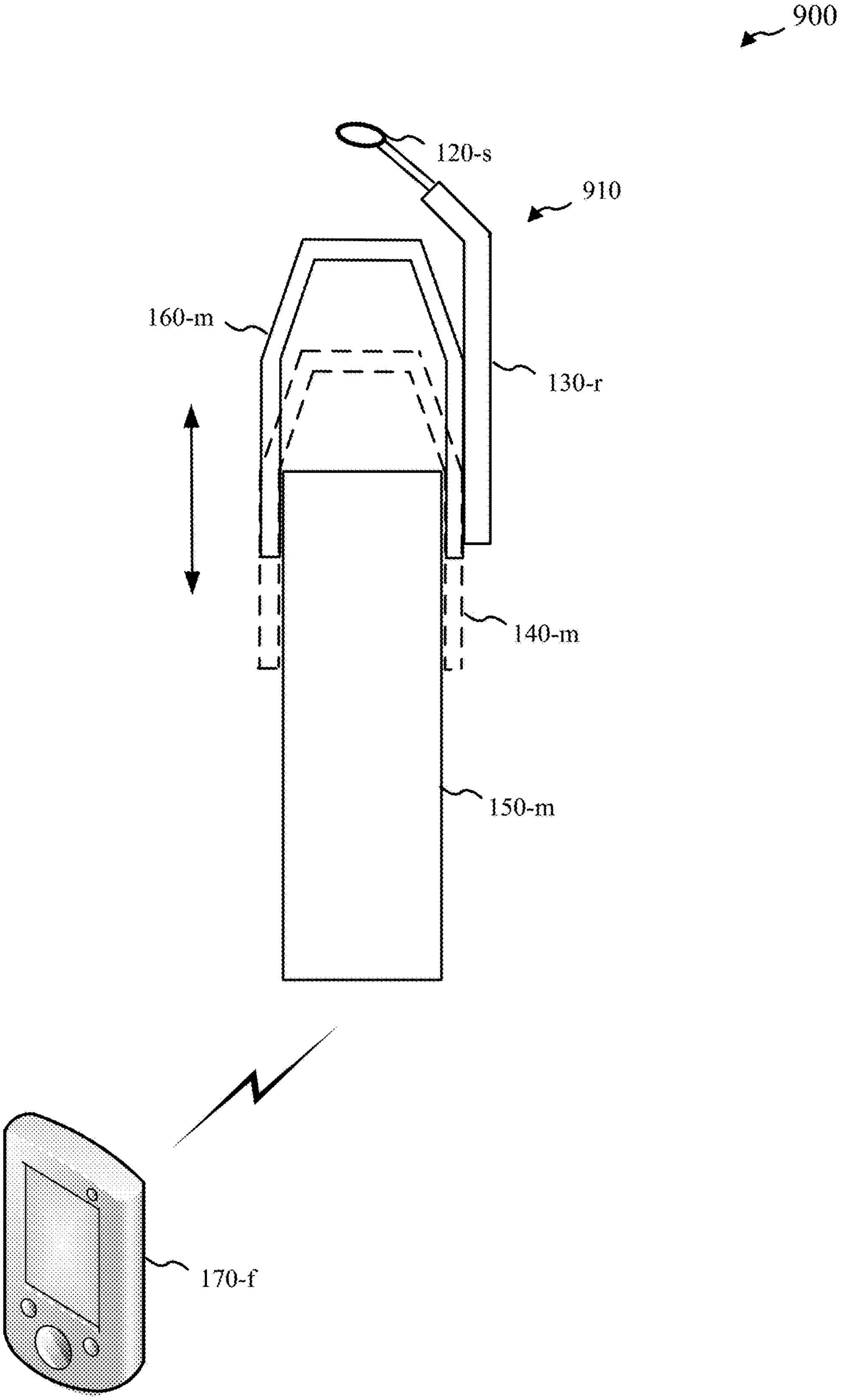
FIG. 9 shows a system to facilitate skin care in accordance with various embodiments.

FIG. 9 shows a specific example of system 900 to facilitate skin care is provided in accordance with various embodiments. System 900 may be an example of system 100 of FIG. 1A. System 900 may include a device 910, in particular, to facilitate skin care. Device 910 may be an example of device 110 of FIG. 1A. The device 910 may include multiple aspects such as a skin tool head portion 120-*s*, a skin tool head support 130-*r* that may be coupled with the skin tool head portion 120-*s*, and/or a portable microscope connector 140-*m* that may be configured to couple a portable microscope 150-*m* with the skin tool head support 130-*r*. In this example, device 900 may be configured to transmit information to a monitor 170-*f* wireless, though some embodiments may utilize a physical transmission medium. Device 910 may include a spacer 160-*m* that may be coupled with the skin tool head support 130-*r* such that these elements may move together. Spacer 160-*m* may be configured to slide or otherwise move along an outer surface of the portable microscope 150-*m*.

In some cases, the skin tool head support 130-*n* along with the spacer 160-*m* may be configured to move such that at least a portion of the skin tool head portion 120-*s* is positioned within a field of view of the portable microscope 150-*m* when the portable microscope connector 140-*m* is coupled with the portable microscope 150-*m*. The field of view of the portable microscope 150-*m* may include at least within a focal plane or at a focal point of the portable microscope 150-*m*. The skin tool head portion 120-*s* may include a variety of different skin tools; in this example, the skin tool head portion 120-*s* is shown as a comedone extractor, though other skin tools may be utilized. In some cases, the spacer 160-*m* may be configured with a compressible structure to preclude the skin tool head portion 120-*s* from contacting a portion of skin when the compressible structure is in an uncompressed state and to allow the skin tool head portion 120-*s* to contact the portion of skin when the compressible structure is in a compressed state. The compressible structure may include a spring-loaded platform in some cases. The compressible structure may be configured out of other compressible materials such as flexible plastic and/or rubber. Some embodiments, for example, may include a compressible cuff.

Figure 10:
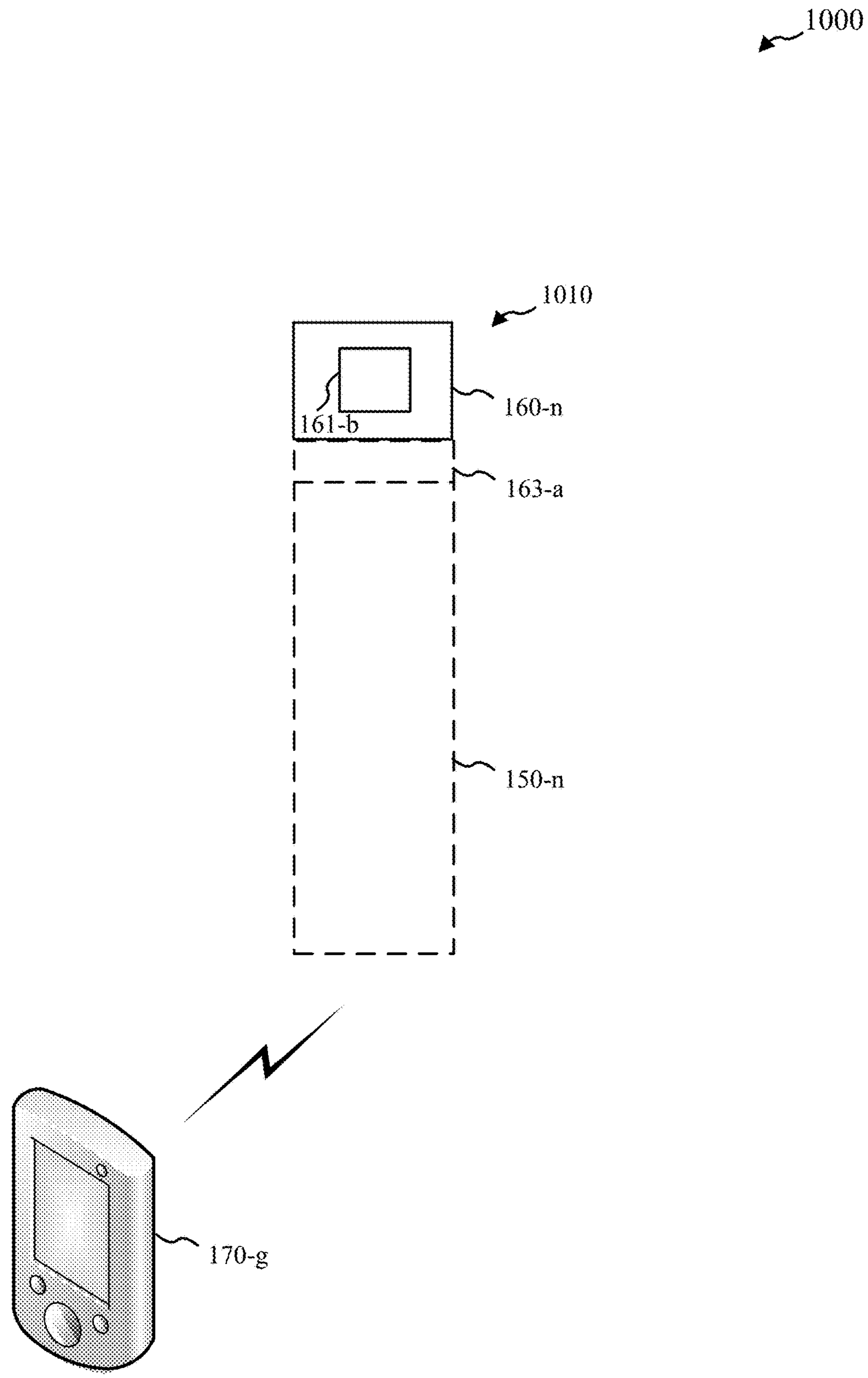
FIG. 10 shows a system to facilitate skin care in accordance with various embodiments.

Turning now to FIG. 10, a system 1000 is shown to facilitate skin care in accordance with various embodiments. System 1000 may include a device 1010, in particular, to facilitate skin care. Device 1010 may include a spacer 160-*n* configured to couple with a portable microscope 150-*n*. The spacer 160-*n* may include at least one aperture 161-*b* configured to facilitate the use of a skin tool. System 1000 may include a monitor 170-*g*. Portable microscope 150-*n* may be configured to transmit information to monitor 170-*g*, which may include a computer monitor, tablet, smart device, or other device that includes a visual screen, merely by way of example. This information may include visual information that may be transmitted wirelessly or over physical transmission media.

In some embodiments, the spacer 160-*n* may be configured to telescope with respect to a body of the portable microscope 150-*n*; an example of this may be shown in system 900 of FIG. 9. The aperture 161-*b* may be a cutaway of the spacer 160-*n*. In some embodiments, the aperture 161-*b* may include a channel extending from a first portion of the spacer 160-*n* to a second portion of the spacer 160-*n*. In some embodiments, the aperture 161-*b* may extend through a body portion of the spacer 160-*n* between a first edge of the spacer 160-*n* and a second edge of the spacer 160-*n*. In some embodiments, the aperture 161-*b* extends from a first edge of the spacer 160-*n* distal with respect to the portable microscope 150-*n*. In some embodiments, the aperture 161-*b* may extend from a second edge of the spacer 160-*n* proximal with respect to the portable microscope 150-*n*. In some embodiments, the spacer 160-*n* may include a lens protector for the portable microscope 150-*n*.

Some embodiments include a compressible structure 163-*a* coupled with the spacer 160-*n*. The compressible structure 163-*a* may be integrated with the spacer 160-*n*, in some cases, or may be a separate component coupled with the spacer 160-*n*. The compressible structure 163-*a* may be configured to be positioned between the spacer and the portable microscope. The compressible structure 163-*a* may include a spring-loaded platform in some cases. The compressible structure 163-*a* coupled with the spacer may be configured to preclude the skin tool from contacting a portion of skin when the compressible structure is in an uncompressed state and to allow the skin tool to contact the portion of skin when the compressible structure is in a compressed state. The compressible structure 163-*a* may be configured out of other compressible materials such as flexible plastic and/or rubber. Some embodiments, for example, may include a compressible cuff.

Figure 11A:
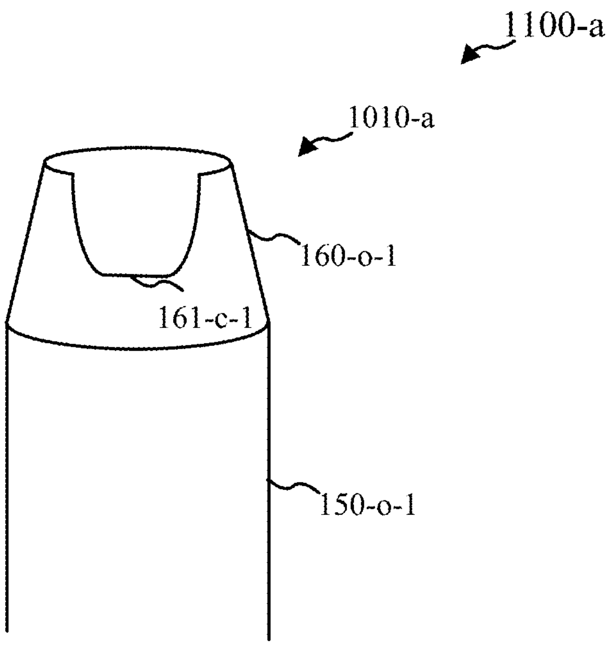
FIGS. 11A and 11B show systems to facilitate skin care in accordance with various embodiments.
Figure 11B:
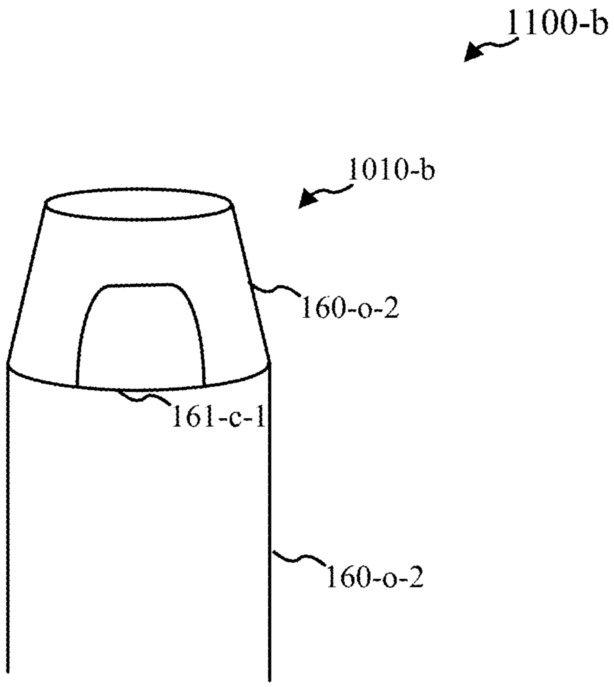

For example, FIG. 11A and FIG. 11B show systems 1100-*a* and 1100-*b*, respectively, to facilitate skin care in accordance with various embodiments. System 1100-*a* and/or system 1100-*b* may be examples of system 1000 of FIG. 10. System 1100-*a* may include a device 1010-*a*, in particular, to facilitate skin care. Device 1010-*a* may be an example of device 1010 of FIG. 10. Device 1010-*a* may include a spacer 160-*o*-1 configured to couple with a portable microscope 150-*o*-1. The spacer 160-*o*-1 may include at least one aperture 161-*c*-1 configured to facilitate the use of a skin tool. The aperture 161-*c*-1 may extend from a first edge of the spacer 160-*o*-1 distal with respect to the portable microscope 150-*o*-1. System 1100-*b* may include a device 1010-*b*, in particular, to facilitate skin care. Device 1010-*b* may be an example of device 1010 of FIG. 10. Device 1010-*b* may include a spacer 160-*o*-2 configured to couple with a portable microscope 150-*o*-2. The spacer 160-*o*-2 may include at least one aperture 161-*c*-2 configured to facilitate the use of a skin tool. The aperture 161-*c*-2 may extend from a second edge of the spacer 160-*o*-2 proximal with respect to the portable microscope 150-*n*-2.

Figure 12:
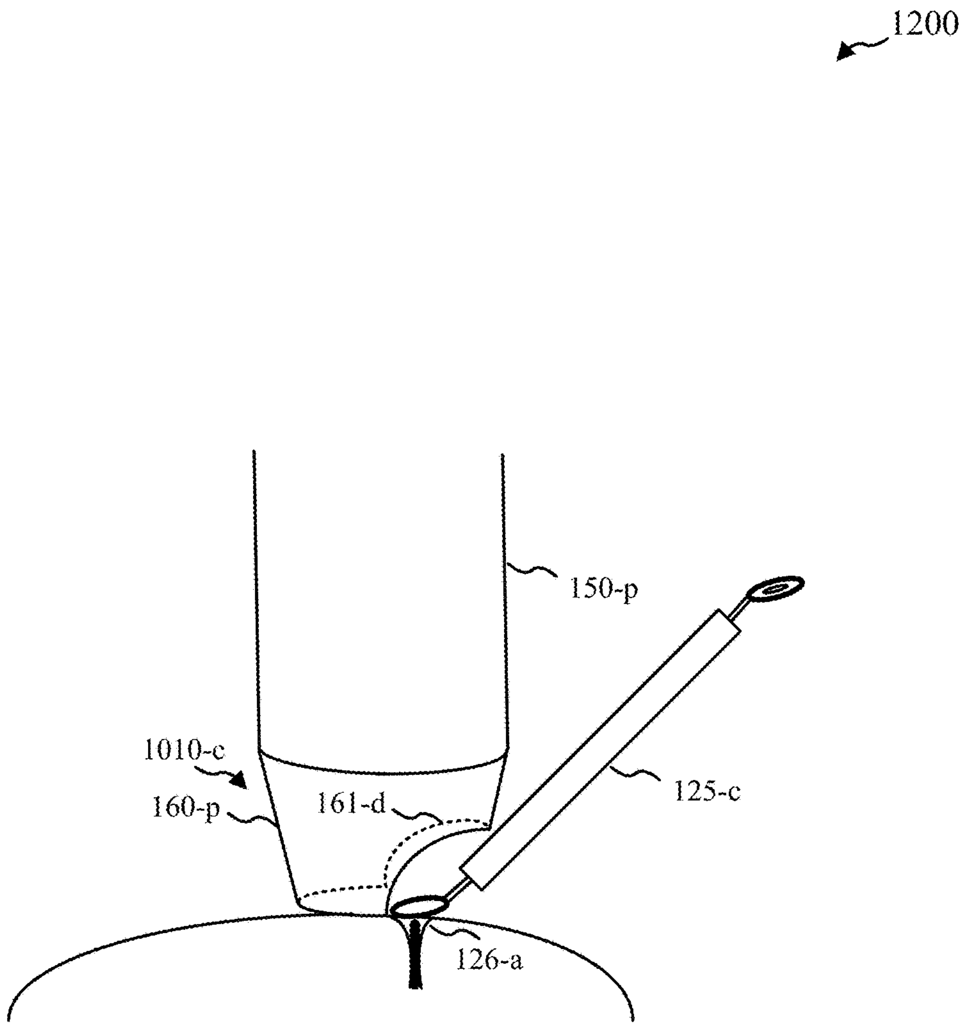
FIG. 12 shows a system to facilitate skin care in accordance with various embodiments.

FIG. 12 shows a system 1200 to facilitate skin care in accordance with various embodiments. System 1200 may be an example of system 1000 of FIG. 10. System 1200 may include a device 1010-*c*, in particular, to facilitate skin care. Device 1010-*c* may be an example of device 1010 of FIG. 10. Device 1010-*c* may include a spacer 160-*p* configured to couple with a portable microscope 150-*p*. The spacer 160-*p* may include at least one aperture 161-*d* configured to facilitate the use of a skin tool 125-*c* to reach a skin site 126-*a*, which may also include a portion of skin, a comedone, a hair, etc.

Figure 13:
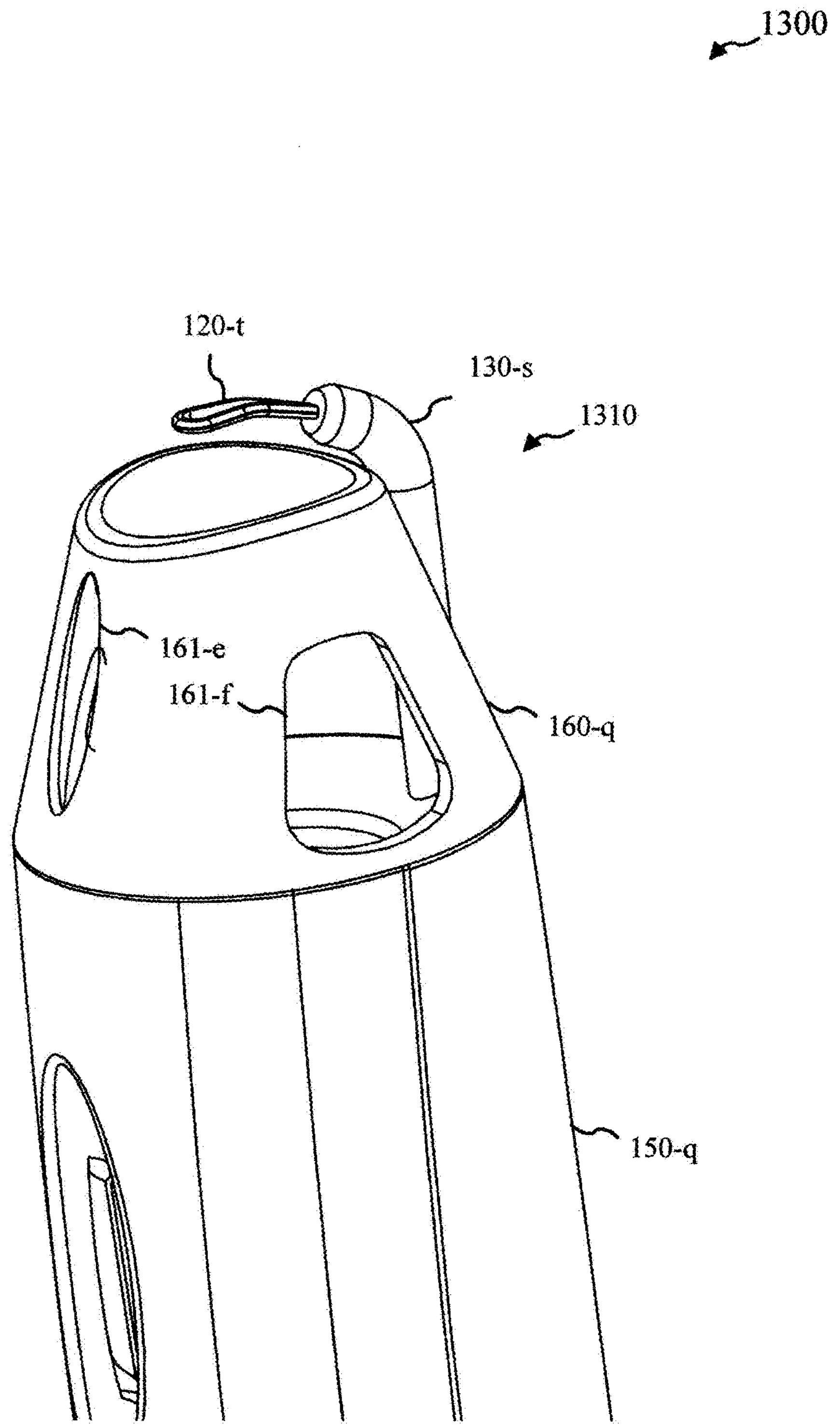
FIG. 13 shows a system to facilitate skin care in accordance with various embodiments.

FIG. 13 shows a specific example of system 1300 to facilitate skin care is provided in accordance with various embodiments. System 1300 may be an example of system 100 of FIG. 1A, for example. System 1300 may include a device 1310, in particular, to facilitate skin care. Device 1310 may be an example of device 110 of FIG. 1A. The device 1310 may include multiple aspects such as a skin tool head portion 120-*t*, a skin tool head support 130-*s* that may be coupled with the skin tool head portion 120-*t*; the support 130-*s* may be configured to couple with a portable microscope 150-*q*. Device 1310 may include a spacer 160-*q*, which may be coupled with the skin tool head support 130-*s* and/or microscope 150-*q*.

In some cases, the skin tool head support 130-*s* along with the spacer 160-*q* may be configured to move such that at least a portion of the skin tool head portion 120-*t* may be positioned within a field of view of the portable microscope 150-*q*. The field of view of the portable microscope 150-*q* may include at least within a focal plane or at a focal point of the portable microscope 150-*q*. The skin tool head portion 120-*t* may include a variety of different skin tools; in this example, the skin tool head portion 120-*t* is shown as a comedone extractor, though other skin tools may be utilized. Spacer 160-*q* may be one or more apertures 161-*e*, 161-*f*. The spacer 160-*q* with one or more apertures 161-*e*, 161-*f* may facilitate the use of two or more skin care tools in some cases.

Figure 14:
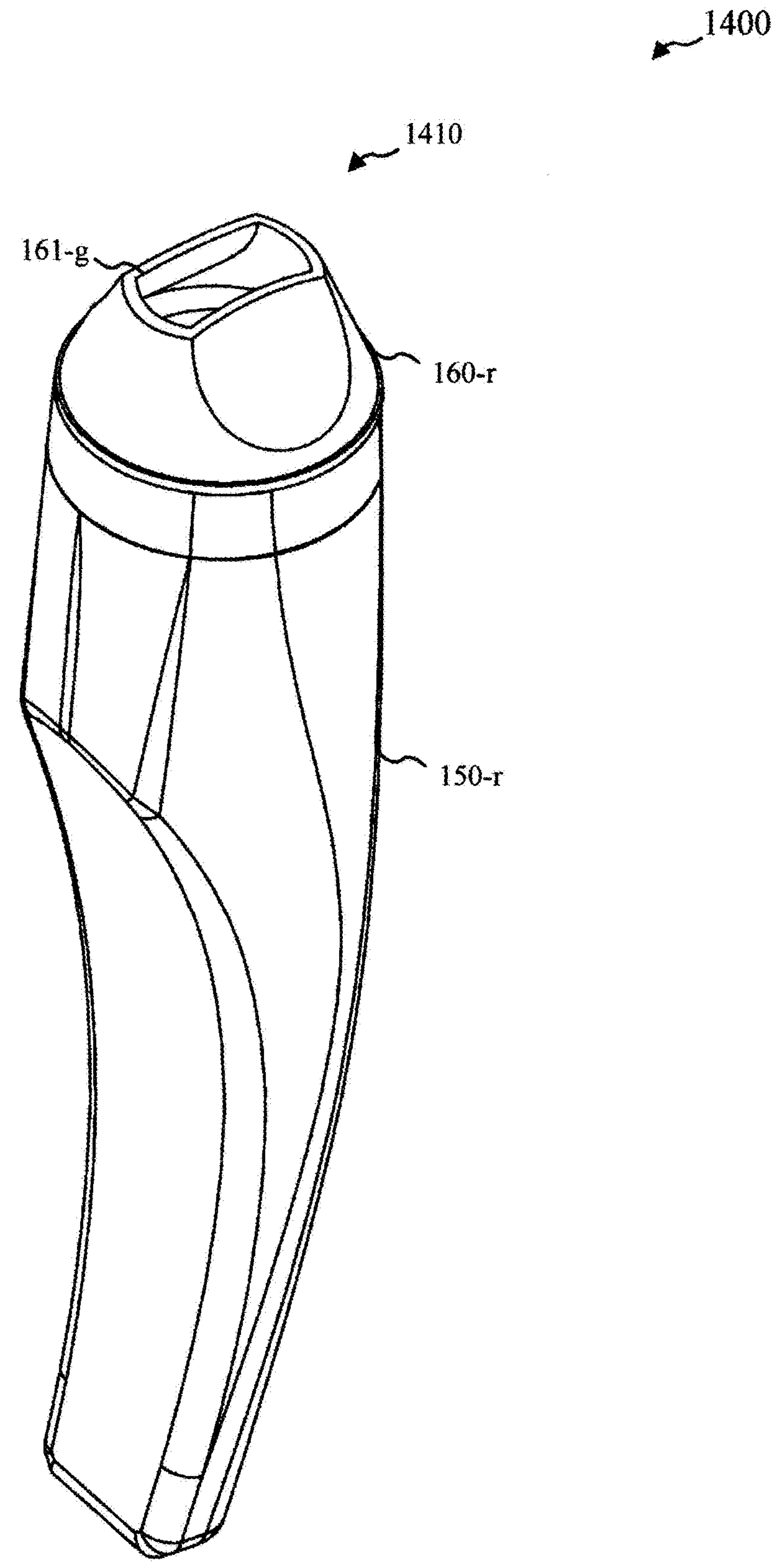
FIG. 14 shows a system to facilitate skin care in accordance with various embodiments.

FIG. 14 shows a specific example of system 1400 to facilitate skin care is provided in accordance with various embodiments. System 1400 may be an example of system 1000 of FIG. 10, for example. System 1400 may include a device 1410, in particular, to facilitate skin care. Device 1410 may be an example of device 1010 of FIG. 10. Device 1410 may include a spacer 160-*r* configured to couple with a portable microscope 150-*r*. The spacer 160-*r* may include at least one aperture 161-*g* configured to facilitate the use of a skin tool and/or viewing of a skin site.

Figure 15:
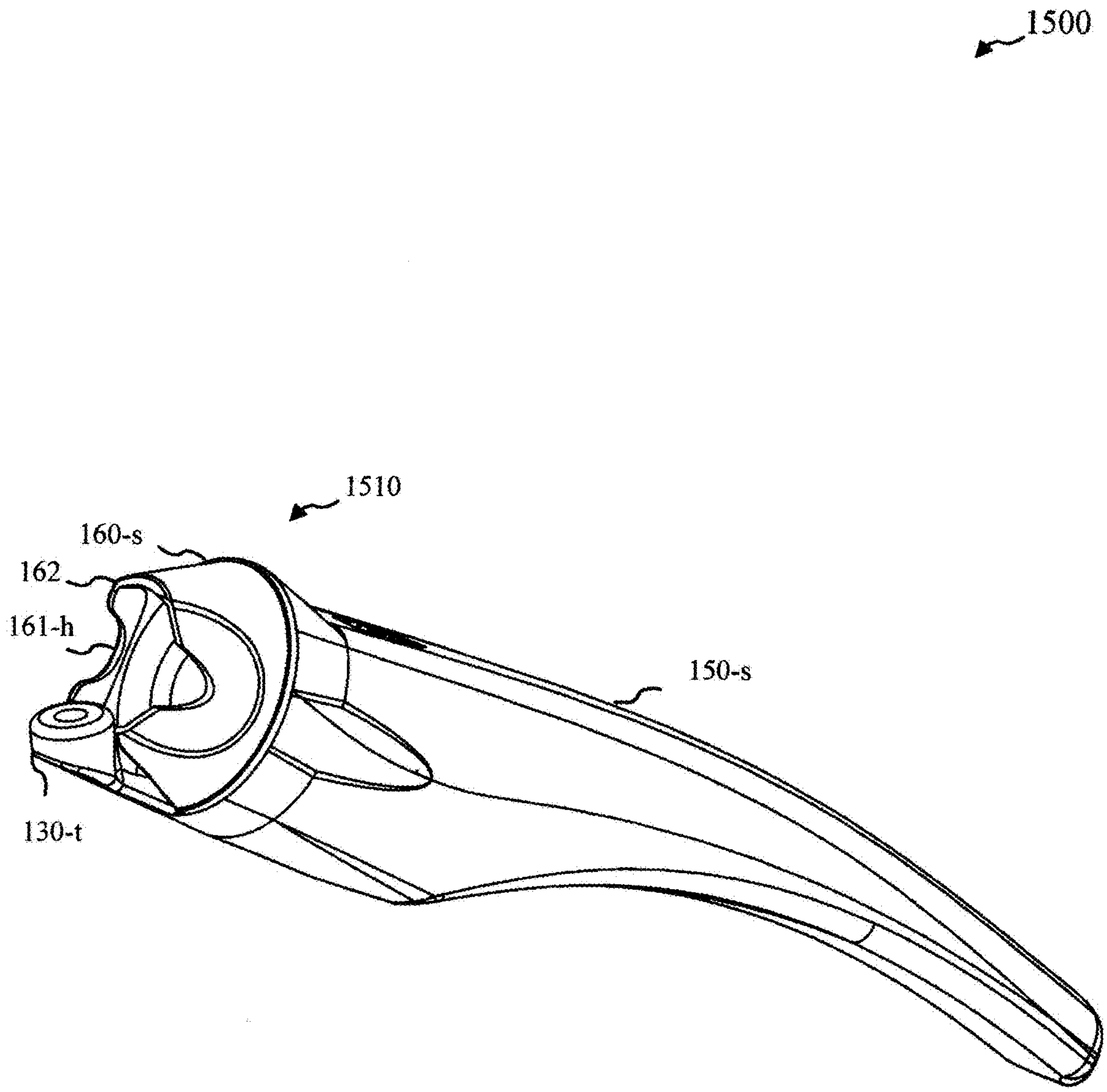
FIG. 15 shows a system to facilitate skin care in accordance with various embodiments.

FIG. 15 shows a specific example of system 1500 to facilitate skin care is provided in accordance with various embodiments. System 1500 may be an example of system 1000 of FIG. 10 and/or system 100 of FIG. 1A, for example. System 1500 may include a device 1510, in particular, to facilitate skin care. Device 1510 may be an example of device 1010 of FIG. 10 and/or device 110 of FIG. 1A. Device 1510 may include a spacer 160-*s* configured to couple with a portable microscope 150-*s*. The spacer 160-*s* may include at least one aperture 161-*h* configured to facilitate the use of a skin tool and/or viewing of a skin site. The spacer 160-*s* may include an edge portion 162 configured to facilitate engage a portion of skin. Device 1510 may also include a skin tool head support 130-*t*.

Figure 16:
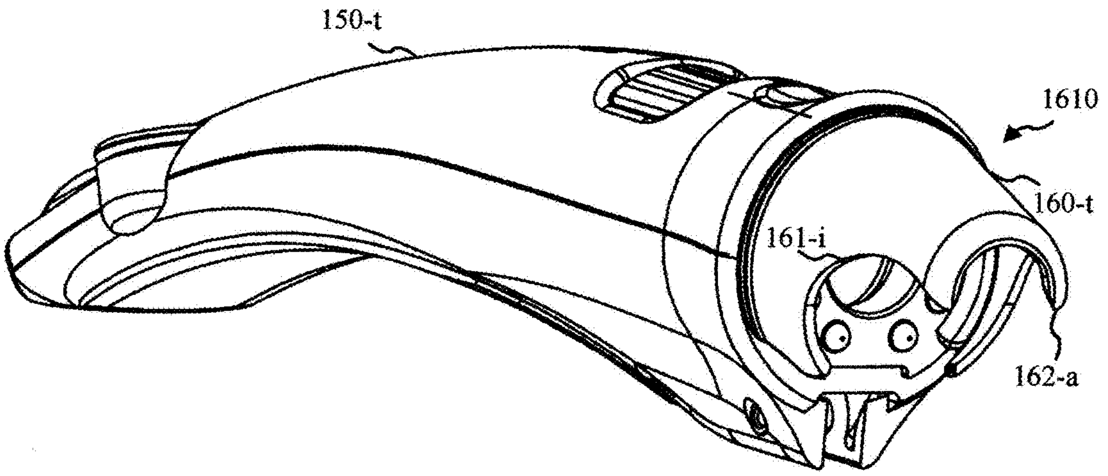
FIG. 16 shows a system to facilitate skin care in accordance with various embodiments.

FIG. 16 shows a specific example of system 1600 to facilitate skin care is provided in accordance with various embodiments. System 1600 may be an example of system 1000 of FIG. 10, for example. System 1600 may include a device 1610, in particular, to facilitate skin care. Device 1610 may be an example of device 1010 of FIG. 10. Device 1610 may include a spacer 160-*t* configured to couple with a portable microscope 150-*t*. The spacer 160-*t* may include at least one aperture 161-*i* configured to facilitate the use of a skin tool and/or viewing of a skin site. The spacer 160-*t* may include an edge portion 162-*a* configured to facilitate engage a portion of skin.

Figure 17A:
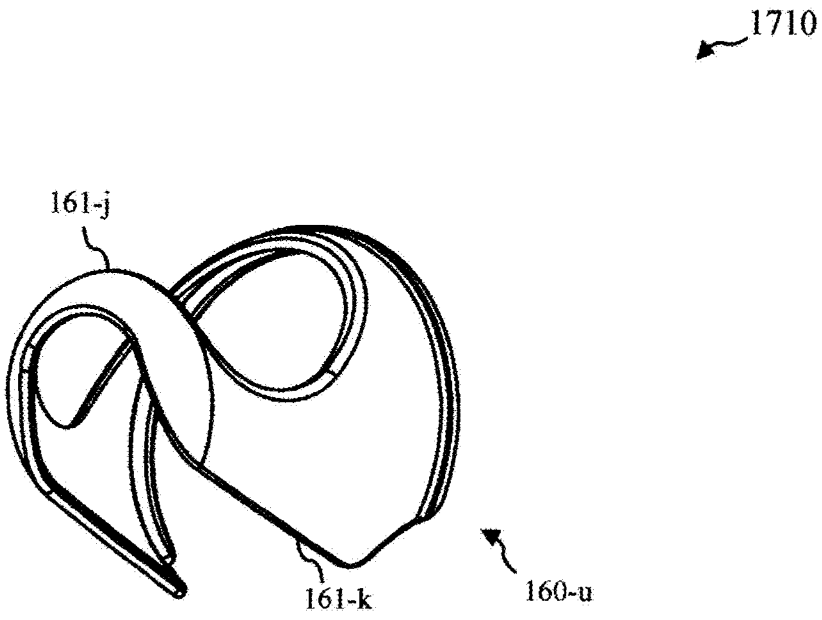
FIGS. 17A and 17B show a system and/or a device to facilitate skin care in accordance with various embodiments.

FIG. 17A shows a specific example of a device 1710 to facilitate skin care is provided in accordance with various embodiments. Device 1710 may be an example of aspects of system 110 of FIG. 1A and/or system 1010 of FIG. 10, for example. Device 1710 may include a spacer 160-*u*, which may be configured to couple with a portable microscope (not shown). The spacer 160-*u* may include one or more apertures 161-*j*/161-*k*, which may be configured to facilitate the use of a skin tool and/or viewing of a skin site.

Figure 17B:
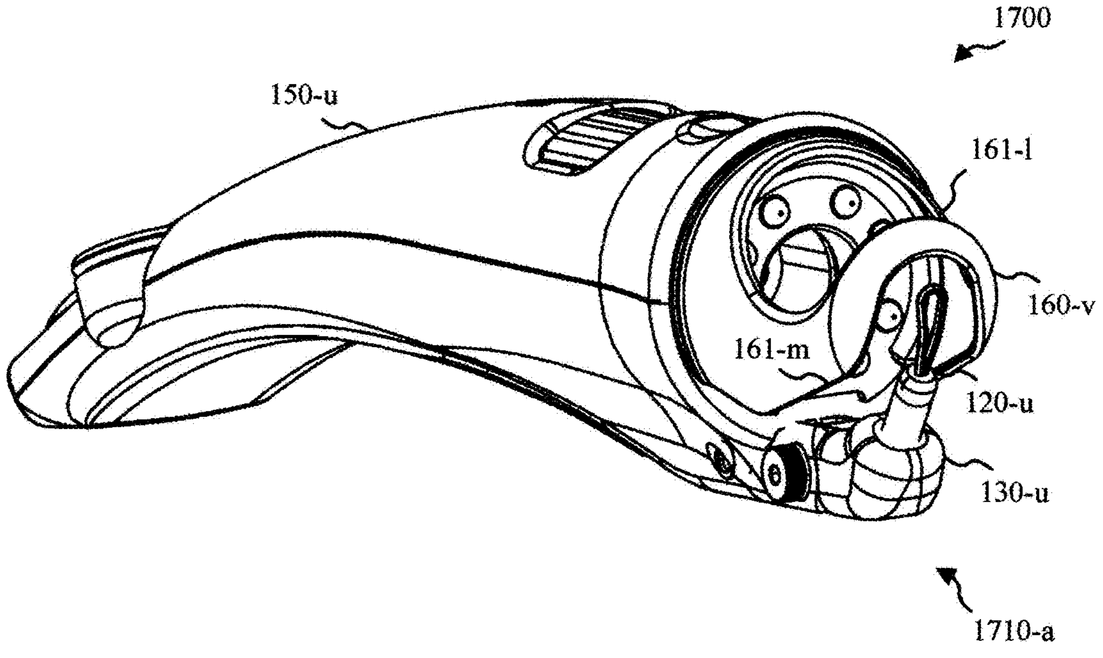

FIG. 17B shows a specific example of system 1700 to facilitate skin care is provided in accordance with various embodiments. System 1700 may be an example of system 100 of FIG. 1A, for example. System 1700 may include a device 1710-*a*, in particular, to facilitate skin care. Device 1710 may be an example of aspects of device 110 of FIG. 1A and/or device 1010 of FIG. 10. The device 1710-*a* may include multiple aspects such as a skin tool head portion 120-*u*, a skin tool head support 130-*u* that may be coupled with the skin tool head portion 120-*u*; the support 130-*u* may be configured to couple with a portable microscope 150-*u*. Device 1710 may include a spacer 160-*v*, which way be an example of spacer 160-*u* of FIG. 17A, which may be coupled with the skin tool head support 130-*u* and/or microscope 150-*u*.

In some cases, the skin tool head support 130-*u* along with the spacer 160-*v* may be configured to move such that at least a portion of the skin tool head portion 120-*u* may be positioned within a field of view of the portable microscope 150-*u*. The field of view of the portable microscope 150-*u* may include at least within a focal plane or at a focal point of the portable microscope 150-*u*. The skin tool head portion 120-*u* may include a variety of different skin tools; in this example, the skin tool head portion 120-*u* is shown as a comedone extractor, though other skin tools may be utilized. Spacer 160-*v* may one or more apertures 161-*l*, 161-*m*.

Figure 18A:
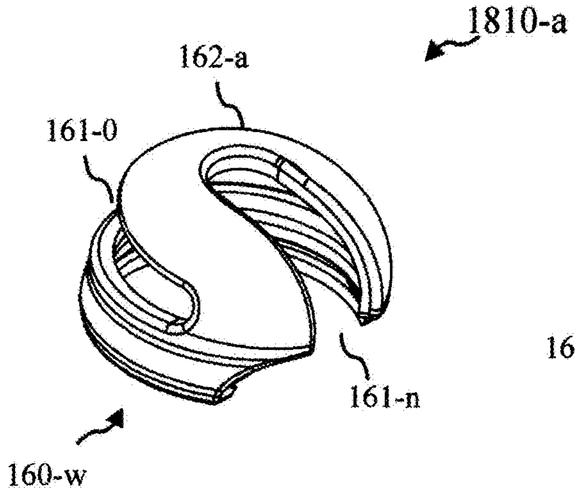
FIGS. 18A, 18B, 18C, and 18*d* show devices to facilitate skin care in accordance with various embodiments.
Figure 18B:
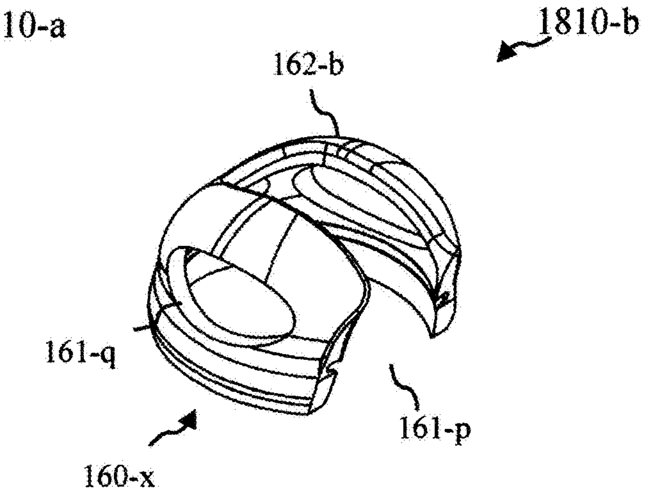
Figure 18C:
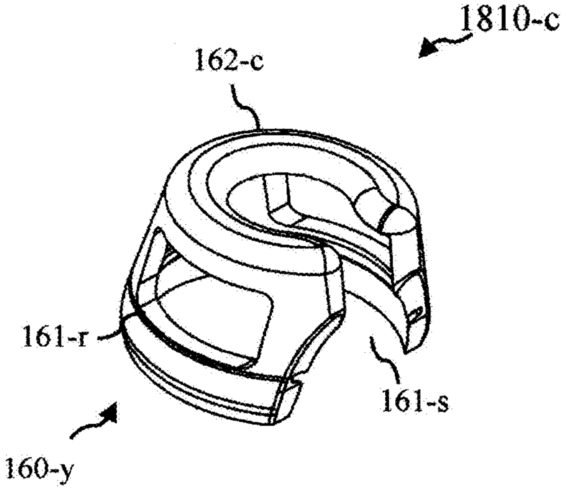
Figure 18D:
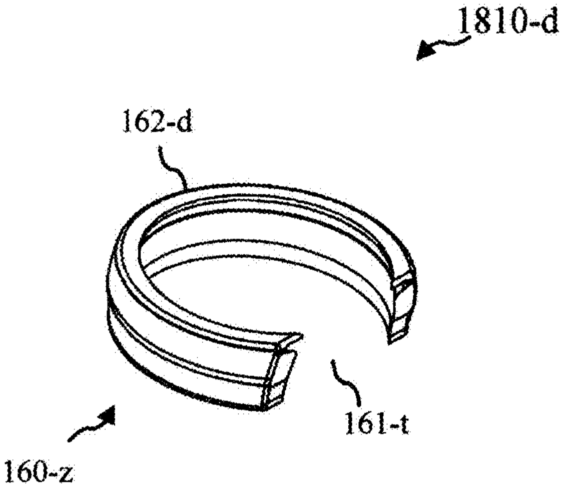
Figure 19A:
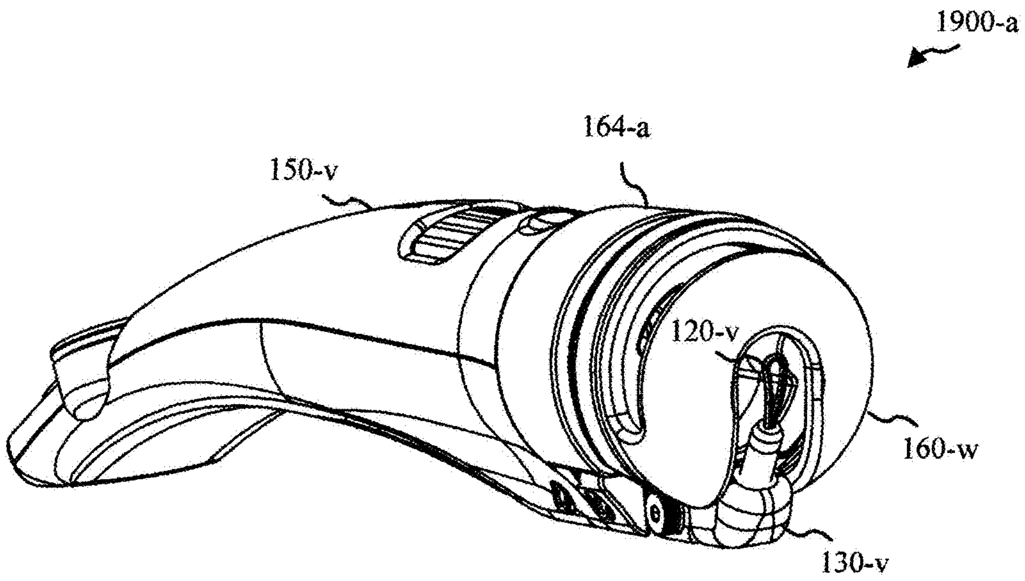
FIGS. 19A, 19B, 19C, and 19D show systems and/or devices to facilitate skin care in accordance with various embodiments.
Figure 19B:
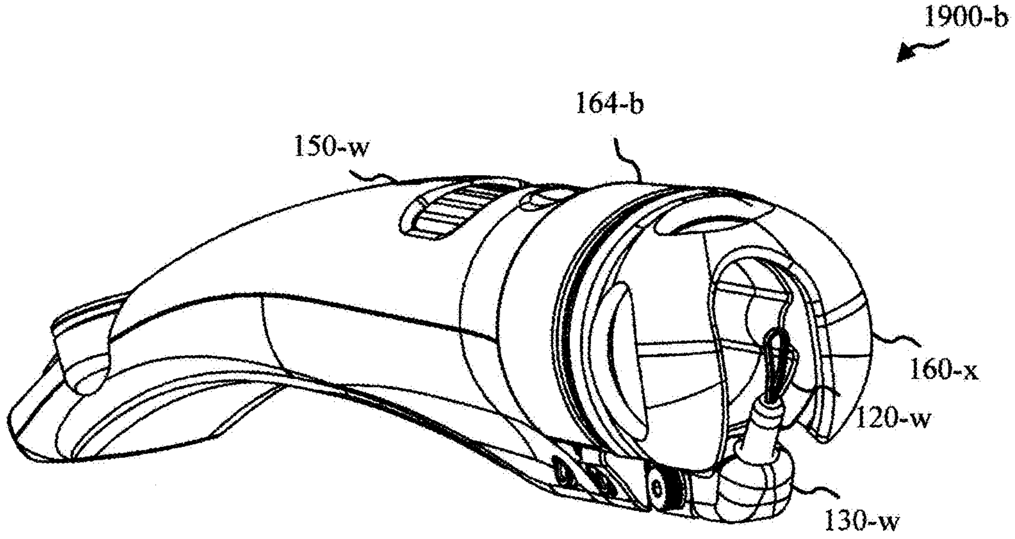
Figure 19C:
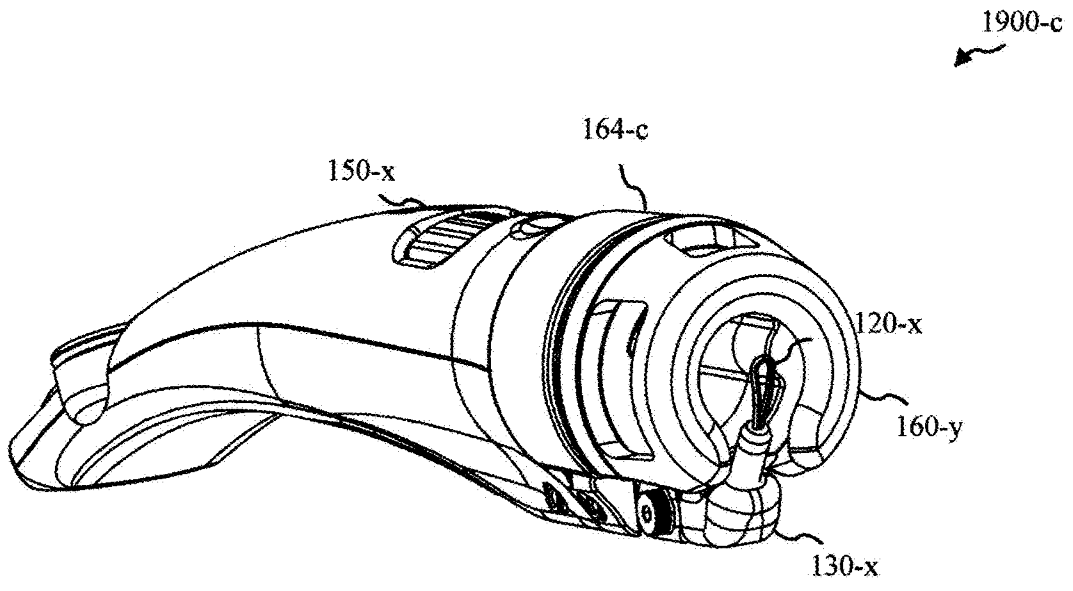
Figure 19D:
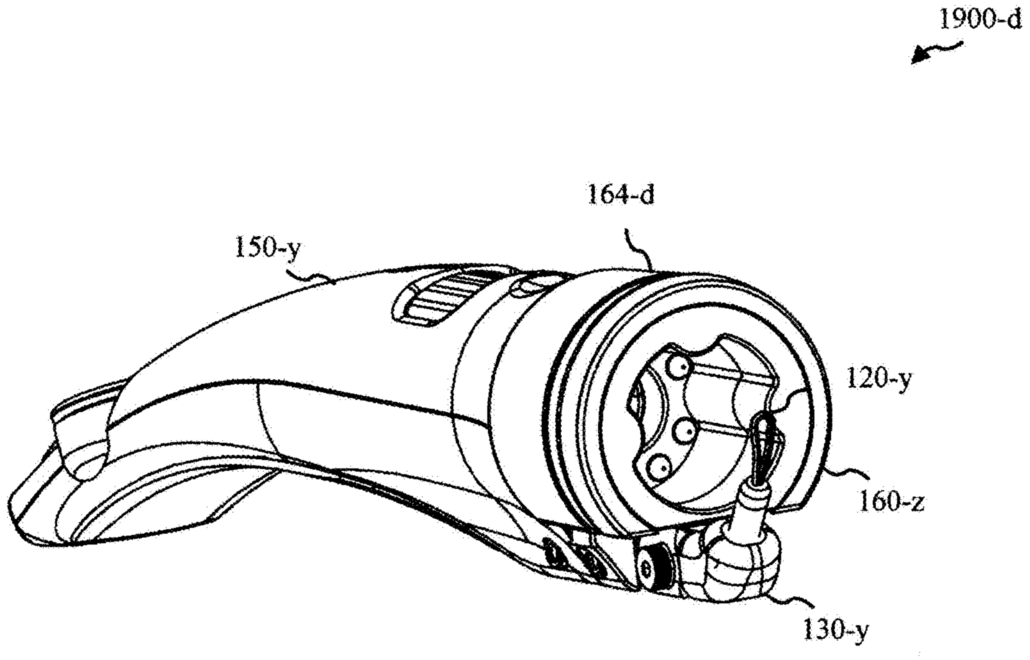

Turning now to FIG. 18A, FIG. 18B, FIG. 18C, and FIG. 18D, different examples of devices with spacers 160-*w*, 160-*x*, 160-*y*, 160-*z*, respectively, are shown in accordance with various embodiments. For example, FIG. 18A shows a specific example of a device 1810-*a* to facilitate skin care is provided in accordance with various embodiments. Device 1810-*a* may be an example of aspects of system 110 of FIG. 1A and/or system 1010 of FIG. 10, for example. Device 1810-*a* may include a spacer 160-*w*, which may be configured to couple with a portable microscope (not shown). The spacer 160-*w* may include one or more apertures 161-*n*/161-*o*, which may be configured to facilitate the use of a skin tool and/or viewing of a skin site. Spacer 160-*w* may include a skin contact portion 162-*a*, which may be generally U-shaped. The general U-shape may allow for the accommodation of a tool, such as a skin tool. FIG. 18B shows a specific example of a device 1810-*b* to facilitate skin care is provided in accordance with various embodiments. Device 1810-*b* may be an example of aspects of system 110 of FIG. 1A and/or system 1010 of FIG. 10, for example. Device 1810-*b* may include a spacer 160-*x*, which may be configured to couple with a portable microscope (not shown). The spacer 160-*x* may include one or more apertures 161-*p*/161-*q*, which may be configured to facilitate the use of a skin tool and/or viewing of a skin site. Spacer 160-*x* may include a skin contact portion 162-*b* that may be generally include two rounded portions that may include apertures such as aperture 161-*q*. Spacer 160-*x* may include a skin contact portion 162-*a*, which may be generally U-shaped or partial dome-shaped. The general U-shape may allow for the accommodation of a tool, such as a skin tool. FIG. 18C shows a specific example of a device 1810-*c* to facilitate skin care is provided in accordance with various embodiments. Device 1810-*c* may be an example of aspects of system 110 of FIG. 1A and/or system 1010 of FIG. 10, for example. Device 1810-*c* may include a spacer 160-*y*, which may be configured to couple with a portable microscope (not shown). The spacer 160-*y* may include one or more apertures 161-*r*/161-*s*, which may be configured to facilitate the use of a skin tool and/or viewing of a skin site. Spacer 160-*y* may include a skin contact portion 162-*c* that may generally include a flat or curved C-shaped portion. The general C-shape may allow for the accommodation of a tool, such as a skin tool. FIG. 18D shows a specific example of a device 1810-*d* to facilitate skin care is provided in accordance with various embodiments. Device 1810-*d* may be an example of aspects of system 110 of FIG. 1A and/or system 1010 of FIG. 10, for example. Device 1810-*d* may include a spacer 160-*z*, which may be configured to couple with a portable microscope (not shown). The spacer 160-*z* may include one or more apertures 161-*t*, which may be configured to facilitate the use of a skin tool and/or viewing of a skin site. Spacer 160-*z* may generally be C-shaped. Spacer 160-*z* may include a top portion 162-*d*, which may be configured as a skin contact portion. In some embodiments, spacer 160-*z* may be utilized as a connector element to facilitate connecting another spacer, such as spacers 160-*w*, 160-*x*, and/or 160-*y* to a portable microscope. While FIGS. 18A, 18B, 18C, and/or 18D show a variety of different shaped spacers, such as U-shaped, partial dome-shaped, and/or C-shaped, other shapes may be utilized including, but not limited to O-shaped spacers. An example of such a shaped spacer may be shown in FIG. 8B, for example.

FIG. 19A, FIG. 19B, FIG. 19C, and FIG. 19D show specific examples of systems 1900-*a*, 1900-*b*, 1900-*c*, and 1900-*d*, respectively, where each system includes a respective spacer 160-*w*, 160-*x*, 160-*y*, and 160-*z* of FIG. 18A, FIG. 18B, FIG. 18C, and FIG. 18D, in accordance with various embodiments. Each respective system 1900-*a*, 1900-*b*, 1900-*c*, and 1900-*d* also includes a portable microscope 150-*v*, 150-*w*, 150-*x*, 150-*y*, a skin tool head portion 120-*v*, 120-*w*, 120-*x*, 120-*y*, and a skin tool support 130-*v*, 130-*w*, 130-*x*, 130-*y* respectively. Systems 1900-*a*, 1900-*b*, 1900-*c*, and/or 1900-*d* may be examples of system 100 of FIG. 1A and/or variations of system 1700-*a* of FIG. 17B. Systems 1900-*a*, 1900-*b*, 1900-*c*, and/or 1900-*d* may also include connectors 164-*a*, 164-*b*, 164-*c*, 164-*d*, respectively, that may be utilized to facilitate coupling each respective spacer 160-*w*, 160-*x*, 160-*y*, 160-*z* with a respective portable microscope 150-*v*, 150-*w*, 150-*x*, 150-*y*. In some embodiments, connectors 164-*a*, 164-*b*, 164-*c*, and/or 164-*d* may be configured as compressible structures, such as compressible structures 163 of FIG. 1A and/or FIG. 10. In some cases, connectors 164-*a*, 164-*b*, 164-*c*, and/or 164-*d* may be configured as compressible structures as described with respect to spring-loaded attachment platforms and/or compressible cuffs 2010 as described and/or shown with respect to FIG. 20A, FIG. 20B, FIG. 20C and/or FIG. 20D below. In some embodiments, connectors 164-*a*, 164-*b*, 164-*c*, and/or 164-*d* may be configured as static structures.

Turning now to FIG. 20A, FIG. 20B, FIG. 20C, and FIG. 20D these figures show specific examples of systems 2000-*a*, 2000-*b*, 2000-*c*, and 2000-*d*, respectively, configured to facilitate skin care in accordance with various embodiments. In particular, these systems may include a spacer along with possible other components configured such that the spacer may move. This may facilitate skin care. For example, the spacer may be utilized to scan over a skin site. The spacer may also be utilized to provide a skin anchor at a specific location. In some cases, the spacer may be utilized to spread a portion of skin at the specific location. Once the desired area of skin may be determined, the portable microscope may be moved towards the skin site. As this occurs, the spacer may move towards the portable microscope. In some cases, this may result in a skin tool be exposed or moved towards the skin site so that the skin tool may be utilized with respect to the skin site. Different embodiments may utilize different configurations and/or materials to achieve these results. For example, the system may include a spring-loaded spacer. Other mechanisms besides springs may be utilized such as compressible or other flexible materials. In some cases, the spacer itself may be made of a flexible material so that it may move or flex when a pressure is applied. Some embodiments may also utilize a wave spring or otherwise flexible material.

In general, systems 2000-*a*, 2000-*b*, 2000-*c*, and/or 2000-*d* include several similar components including a respective spacer 160-*aa*, 160-*bb*, 160-*cc*, and 160-*dd*. Each respective system 2000-*a*, 2000-*b*, 2000-*d*, and 2000-*d*, may also include a portable microscope 150-*aa*, 150-*bb*, 150-*cc*, and/or 150-*dd*, a skin tool head portion 120-*aa*, 120-*bb*, 120-*cc*, and/or 120-*dd*, and a skin tool support 130-*aa*, 130-*bb*, 130-*cc*, and/or 130-*dd*, respectively. Systems 2000-*a*, 2000-*b*, 2000-*c*, and/or 2000-*d* may be examples of system 100 of FIG. 1A and/or variations of system 1700-*a* of FIG. 17B, system 1900-*a* of FIG. 19A, system 1900-*b* of FIG. 19B, system 1900-*c* of FIG. 19C, and/or system 1900-*d* of FIG. 19D. In some embodiments, systems 2000-*a*, 2000-*b*, 2000-*c*, and/or 2000-*d* may include an angle and/or arc adjuster 170-*a*, 170-*b*, 170-*c*, and/or 170-*d*, respectively, which may be utilized to adjust the angle and/or arc of the skin tool head portion 120-*aa*, 120-*bb*, 120-*cc*, and/or 120-*dd* and/or the skin tool support 130-*aa*, 130-*bb*, 130-*cc*, and/or 130-*dd* with respect to other components of the system, such as the spacers 160-*aa*, 160-*bb*, 160-*cc*, and 160-*dd*. In some embodiments, systems 2000-*a*, 2000-*b*, 2000-*c*, and/or 2000-*d* may include length adjusters 175-*a*, 175-*b*, 175-*c*, and/or 175-*d*, respectively, which may be utilized to adjust the position of the skin tool head portion 120-*aa*, 120-*bb*, 120-*cc*, and/or 120-*dd* and/or the skin tool support 130-*aa*, 130-*bb*, 130-*cc*, and/or 130-*dd* with respect to other components of the system, such as the spacers 160-*aa*, 160-*bb*, 160-*cc*, and 160-*dd*.

In addition, system 2000-*a*, system 2000-*b*, 2000-*c*, and/or 2000-*d* may be configured such that the spacers 160-*aa*, 160-*bb*, 160-*cc*, and 160-*ddc* may be coupled with or integrated with a compressible portion or structure, such as a spring-loaded attachment platform 2010-*a*, 2010-*b*, and/or 2010-*c* or compressible cuff 2010-*d*, respectively. Spring-loaded attachment platform 2010-*a*, 2010-*b*, and/or 2010-*c* and/or compressible cuff 2010-*d* may be examples of compressible structures 163 of FIG. 1A and/or FIG. 10 or connectors 164 of FIG. 19A, FIG. 19B, FIG. 19C, and/or FIG. 19D.

The use of a spring-loaded attachment platform 2010 or other compressible structure may the spacers 160-*aa*, 160-*bb*, 160-*cc*, and 160-*dd* to retract relative to the skin tool head portion 120-*aa*, 120-*bb*, 120-*cc*, and 120-*dd*, as the spacers 160-*aa*, 160-*bb*, 160-*cc*, and 160-*dd* may be pressed into the skin.

Spring-loaded attachment platform 2010-*a*, 2010-*b*, and/or 2010-*c* may include additional components. For example, they may include spring holders 2020-*a*, 2020-*b*, and 2020-*c*, respectively, in FIG. 20A, FIG. 20B, and FIG. 20C. These may also act as part of the housing of the spring-loaded attachment platform 2010-*a*, 2010-*b*, and/or 2010-*c*. Some embodiments may also include travel limiter 2030-*a*, 2030-*b*, and/or 2030-*c*, respectively, in FIG. 20A, FIG. 20B, and FIG. 20C. These may be utilized to shorten or lengthen a possible travel distance for spacers 160-*aa*, 160-*bb*, and/or 160-*cc*. For example, a longer travel limiter may result in the spacer being able to travel a shorter distance, while a shorter travel limiter may allow the spacer to travel a longer distance. Compressible cuff 2010-*d* of FIG. 20D may be made of a compressible material, such as rubber, flexible plastic, or other material.

Figure 20A:
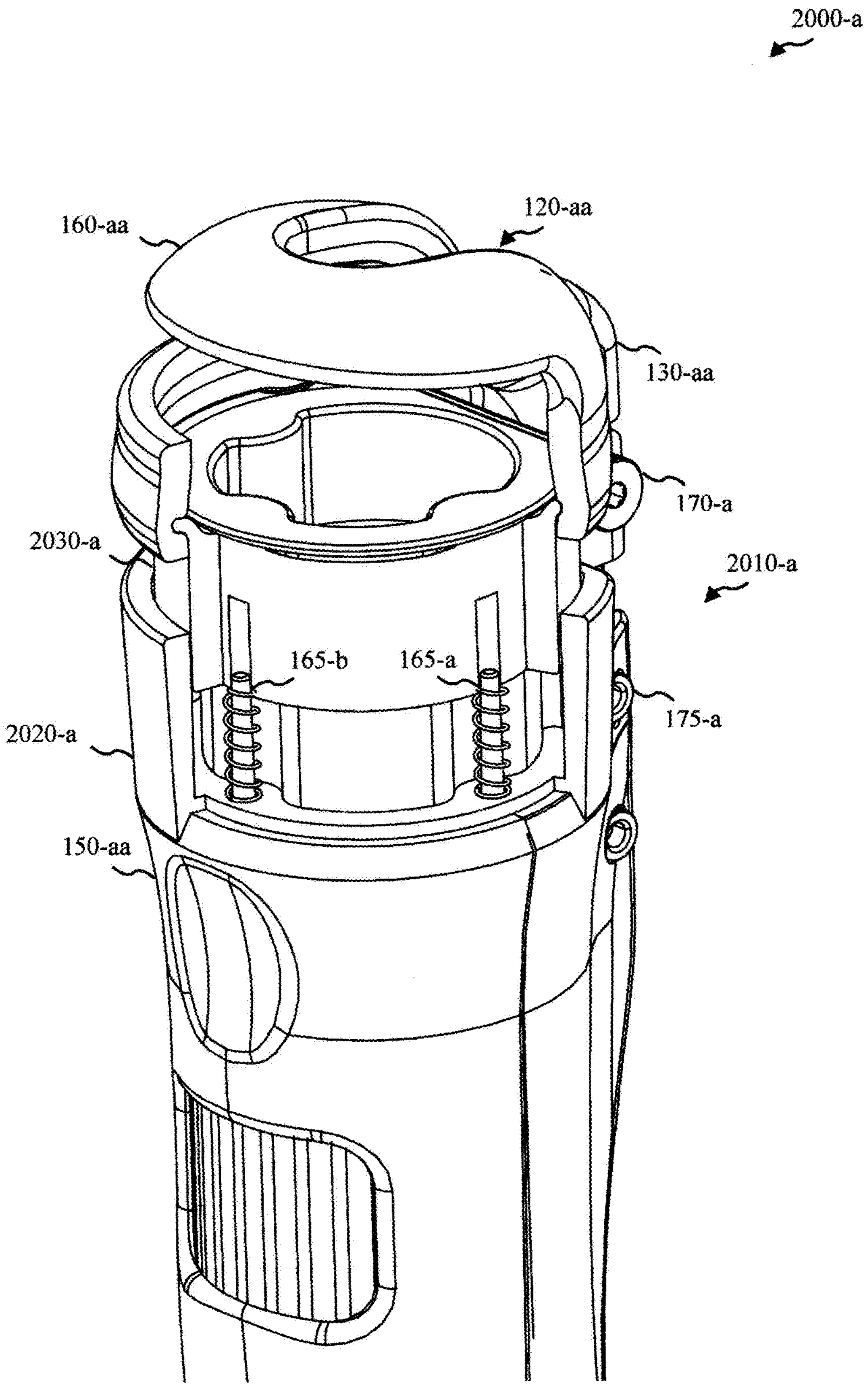
FIGS. 20A, 20B, 20C, and 20D show systems and/or devices to facilitate skin care in accordance with various embodiments.

As shown in FIG. 20A, for example, the spacer 160-*aa* may be attached to the portable microscope 150-*aa* via a spring-loaded platform 2010-*a*. Springs 165-*a*/165-*b* may be in an uncompressed state. The skin tool head portion 120-*aa* may be shrouded by the spacer 160-*aa*, which may the skin tool head portion 120-*aa* from contacting the skin. The user may scan the skin surface, utilizing the spacer 160-*aa* as the means to move over the skin. While FIG. 20A may show two or more springs, more or less springs 165 may be utilized in different embodiments.

Figure 20B:
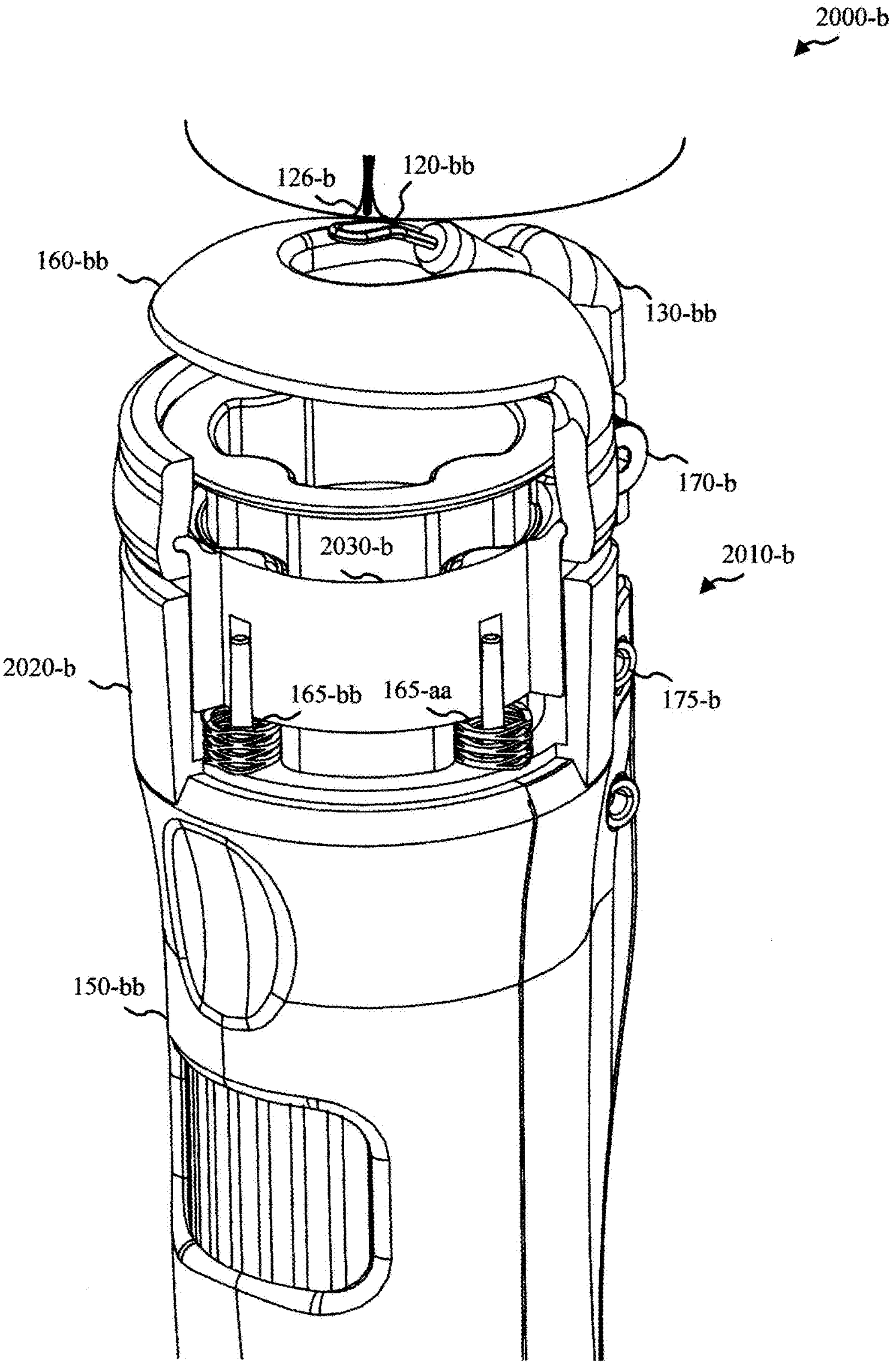

When a clogged pore is located or a portion of skin of interest is identified in general, the user may position the skin tool head portion 120-*aa* with respect to the skin site. The user may press the entire device and/or system towards the skin. FIG. 20B shows an example where the device and/or system has been moved towards the skin site 126-*b*, such as perpendicular to the skin surface. This may cause the spring(s) 165-*aa*/165-*bb* in the spacer platform 2010-*b* to compress. This compression of the spring-loaded spacer may expose the skin tool head portion 120-*bb* and may allow it to directly contact the skin, which may enable a clogged pore to be cleared by the skin tool head portion 120-*bb* or other manipulation of the skin with a skin tool in general.

As the user pulls the entire device and/or system back from the skin, the compressed spring force may return the spacer to an extended position, which again shrouds the tool head, as shown in FIG. 20A.

Figure 20C:
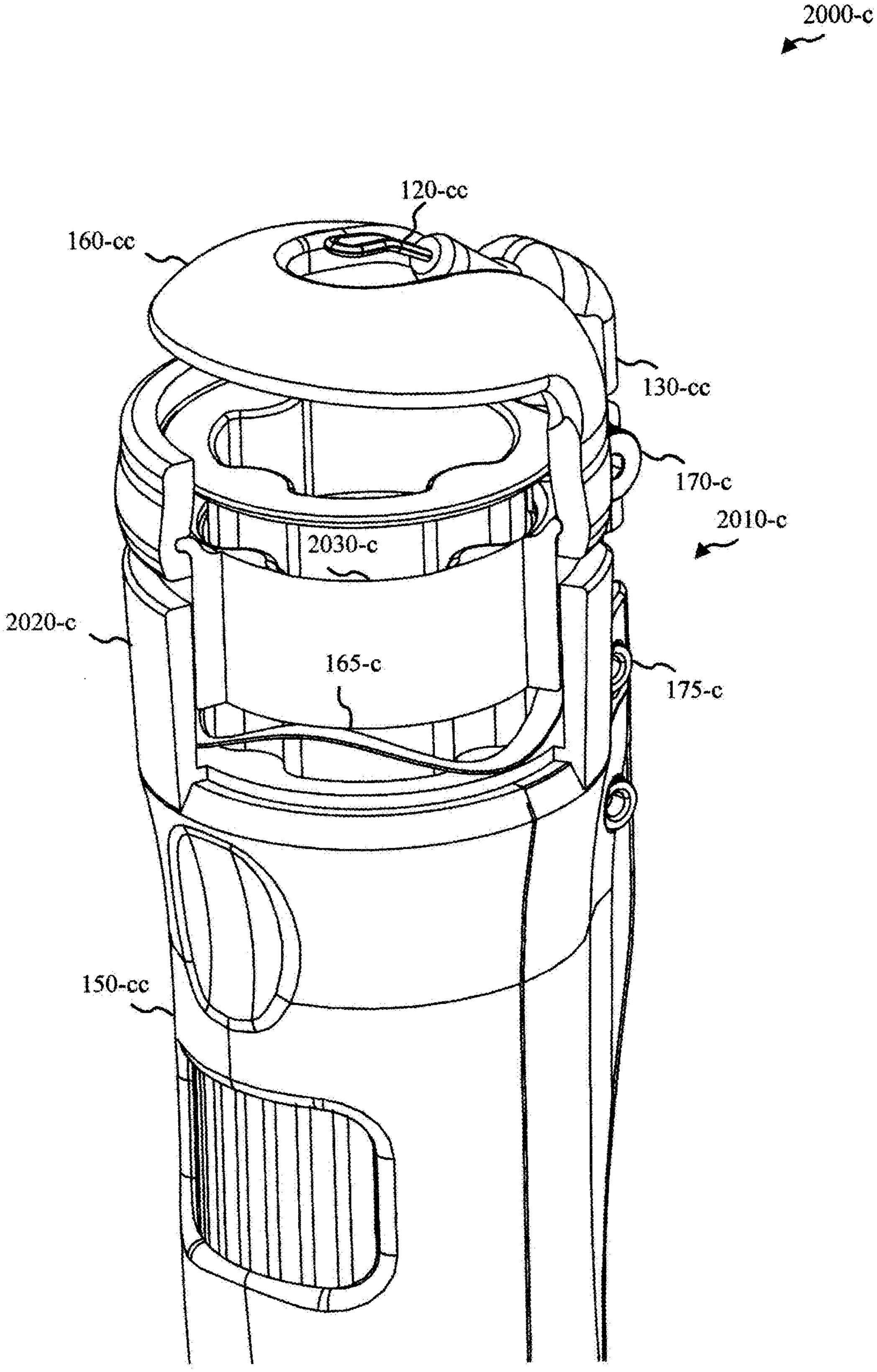
Figure 20D:
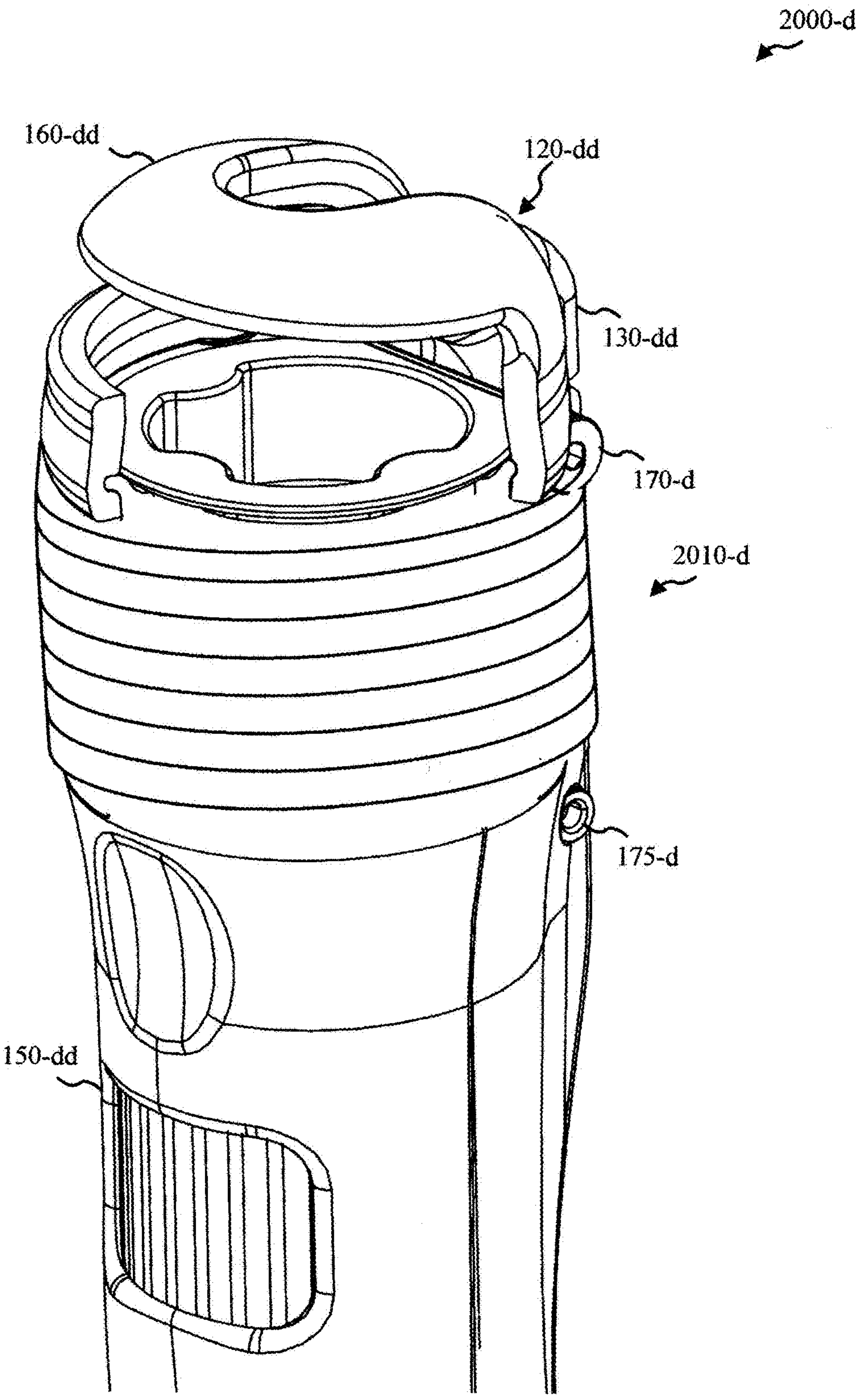

FIG. 20C shows a variation on the system that utilizes one or more wave springs 165-*c*. Other embodiments may utilize other compressible materials not limited to springs. FIG. 20D shows a variation on the system that utilizes a compressible cuff 2010-*d*.

Figure 21A:
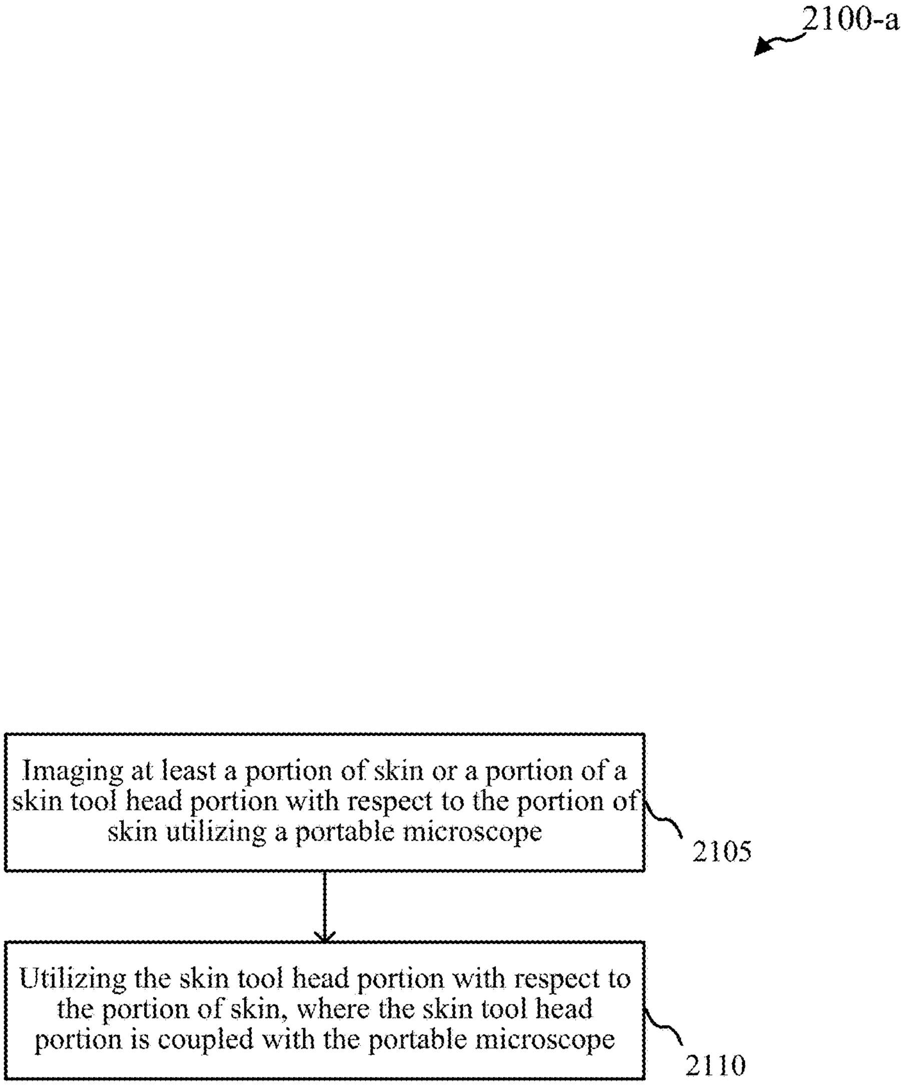
FIG. 21A shows a flow diagram of a method of skin care in accordance with various embodiments.

FIG. 21A shows a flow diagram 2100-*a* of a method of skin care in accordance with various embodiments. Method 2100-*a* may be implemented by a variety of systems, devices, and/or configurations including, but not limited to, those show and/or described with regarding to FIGS. 1A, 1B, 1C, 1D, 1E, IF, 1G, 1H, 2A, 2B, 2C, 3A, 3B, 3C, 4A, 4B, 5A, 5B, 5C, 6A, 6B, 6C, 7A, 7B, 8A, 8B, 8C, 9, 10, 11A, 11B, 12, 13, 14, 15, 16, 17A, 17B, 18A, 18B, 18C, 18D, 19A, 19B, 19C, 19D, 20A, 20B, 20C, and/or 20D.

At block 2105, at least a portion of skin or a portion of a skin tool head portion with respect to the portion of skin may be imaged utilizing a portable microscope. The imaging may include static imagining, such as a photograph imaging, or live imaging, such as video imaging. At block 2110, the skin tool head portion may be utilized with respect to the portion of skin. The skin tool head portion is coupled with the portable microscope.

In some embodiments, utilizing the skin tool head portion with respect to the portion of skin includes applying pressure to the portion of skin with the skin tool head portion. Applying the pressure may include modulating the pressure. Modulating the pressure may depend upon information determined from the imaging.

Some embodiments may further include illuminating at least the portion of skin utilizing at least polarized light or ultraviolet light. Illuminating at least the portion of the skin further may include illuminating at least a hair shaft or comedone. Some embodiments may further include utilizing another skin tool head portion with respect to the portion of skin through an aperture of a spacer of the portable microscope.

The method may include utilizing a spacer coupled with the portable microscope to anchor the portable microscope with respect to a portion of skin. The method may include moving the portable microscope towards to the portion of skin, wherein moving the portable microscope exposes the skin tool head portion with respect to the spacer to allow the skin tool head portion to contact the portion of skin. In some cases, the spacer may be utilized to spread the portion of skin.

Figure 21B:
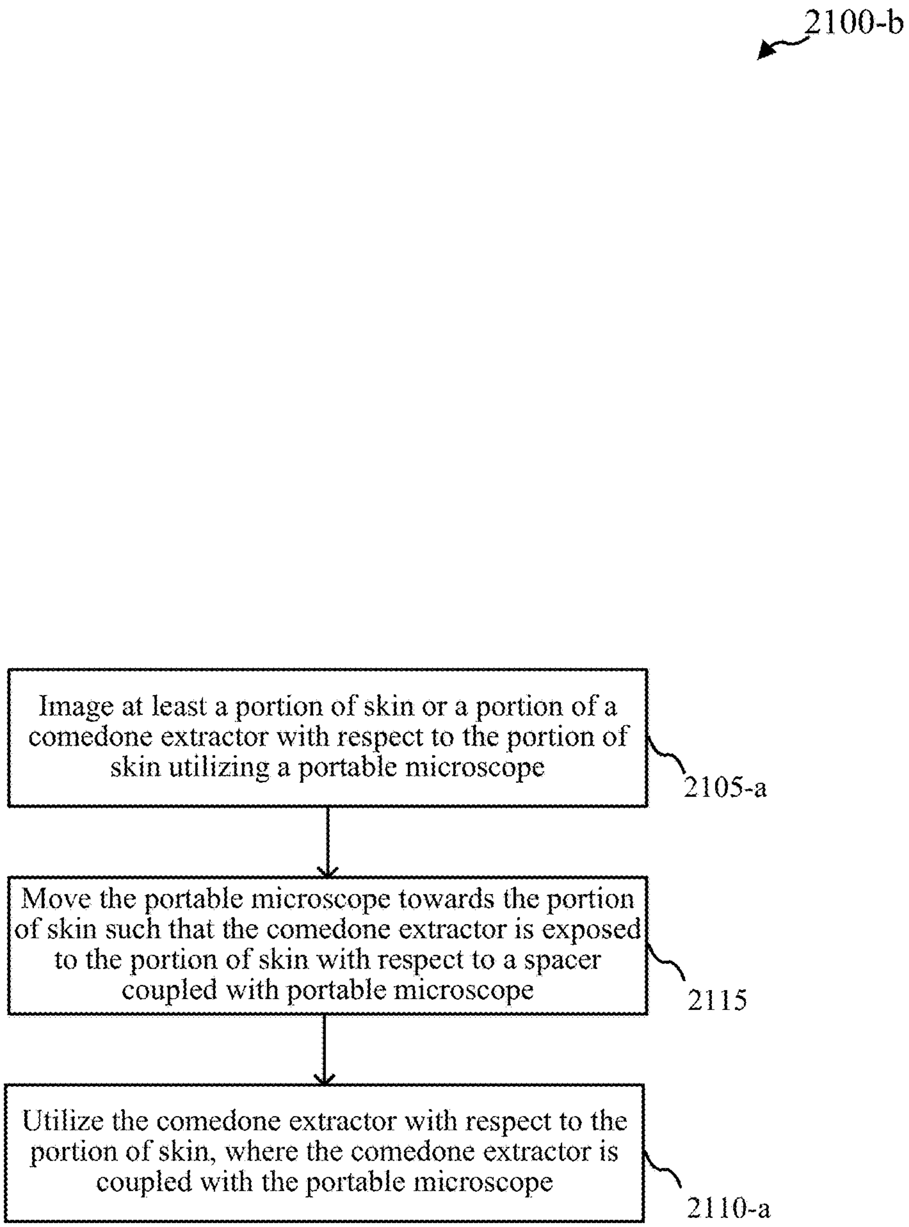
FIG. 21B shows a flow diagram of a method of skin care in accordance with various embodiments.

FIG. 21B shows a flow diagram 2100-*b* of a method of skin care in accordance with various embodiments. Method 2100-*b* may be implemented by a variety of systems, devices, and/or configurations including, but not limited to, those show and/or described with regarding to FIGS. 1A, 1B, 1C, 1D, 1E, IF, 1G, 1H, 2A, 2B, 2C, 3A, 3B, 3C, 4A, 4B, 5A, 5B, 5C, 6A, 6B, 6C, 7A, 7B, 8A, 8B, 8C, 9, 10, 11A, 11B, 12, 13, 14, 15, 16, 17A, 17B, 18A, 18B, 18C, 18D, 19A, 19B, 19C, 19D, 20A, 20B, 20C, and/or 20D. Method 2100-*b* may be an example of method 2100-*a* of FIG. 21A.

At block 2105-*a*, at least a portion of skin or a portion of a comedone extractor with respect to the portion of skin may be imaged utilizing a portable microscope. At block 2115, the portable microscope may be moved towards the portion of skin such that the comedone extractor is exposed to the portion of skin with respect to a spacer coupled with portable microscope. At block 2110-*a*, the comedone extractor may be utilized with respect to the portion of skin, where the comedone extractor is coupled with the portable microscope.

Figure 22A:
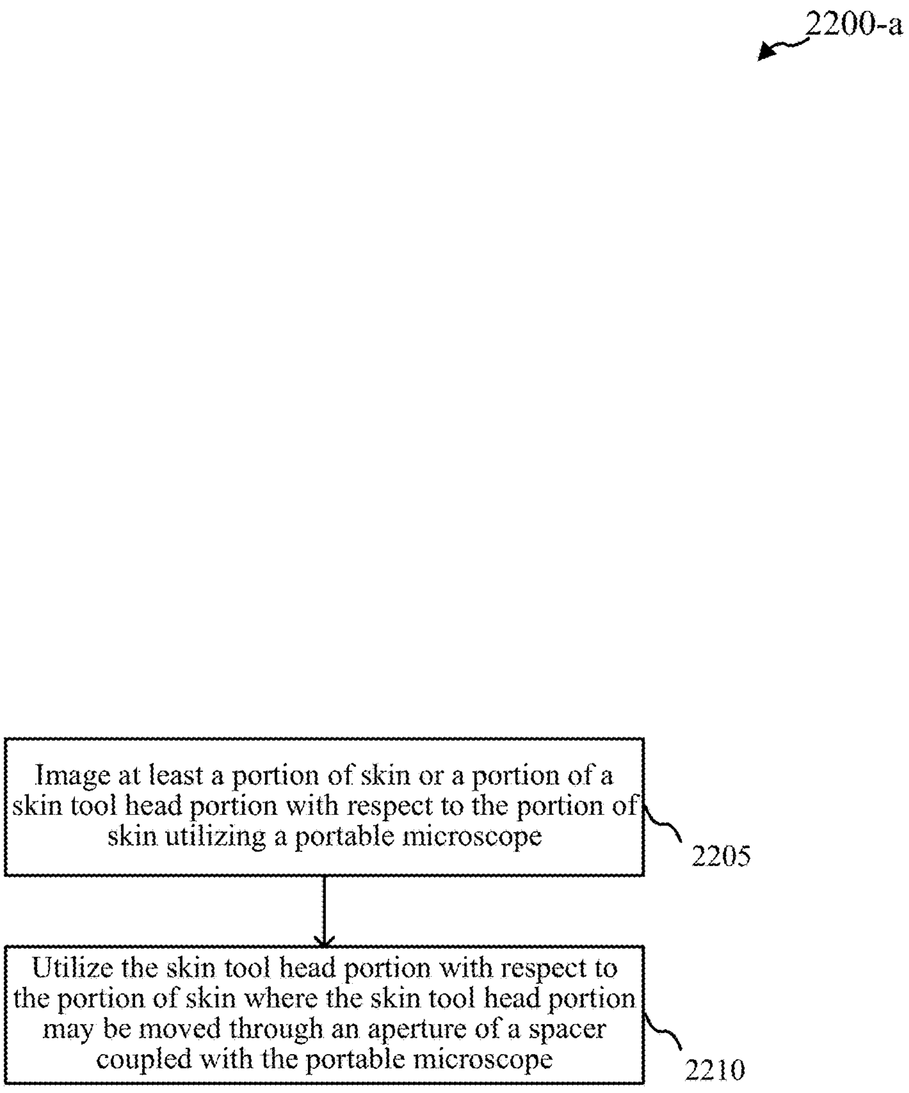
FIG. 22A shows a flow diagram of a method of skin care in accordance with various embodiments.

FIG. 22A shows a flow diagram 2200-*a* of a method of skin care in accordance with various embodiments. Method 2200-*a* may be implemented by a variety of systems, devices, and/or configurations including, but not limited to, those show and/or described with regarding to FIGS. 1A, 1B, 1C, 1D, 1E, IF, 1G, 1H, 2A, 2B, 2C, 3A, 3B, 3C, 4A, 4B, 5A, 5B, 5C, 6A, 6B, 6C, 7A, 7B, 8A, 8B, 8C, 9, 10, 11A, 11B, 12, 13, 14, 15, 16, 17A, 17B, 18A, 18B, 18C, 18D, 19A, 19B, 19C, 19D, 20A, 20B, 20C, and/or 20D.

At block 2205, at least a portion of skin or a portion of a skin tool head portion with respect to the portion of skin may be imaged utilizing a portable microscope. At block 2210, the skin tool head portion may be utilized with respect to the portion of skin. The skin tool head portion may be moved through an aperture of the portable microscope or an aperture of a spacer coupled with the portable microscope.

In some embodiments, the skin tool head portion includes at least a comedone extractor, a lancet, a needle, or tweezers. Some embodiments may further include illuminating at least the portion of skin utilizing at least polarized light or ultraviolet light.

Figure 22B:
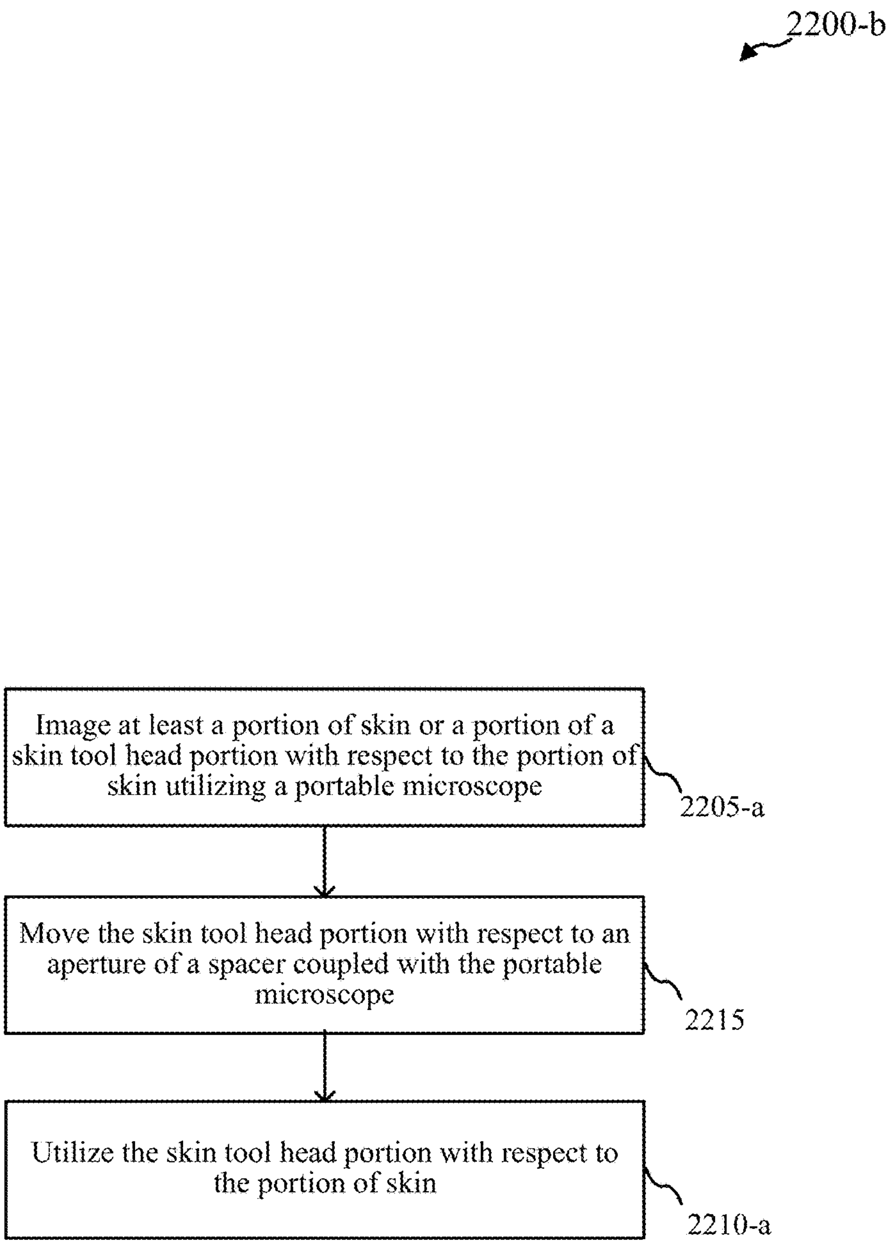
FIG. 22B shows a flow diagram of a method of skin care in accordance with various embodiments.

FIG. 22B shows a flow diagram 2200-*b* of a method of skin care in accordance with various embodiments. Method 2200-*b* may be implemented by a variety of systems, devices, and/or configurations including, but not limited to, those show and/or described with regarding to FIGS. 1A, 1B, 1C, 1D, 1E, IF, 1G, 1H, 2A, 2B, 2C, 3A, 3B, 3C, 4A, 4B, 5A, 5B, 5C, 6A, 6B, 6C, 7A, 7B, 8A, 8B, 8C, 9, 10, 11A, 11B, 12, 13, 14, 15, 16, 17A, 17B, 18A, 18B, 18C, 18D, 19A, 19B, 19C, 19D, 20A, 20B, 20C, and/or 20D. Method 2200-*b* may be an example of method 2200-*a* of FIG. 22A.

At block 2205-*a*, at least a portion of skin or a portion of a skin tool head portion with respect to the portion of skin may be imaged utilizing a portable microscope. At block 2215, the skin tool head portion may be moved with respect to an aperture of a spacer coupled with the portable microscope. At block 2210-*a*, the skin tool head portion may be utilized with respect to the portion of skin. In some embodiments, the skin tool head portion includes least a comedone extractor, a lancet, a needle, or tweezers.

Some embodiments of method 2200-*b* may include moving the spacer with respect to the portion of skin. Some embodiments include utilizing the spacer to anchor the portable microscope with respect to the portion of skin. In some embodiments, the spacer may be utilized to spread the portion of skin. In some embodiments, the skin tool head portion is independent from the portable microscope.

In some embodiments, the skin tool head portion is coupled with the portable microscope. Some embodiments include moving the portable microscope towards to the portion of skin, where moving the portable microscope exposes the skin tool head portion with respect to the spacer to allow the skin tool head portion to contact the portion of skin. In some embodiments, a compressible structure positioned between the portable microscope and the spacer facilitates exposing the skin tool head portion with respect to the spacer. In some embodiments, at least a portion of the spacer comprises a flexible material to facilitate exposing the skin tool head portion with respect to the spacer.

In some embodiments, moving the skin tool head portion with respect to the aperture of the spacer includes moving the skin tool head portion through the aperture of the spacer.

Figure 22C:
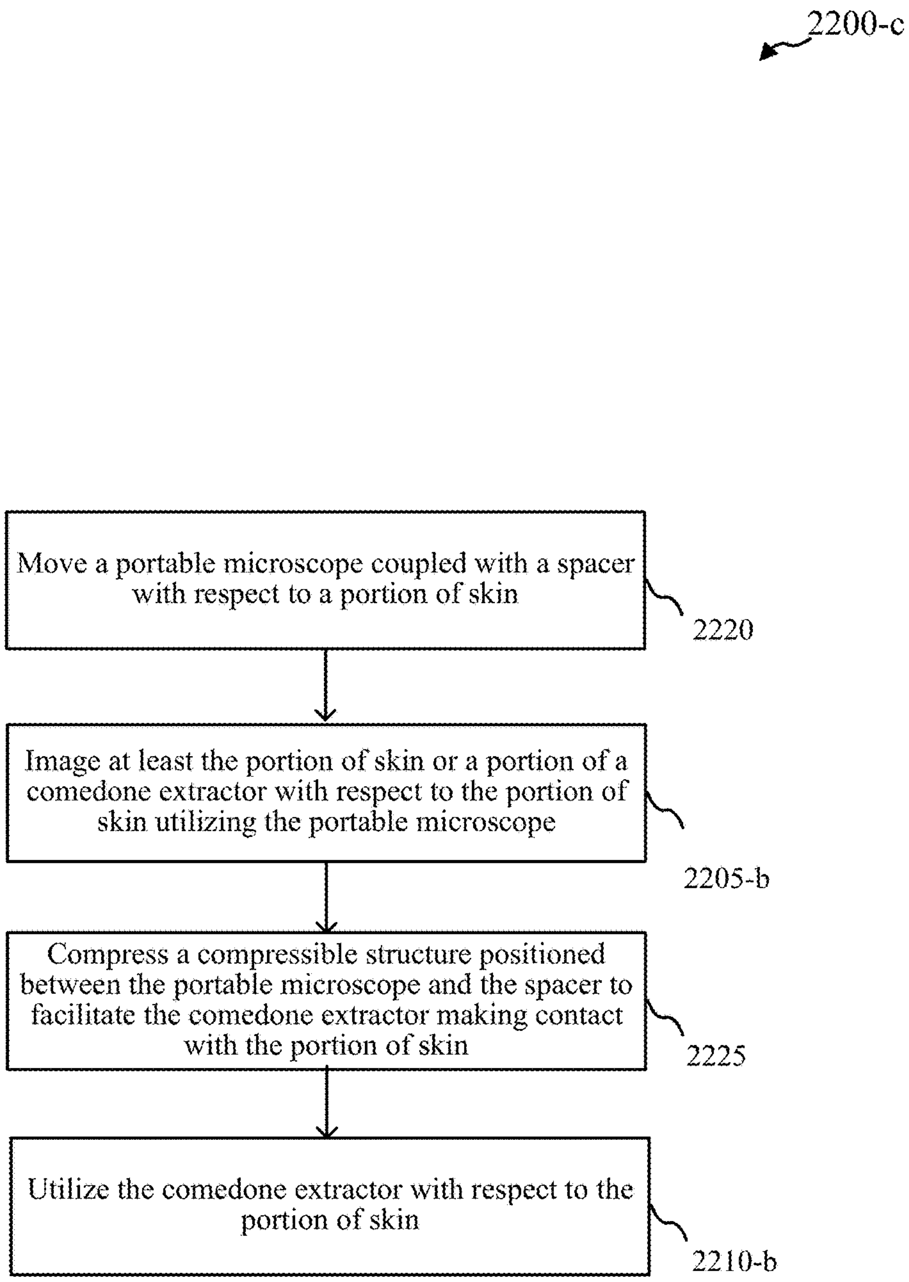
FIG. 22C shows a flow diagram of a method of skin care in accordance with various embodiments.

FIG. 22C shows a flow diagram 2200-*c* of a method of skin care in accordance with various embodiments. Method 2200-*c* may be implemented by a variety of systems, devices, and/or configurations including, but not limited to, those show and/or described with regarding to FIGS. 1A, 1B, 1C, 1D, 1E, IF, 1G, 1H, 2A, 2B, 2C, 3A, 3B, 3C, 4A, 4B, 5A, 5B, 5C, 6A, 6B, 6C, 7A, 7B, 8A, 8B, 8C, 9, 10, 11A, 11B, 12, 13, 14, 15, 16, 17A, 17B, 18A, 18B, 18C, 18D, 19A, 19B, 19C, 19D, 20A, 20B, 20C, and/or 20D. Method 2200-*c* may be an example of method 2200-*a* of FIG. 22A and/or method 2200-*b* of FIG. 22B.

At block 2220, a portable microscope coupled with a spacer may be moved with respect to a portion of skin. At block 2205-*b*, at least the portion of skin or a portion of a comedone extractor with respect to the portion of skin may be imaged utilizing the portable microscope. At block 2225, a compressible structure positioned between the portable microscope and the spacer may be compressed to facilitate the comedone extractor making contact with the portion of skin. At block 2210-*b*, the comedone extractor may be utilized with respect to the portion of skin.

The detailed description set forth above in connection with the appended drawings describes exemplary embodiments and does not represent the only embodiments that may be implemented or that are within the scope of the claims. The term "exemplary" used throughout this description means "serving as an example, instance, or illustration," and not "preferred" or "advantageous over other embodiments." The detailed description includes specific details for the purpose of providing an understanding of the described techniques. These techniques, however, may be practiced without these specific details. In some instances, well-known structures and devices are shown in block diagram form in order to avoid obscuring the concepts of the described embodiments.

The previous description of the disclosure is provided to enable a person skilled in the art to make or use the disclosure. Various modifications to the disclosure will be readily apparent to those skilled in the art, and the generic principles defined herein may be applied to other variations without departing from the spirit or scope of the disclosure. Throughout this disclosure the term "example" or "exemplary" indicates an example or instance and does not imply or require any preference for the noted example. Thus, the disclosure is not to be limited to the examples and designs described herein but is to be accorded the widest scope consistent with the principles and novel features disclosed herein.

What is claimed is:

1. A system for comedone extraction comprising:

a portable, digital microscope; and a comedone extractor coupled with the portable, digital microscope, wherein at least a portion of the comedone extractor is positioned at least within a field of view of the portable, digital microscope utilizing a skin tool head support coupled with the portable, digital microscope and coupled with the comedone extractor, wherein the comedone extractor is detachable from the skin tool head support and replaceable with an other comedone extractor coupled with the skin tool head support and wherein the other comedone extractor is positioned at least within the field of view of the portable, digital microscope.

2. The system of claim 1, wherein the skin tool head support is configured to couple with the comedone extractor and the other comedone extractor with a bolt.

3. The system of claim 1, wherein the skin tool head support is configured to couple with the comedone extractor and the other comedone extractor with a wing nut.

4. The system of claim 1, wherein at least the comedone extractor and the other comedone extractor are configured to rotate with respect to the skin tool head support.

5. The system of claim 4, wherein the comedone extractor is displaced from a first position to a second position through rotation.

6. The system of claim 5, wherein the other comedone extractor is displaced from the second position to the first position through the rotation.

7. The system of claim 1, wherein the skin tool head support is configured to couple with the comedone extractor or the other comedone extractor utilizing a magnet.

8. The system of claim 1, wherein the skin tool head support is configured to couple with the comedone extractor or the other comedone extractor utilizing a threaded portion.

9. The system of claim 1, wherein the comedone extractor is configured to displace from a first position to a second position.

10. The system of claim 9, wherein the comedone extractor is configured to displace from the first position to the second position through rotation.

11. The system of claim 10, wherein the comedone extractor is configured to displace from the first position to the second position through rotation around an axis of the skin tool head support.

12. The system of claim 10, wherein the comedone extractor is configured to displace from the first position to the second position through rotation around a pivot point positioned between the skin tool head support and the comedone extractor.

13. The system of claim 9, wherein the comedone extractor is configured to displace from the first position to the second position through displacement along an axis parallel to an axis of the portable, digital microscope.

14. The system of claim 1, wherein the skin tool head support is configured to displace along an axis parallel to an axis of the portable, digital microscope.

15. The system of claim 1, wherein the skin tool head support includes at least an angled portion or an arced portion such that the comedone extractor or the other comedone extractor is positioned within at least the field of view of the portable, digital microscope.

* * * * *